(12) United States Patent
Kaufman et al.

(10) Patent No.: US 9,181,223 B2
(45) Date of Patent: Nov. 10, 2015

(54) 2-AMINOPYRIMIDIN-6-ONES AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Michael D. Kaufman, Lawrence, KS (US); Daniel L. Flynn, Lawrence, KS (US); YuMi Ahn, Lawrence, KS (US); Lakshminarayana Vogeti, Arlington, MA (US); Timothy Malcolm Caldwell, Fishers, IN (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/214,171

(22) Filed: Mar. 14, 2014

(65) Prior Publication Data

US 2014/0275085 A1 Sep. 18, 2014

Related U.S. Application Data

(60) Provisional application No. 61/792,812, filed on Mar. 15, 2013.

(51) Int. Cl.
*A61K 31/506* (2006.01)
*C07D 401/14* (2006.01)
*C07D 405/14* (2006.01)

(52) U.S. Cl.
CPC ............ *C07D 401/14* (2013.01); *C07D 405/14* (2013.01); *A61K 31/506* (2013.01)

(58) Field of Classification Search
CPC .. C07D 401/14; C07D 413/14; C07D 417/14; A61K 31/541; A61K 31/506; A61K 31/5355
See application file for complete search history.

(56) References Cited

U.S. PATENT DOCUMENTS

2008/0214544 A1 9/2008 Bellon et al.
2008/0255155 A1 10/2008 Raeppel et al.

FOREIGN PATENT DOCUMENTS

WO WO 2008079291 A2 * 7/2008
WO WO2010/051373 A1 5/2010

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
A. Dewar et al., 4 Cell Cycle, 851-853 (2005).*
A.L. Dewar et al., 105 Blood 3127-3122 (2005).*
H. Ohno et al., 5 Molecular Cancer Therapeutics, 2634-2643 (2006).*
S. M. Pyonteck et al., 19 Nature Medicine, 1264-1272 (2013).*
C.J. Burns et al., 21 Expert Opinion on Therapeutic Patents, 147-165 (2011).*
N. Gupta et al., 185 Journal of Immunology, 2261-2272 (2010).*
M.C. Heinrich et al., 96 Blood, 929-932 (2000).*
S. Attoub et al., 62 Cancer Research, 4879-4883 (2002).*
B.P. Rubin et al., 61 Cancer Research, 8118-8121 (2001).*
R.D. Carvajal et al., 305 Journal of the American Medical Association, 2327-2334 (2011).*
A. Yasuda et al., 5 Molecular Cancer, 1-10 (2006).*
G. Di Lorenzo et al., 30 European Journal of Surgical Oncology, 987-992 (2004).*
A.Z. Al-Muhsen et al., 34 Clinical and Experimental Allergy, 911-917 (2004).*
M. Boissan. 67 Journal of Leukocyte Biology, 135-148 (2000).*
L. Reber et al., 533 European Journal of Pharmacology, 327-340 (2006).*
D.S. El Agamy et al, 690 European Journal of Pharmacology, 1-3 (2012).*
W.G. Roberts et al., 65 Cancer Research, 957-966 (2005).*
J. Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
S. Fogarty et al., 1804 Biochimica et Biophysica Acta, 581-591 (2010).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
P.A. LeWitt, 359 New England Journal of Medicine, 2468-2473 (2008).*
S. Judge et al., 111 Pharmacology & Therapeutics, 224-259 (2006).*
V. Brinkmann et al., 9 Nature Reviews | Drug Discovery, 883-897 (2010).*
J.D. Mitchell et al., 369 The Lancet, 2031-2041 (2007).*
Kinase Inhibitors, Methods in Molecular Biology 795 (B. Kuster ed., 2012).*
K. Henriksen et al., 18 Osteoporosis International, 681-685 (2006).*
C. Minkin, 34 Calcified Tissue International, 285-290 (1982).*
PCT International Search Report from corresponding PCT International Application No. PCT/US2014/029661, dated Nov. 6, 2014.

* cited by examiner

*Primary Examiner* — Alexander R Pagano
(74) *Attorney, Agent, or Firm* — Cooley LLP

(57) ABSTRACT

Described are compounds of Formula I

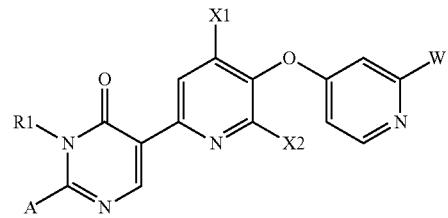

Formula I which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

29 Claims, No Drawings

SEQUENCE LISTING

```
<160> NUMBER OF SEQ ID NOS: 3

<210> SEQ ID NO 1
<211> LENGTH: 435
<212> TYPE: PRT
<213> ORGANISM: Homo sapiens

<400> SEQUENCE: 1

Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
        35                  40                  45

Lys Thr Leu Gly Ala Gly Ala Phe Gly Lys Val Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
                85                  90                  95

Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
```

```
                  115                 120                 125
Cys Cys Tyr Gly Asp Leu Leu Asn Phe Leu Arg Arg Lys Ala Glu Ala
        130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
        195                 200                 205

Asp Gly Arg Pro Leu Glu Leu Arg Asp Leu Leu His Phe Ser Ser Gln
    210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
        275                 280                 285

Ser Ile Phe Asp Cys Val Tyr Thr Val Gln Ser Asp Val Trp Ser Tyr
    290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
        355                 360                 365

Ile Cys Ser Phe Leu Gln Glu Gln Ala Gln Glu Asp Arg Arg Glu Arg
    370                 375                 380

Asp Tyr Thr Asn Leu Pro Ser Ser Ser Arg Ser Gly Gly Ser Gly Ser
385                 390                 395                 400

Ser Ser Ser Glu Leu Glu Glu Glu Ser Ser Ser Glu His Leu Thr Cys
                405                 410                 415

Cys Glu Gln Gly Asp Ile Ala Gln Pro Leu Leu Gln Pro Asn Asn Tyr
            420                 425                 430

Gln Phe Cys
        435

<210> SEQ ID NO 2
<211> LENGTH: 676
<212> TYPE: PRT
<213> ORGANISM: Artificial Sequence
<220> FEATURE:
<223> OTHER INFORMATION: uKit with N-terminal GST fusion

<400> SEQUENCE: 2

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
```

-continued

```
                35                  40                  45
Pro Asn Leu Pro Tyr Tyr Ile Asp Gly Asp Val Lys Leu Thr Gln Ser
 50                  55                  60

Met Ala Ile Ile Arg Tyr Ile Ala Asp Lys His Asn Met Leu Gly Gly
 65                  70                  75                  80

Cys Pro Lys Glu Arg Ala Glu Ile Ser Met Leu Glu Gly Ala Val Asp
                 85                  90                  95

Ile Arg Tyr Gly Val Ser Arg Ile Ala Tyr Ser Lys Asp Phe Glu Thr
                100                 105                 110

Leu Lys Val Asp Phe Leu Ser Lys Leu Pro Glu Met Leu Lys Met Phe
            115                 120                 125

Glu Asp Arg Leu Cys His Lys Thr Tyr Leu Asn Gly Asp His Val Thr
            130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
            195                 200                 205

His Pro Pro Lys Ser Asp Leu Val Pro Arg His Asn Gln Thr Ser Leu
210                 215                 220

Tyr Lys Lys Ala Gly Ser Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
            275                 280                 285

Leu Ser Phe Gly Lys Thr Leu Gly Ala Gly Ala Phe Gly Lys Val Val
290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
            340                 345                 350

Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430

Pro Thr Lys Ala Asp Lys Arg Arg Ser Val Arg Ile Gly Ser Tyr Ile
            435                 440                 445

Glu Arg Asp Val Thr Pro Ala Ile Met Glu Asp Asp Glu Leu Ala Leu
450                 455                 460
```

```
Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Leu Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Asp Val
        675

<210> SEQ ID NO 3
<211> LENGTH: 550
<212> TYPE: PRT
<213> ORGANISM: Homo sapiens

<400> SEQUENCE: 3

Gln Lys Lys Pro Arg Tyr Glu Ile Arg Trp Lys Val Ile Glu Ser Val
1               5                   10                  15

Ser Ser Asp Gly His Glu Tyr Ile Tyr Val Asp Pro Met Gln Leu Pro
                20                  25                  30

Tyr Asp Ser Thr Trp Glu Leu Pro Arg Asp Gln Leu Val Leu Gly Arg
            35                  40                  45

Thr Leu Gly Ser Gly Ala Phe Gly Gln Val Val Glu Ala Thr Ala His
        50                  55                  60

Gly Leu Ser His Ser Gln Ala Thr Met Lys Val Ala Val Lys Met Leu
65                  70                  75                  80

Lys Ser Thr Ala Arg Ser Ser Glu Lys Gln Ala Leu Met Ser Glu Leu
                85                  90                  95

Lys Ile Met Ser His Leu Gly Pro His Leu Asn Val Val Asn Leu Leu
            100                 105                 110

Gly Ala Cys Thr Lys Gly Gly Pro Ile Tyr Ile Ile Thr Glu Tyr Cys
        115                 120                 125

Arg Tyr Gly Asp Leu Val Asp Tyr Leu His Arg Asn Lys His Thr Phe
    130                 135                 140

Leu Gln His His Ser Asp Lys Arg Arg Pro Pro Ser Ala Glu Leu Tyr
```

-continued

```
            145                 150                 155                 160
        Ser Asn Ala Leu Pro Val Gly Leu Pro Leu Pro Ser His Val Ser Leu
                            165                 170                 175

Thr Gly Glu Ser Asp Gly Gly Tyr Met Asp Met Ser Lys Asp Glu Ser
                        180                 185                 190

Val Asp Tyr Val Pro Met Leu Asp Met Lys Gly Asp Val Lys Tyr Ala
                    195                 200                 205

Asp Ile Glu Ser Ser Asn Tyr Met Ala Pro Tyr Asp Asn Tyr Val Pro
                210                 215                 220

Ser Ala Pro Glu Arg Thr Cys Arg Ala Thr Leu Ile Asn Glu Ser Pro
        225                 230                 235                 240

Val Leu Ser Tyr Met Asp Leu Val Gly Phe Ser Tyr Gln Val Ala Asn
                        245                 250                 255

Gly Met Glu Phe Leu Ala Ser Lys Asn Cys Val His Arg Asp Leu Ala
                        260                 265                 270

Ala Arg Asn Val Leu Ile Cys Glu Gly Lys Leu Val Lys Ile Cys Asp
                    275                 280                 285

Phe Gly Leu Ala Arg Asp Ile Met Arg Asp Ser Asn Tyr Ile Ser Lys
                290                 295                 300

Gly Ser Thr Phe Leu Pro Leu Lys Trp Met Ala Pro Glu Ser Ile Phe
        305                 310                 315                 320

Asn Ser Leu Tyr Thr Thr Leu Ser Asp Val Trp Ser Phe Gly Ile Leu
                            325                 330                 335

Leu Trp Glu Ile Phe Thr Leu Gly Gly Thr Pro Tyr Pro Glu Leu Pro
                        340                 345                 350

Met Asn Glu Gln Phe Tyr Asn Ala Ile Lys Arg Gly Tyr Arg Met Ala
                        355                 360                 365

Gln Pro Ala His Ala Ser Asp Glu Ile Tyr Glu Ile Met Gln Lys Cys
                    370                 375                 380

Trp Glu Glu Lys Phe Glu Ile Arg Pro Pro Phe Ser Gln Leu Val Leu
        385                 390                 395                 400

Leu Leu Glu Arg Leu Leu Gly Glu Gly Tyr Lys Lys Lys Tyr Gln Gln
                            405                 410                 415

Val Asp Glu Glu Phe Leu Arg Ser Asp His Pro Ala Ile Leu Arg Ser
                        420                 425                 430

Gln Ala Arg Leu Pro Gly Phe His Gly Leu Arg Ser Pro Leu Asp Thr
                    435                 440                 445

Ser Ser Val Leu Tyr Thr Ala Val Gln Pro Asn Glu Gly Asp Asn Asp
                    450                 455                 460

Tyr Ile Ile Pro Leu Pro Asp Pro Lys Pro Glu Val Ala Asp Glu Gly
        465                 470                 475                 480

Pro Leu Glu Gly Ser Pro Ser Leu Ala Ser Ser Thr Leu Asn Glu Val
                        485                 490                 495

Asn Thr Ser Ser Thr Ile Ser Cys Asp Ser Pro Leu Glu Pro Gln Asp
                        500                 505                 510

Glu Pro Glu Pro Glu Pro Gln Leu Glu Leu Gln Val Glu Pro Glu Pro
                    515                 520                 525

Glu Leu Glu Gln Leu Pro Asp Ser Gly Cys Pro Ala Pro Arg Ala Glu
                    530                 535                 540

Ala Glu Asp Ser Phe Leu
        545                 550
```

2-AMINOPYRIMIDIN-6-ONES AND ANALOGS EXHIBITING ANTI-CANCER AND ANTI-PROLIFERATIVE ACTIVITIES

PRIORITY

This application claims the benefit of U.S. Provisional Application No. 61/792,812, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_062_01US_SeqList_ST25.txt, date recorded: Mar. 15, 2014, file size 18 kilobytes).

FIELD OF THE INVENTION

Disclosed are compounds which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

BACKGROUND

Autoimmune diseases, including autoimmune arthritis, represent significant human diseases of high morbidity and prevalence. Rheumatoid arthritis affects ~0.6% of the world population (Firestein, G. S., Nature (2003) 423: 356). While the adaptive immune response, involving generation of autoantibodies which react with tissue antigen, is involved in the etiology and initial propagation of these diseases (Edwards, J. C. et al, New England Journal of Medicine (2004) 350: 2572; Genovese, M. C. et al, New England Journal of Medicine (2005) 353: 1114), the chronic manifestations of tissue and joint damage are mediated in large part by cellular events mediated by the innate immune response (Firestein, G. S., Nature (2003) 423: 356; Paniagua, R. T. et al, Arthritis Research & Therapy (2010) 12: R32). Contributing cell types from the innate immune response which mediate chronic tissue damage include fibroblast-like synoviocytes, macrophages, mast cells, and osteoclasts.

Kinases represent a protein family that play critical roles in mammalian cell function, including cell proliferation, survival, motility, response to growth factors, and secretion of cytokines and other proinflammatory, proangiogenic, and immunomodulatory substances. Thus, elucidation of kinases which mediate these events in fibroblast-like synoviocytes, macrophages, mast cells, and osteoclasts represents a rational approach to new therapies for the treatment of autoimmune diseases.

Imatinib is a marketed kinase inhibitor for the treatment of the cancer chronic myelogenous leukemia (CML, Druker, B. J. et al, New England Journal of Medicine (2001) 344: 1031) and for the treatment of gastrointestinal stromal tumors (GIST, Demetri, G. D., et al, New England Journal of Medicine (2002) 347: 472). Imatinib has also shown benefit in cancer patients co-presenting with autoimmune diseases such as rheumatoid arthritis (Ihara, M. K. et al, Clinical Rheumatology (2003) 22: 362; Eklund, K. K. and Joensuu, H., Ann Medicine (2003) 35: 362; Ames, P. R. et al, Journal of Rheumatology (2008) 35: 1682). The kinases inhibited by imatinib which confer its efficacy in the treatment of CML and GIST are BCR-ABL kinase and c-KIT kinase, respectively. Beyond these two kinases, other kinases inhibited by imatinib include c-FMS, PDGFR-alpha, and PDGFR-beta (Dewer, A. L. et al, Blood (2005) 105: 3127; Fabian, M. A. et al, Nature Biotechnology (2005) 23: 329.

Recent research disclosures have identified c-FMS kinase to be associated with activation of synovial macrophages, PDGFR kinase to be associated with activation of fibroblast-like synoviocytes, and c-KIT kinase to be associated with activation of mast cells (Paniagua, R. T., et al Journal of Clinical Investigation (2006) 116: 2633). c-FMS kinase has also been associated with the proliferation and differentiation of monocytes into macrophages and osteoclasts, which are recruited to mediate joint damage in rheumatoid arthritis (Paniagua, R. T. et al, Arthritis Research & Therapy (2010) 12: R32; Yao, Z. et al, Journal of Biological Chemistry (2006) 281: 11846; Patel, S, and Player, M. R. Current Topics in Medicinal Chemistry (2009) 9: 599; Pixley, F. J. et al, Trends in Cell Biology (2004) 14: 628).

In recent years, the importance of the tumor microenvironment in cancer motility, invasion, and metastasis has become more clearly defined. Specifically, the role of tumor-associated macrophages (TAMs) in tumor progression has been studied. These host (stromal) macrophages are recruited to tumor sites or to pre-metastatic niches to modify the tumor environment and render that environment more conducive to tumor motility, invasion and metastasis. These TAMs are known to express c-FMS receptor tyrosine kinase (also known as CSF-1R) on their surfaces and to rely on signaling through this kinase by binding to the activating ligands CSF-1 (also known as macrophage colony stimulating factor, or MCSF) and interleukin-34 (IL-34). Activation of this c-FMS/MCSF (CSF1-R/CSF-1) signaling axis stimulates monocyte proliferation, differentiation into tumor associated macrophages, and promotion of macrophage cell survival. By stimulating the TAM component of the tumor microenvironment, c-FMS kinase activation is associated with tumor cell migration, invasion, and metastasis (J. Condeelis and J. W. Pollard, Cell (2006) 124: 263; S. Patel and M. R. Player, Current Topics in Medicinal Chemistry (2009) 9: 599). Ablation of CSF-1, the ligand for c-FMS kinase, in mice reduced tumor progression and significantly reduced metastasis in a murine model of breast cancer; whereas overexpression of CSF-1 accelerated metastasis in this model (E. Y. Lin et al, Journal of Experimental Medicine (2001) 193: 727). Furthermore, an interaction between tumor cells and macrophages has been described, wherein macrophage secretion of the tumor growth factor EGF and tumor cell secretion of CSF-1 establish a paracrine loop that promotes tumor migration and invasiveness. This paracrine loop was blocked by administration of an antibody to the c-FMS kinase (J. Wyckoff et al, Cancer Research (2004) 64: 7022). Correlative clinical data have also shown that overexpression of CSF-1 in tumors is a predictor of poor prognosis (R. D. Leek and A. L. Harris, Journal of Mammary Gland Biology Neoplasia (2002) 7: 177; E. Y. Lin et al, Journal of Mammary Gland Biology Neoplasia (2002) 7: 147). c-FMS kinase activation is also required for osteoclast differentiation and activation. Its involvement in mediating bone metastases of various cancers, including breast and prostate cancers, has been reported (S. Patel and M. R. Player, Current Topics in Medicinal Chemistry (2009) 9: 599). High plasma concentrations of CSF-1 have been reported in bone metastatic prostate cancer, implicating activation of osteoclast c-FMS kinase in prostate cancer bone metastases (H. Ide, et al, Human Cell (2008) 21:1). c-FMS inhibitors have been reported to reduce radiographic bone lesions when evaluated in models of metastatic bone disease (C. L. Manthey, et al, Molecular Cancer Therapy (2009) 8: 3151; H. Ohno et al, Mol. Cancer. Therapy (2006) 8: 2634). MCSF-mediated activation of both LYVE-1+ and LYVE1- macrophages also mediates pathological angiogenesis and lymphangiogenesis in murine models of cancer, and blockade of c-FMS signaling resulted in suppression of tumor angiogenesis/lymphangiogenesis (Y. Kubota et al., Journal of Experimental Medicine (2009) 206: 1089). Administration of a CSF-1R inhibitor blocked the recruitment of bone marrow derived TAMs and also bone marrow derived monocytic myeloid-derived suppressor cells (MDSCs) to tumor sites; this blockade led to a significant decrease in tumor angiogenesis and when combined with anti-VEGFR-2 therapy synergistically suppressed tumor growth (S. J. Priceman, et al. Blood (2010) 115: 1461). Irradiation of glioblastoma tumors in mice was shown to cause a temporary decrease in tumor size only to be followed by a rebound tumor vasculogenesis mediated by the recruitment of bone marrow derived monocytes expressing CD11b and F4/80 surface antigens (M. Kioi et al, Journal of Clinical Investigation (2010) 120: 694). CD11b+ and F4/80+ monocytes are also known to express functional c-FMS receptors. Hence, blockade of tumor infiltrating c-FMS+ bone marrow derived monocytes by the use of c-FMS kinase inhibitors offers the potential to prevent tumor rebound vasculogenesis and glioblastoma tumor progression. CSF-1R blockade has also been shown to reverse immunotolerance mechanisms in an immunocompetent murine breast cancer model and promote the appearance of anti-tumor immune programs by upregulating CD8+ T-cell-mediated tumor suppression. Restoration of an anti-tumor immune program was mechanistically linked to c-FMS inhibitor blockade of TAM-mediated Programmed Death Ligand-1 (PDL-1) immunotolerance (D. G. DeNardo, et al. Cancer Discovery (2011) 1: OF52).

Hence, small molecule inhibitors of c-FMS kinase, c-KIT kinase, or PDGFR kinases provide a rational approach to new therapies for the treatment of autoimmune diseases, and to particularly block the chronic tissue destruction mediated by the innate immune system. Inhibition of c-FMS kinase also provides a rational approach to new therapies for the treatment of cancers, especially for the treatment of cancer invasiveness, cancer angiogenesis or vasculogenesis, cancer metastasis, cancer immunotolerance, and for the treatment of cancers prone to bone metastases.

There is a need to provide kinase inhibitors which selectively inhibit kinases causative of the chronic tissue destruction in autoimmune disease (c-FMS, c-KIT, PDGFR), without inhibiting other kinases targeted by marketed cancer therapeutics (ABL, BCR-ABL, KDR, SRC, LCK, LYN, FGFR and other kinases). The present invention discloses novel inhibitors that inhibit c-FMS, c-KIT, and/or PDGFR kinases for the treatment of autoimmune diseases which also exhibit selectivity by not potently inhibiting other kinases including ABL, BCR-ABL, KDR, SRC, LCK, LYN, FGFR, MET and other kinases. The inhibitors of the present invention also find utility in the treatment of other mammalian diseases, including human diseases, mediated by c-FMS, c-KIT, or PDGFR kinases. Such diseases include, without limitation, cancers, autoimmune diseases, and bone resorptive diseases.

SUMMARY OF THE INVENTION

In one aspect, compounds of the Formula I are described:

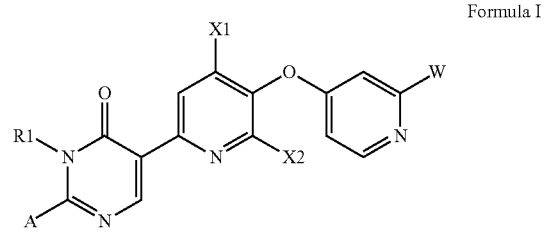

Formula I and pharmaceutically acceptable salts, enantiomers, stereoisomers, and tautomers thereof,
wherein
A is taken from the group consisting of —N(R2)R3 and G;
G is selected from the group consisting of

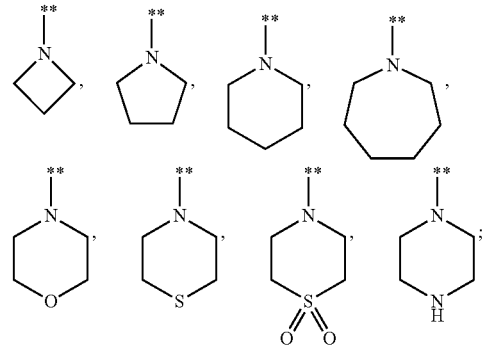

and wherein the symbol (**) is the point of attachment to the pyrimidine ring;
each G moiety may be further substituted with one, two, or three R4 moieties;
W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties;
X1 and X2 are individually and independently hydrogen or C1-C6 alkyl;
R1 is hydrogen, C1-C6 alkyl, deutero-C1-C6 alkyl wherein the alkyl chain is partially or completely deuterated, or branched C3-C8 alkyl;
R2 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated, —(CH$_2$)$_m$—OR8, or a 3-8 membered heterocyclic ring, wherein each alkylene is optionally substituted with C1-C4 alkyl;
R3 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated or a 3-8 membered heterocyclic ring;
each R4 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, —(CH$_2$)$_m$—OR8, —(CH$_2$)$_m$—NR8(R9), —(CH$_2$)$_m$—R7, or cyano, wherein each alkylene is optionally substituted with C1-C4 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —$(CH_2)_m$—C(O)NR8 (R9), —$(CH_2)_m$—C(O)R7, —$(CH_2)_m$—OR8, —$(CH_2)_m$—NR8(R9), or —$(CH_2)_m$—R7, wherein each alkylene is optionally substituted with C1-C4 alkyl;

each R6 is individually and independently hydrogen, C1-C6 alkyl, branched C3-C8 alkyl, C3-C8 cycloalkyl, —$(CH_2)_m$—CN, —$(CH_2)_m$—OR8, —$(CH_2)_m$—NR8(R9), or —$(CH_2)_m$—R7, wherein each alkylene is optionally substituted with C1-C4 alkyl;

each R7 is independently and individually selected from the group consisting of and wherein the symbol (##) is the point of attachment to respective W, R5 or R6 moieties containing a R7 moiety;

each R7 is optionally substituted with —$(R10)_p$;

each R8 and R9 is individually and independently hydrogen, C1-C6 alkyl, fluoro-C1-C6 alkyl wherein the alkyl chain is partially or completely fluorinated, or branched C3-C8 alkyl;

each R10 is individually and independently C1-C6 alkyl, —$(CH_2)_m$—CN, —$(CH_2)_m$—OR3, —$(CH_2)_m$—NR8(R9), or —$(CH_2)_m$—C(O)—R6, wherein each alkyl or alkylene is optionally substituted with one or two C1-C6 alkyl;

wherein each alkylene is optionally substituted with C1-C4 alkyl each m is individually and independently 0, 1, 2, or 3; and each p is 0, 1, 2, or 3.

In one embodiment of Formula I, A is —N(R2)R3.

In one embodiment of Formula I, A is G.

In one embodiment of Formula I, W is C5-C6heteroaryl optionally substituted by one, two, or three R5.

In one embodiment of Formula I, W is —NHC(O)R6, —NHC(O)R7, or —NHC(O)N(R8)R9.

In one embodiment of Formula I, W is —NHC(O)R6.

In one embodiment of Formula I, W is —NHC(O)R7.

In one embodiment of Formula I, W is —NHC(O)N(R8)R9.

In one embodiment of Formula I, W is —C(O)N(R8)R9.

In one embodiment of Formula I, W is phenyl optionally substituted by one, two, or three R5.

In one embodiment of Formula I, X1 and X2 are individually and independently hydrogen or C1-C6 alkyl.

In one embodiment of Formula I, X1 and X2 are hydrogen.

In one embodiment of Formula I, one of X1 and X2 is hydrogen and the other is C1-C6alkyl.

In one embodiment of Formula I, R1 is hydrogen, C1-C6 alkyl, deutero-C1-C6 alkyl wherein the alkyl chain is partially or completely deuterated, or branched C3-C8 alkyl.

In one embodiment of Formula I, R1 is hydrogen.

In one embodiment of Formula I, R1 is C1-C6alkyl.

In one embodiment, the compound of Formula I is a compound of Formula Ia wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof.

Formula Ia

In one embodiment of Formula Ia, W is C5-C6heteroaryl optionally substituted by one, two, or three R5.

In one embodiment of Formula Ia, W is pyrazolyl, imidazolyl, isoxazolyl, oxazolyl, thiazolyl, triazolyl, or pyridinyl and wherein each W is optionally substituted by one, two, or three R5.

In one embodiment of Formula Ia, W is pyrazolyl optionally substituted by one, two, or three R5.

In one embodiment of Formula Ia, W is imidazolyl optionally substituted by one, two, or three R5.

In one embodiment of Formula Ia, W is isoxazolyl optionally substituted by one or two R5.

In one embodiment of Formula Ia, W is oxazolyl optionally substituted by one or two R5.

In one embodiment of Formula Ia, W is thiazolyl optionally substituted by one or two R5.

In one embodiment of Formula Ia, W is triazolyl optionally substituted by one or two R5.

In one embodiment of Formula Ia, W is pyridinyl optionally substituted by one, two, or three R5.

In one embodiment of Formula Ia, W is —NHC(O)R6, —NHC(O)R7, or —NHC(O)N(R8)R9.

In one embodiment of Formula Ia, W is —NHC(O)R6.

In one embodiment of Formula Ia, W is —NHC(O)R7.

In one embodiment of Formula Ia, W is —NHC(O)N(R8) R9.

In one embodiment of Formula Ia, W is —C(O)N(R8)R9.

In one embodiment of Formula Ia, W is phenyl optionally substituted by one, two, or three R5.

In one embodiment of Formula Ia, X1 and X2 are individually and independently hydrogen or C1-C6 alkyl.

In one embodiment of Formula Ia, X1 and X2 are hydrogen.

In one embodiment of Formula Ia, one of X1 and X2 is hydrogen and the other is C1-C6alkyl.

In one embodiment of Formula Ia, R1 is hydrogen, C1-C6 alkyl, deutero-C1-C6 alkyl wherein the alkyl chain is partially or completely deuterated, or branched C3-C8 alkyl.

In one embodiment of Formula Ia, R1 is hydrogen.

In one embodiment of Formula Ia, R1 is C1-C6alkyl.

In one embodiment of Formula Ia, R2 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated, —(CH$_2$)$_m$—OR8, or a 3-8 membered heterocyclic ring, wherein each alkylene is optionally substituted with C1-C4 alkyl.

In one embodiment of Formula Ia, R2 is C1-C6 alkyl, branched C3-C8 alkyl, C3-C8 cycloalkyl, —(CH$_2$)$_m$—OR8, or a 3-8 membered heterocyclic ring, wherein each alkylene is optionally substituted with C1-C4 alkyl.

In one embodiment of Formula Ia, R2 is C1-C6 alkyl.

In one embodiment of Formula Ia, R2 is branched C3-C8 alkyl.

In one embodiment of Formula Ia, R2 is C3-C8 cycloalkyl.

In one embodiment of Formula Ia, R2 is —(CH$_2$)$_m$—OR8, wherein each alkylene is optionally substituted with C1-C4 alkyl.

In one embodiment of Formula Ia, R2 is a 3-8 membered heterocyclic ring.

In one embodiment of Formula Ia, R3 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated or a 3-8 membered heterocyclic ring.

In one embodiment of Formula Ia, R3 is hydrogen.

In one embodiment of Formula Ia, R3 is C1-C6 alkyl.

In one embodiment of Formula Ia, R1 is hydrogen, R2 is C1-C6alkyl, branched C3-C8 alkyl or C3-C8 cycloalkyl, and R3 is hydrogen.

In one embodiment of Formula Ia, R1 is C1-C6alkyl, R2 is C1-C6alkyl, branched C3-C8 alkyl or C3-C8 cycloalkyl and R3 is hydrogen.

In one embodiment of Formula Ia, R1 is methyl, R2 is C1-C6alkyl, branched C3-C8 alkyl or C3-C8 cycloalkyl, and R3 is hydrogen.

In one embodiment, the compound of Formula I is a compound of Formula Ib wherein: X1 and X2 are individually and independently hydrogen or C1-C6 alkyl; or a pharmaceutically acceptable salt, enantiomer, stereoisomer, or tautomer thereof.

Formula Ib

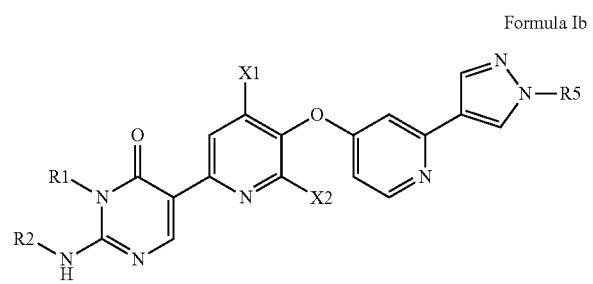

In one embodiment of Formula Ib, X1 and X2 are hydrogen.

In one embodiment of Formula Ib, one of X1 and X2 is hydrogen and the other is C1-C6alkyl.

In one embodiment of Formula Ib, R1 is hydrogen, C1-C6 alkyl, deutero-C1-C6 alkyl wherein the alkyl chain is partially or completely deuterated, or branched C3-C8 alkyl.

In one embodiment of Formula Ib, R1 is hydrogen.

In one embodiment of Formula Ib, R1 is C1-C6alkyl.

In one embodiment of Formula Ib, R2 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated, —(CH$_2$)$_m$—OR8, or a 3-8 membered heterocyclic ring, wherein each alkylene is optionally substituted with C1-C4 alkyl.

In one embodiment of Formula Ib, R2 is C1-C6 alkyl, branched C3-C8 alkyl, C3-C8 cycloalkyl, —(CH$_2$)$_m$—OR8, or a 3-8 membered heterocyclic ring, wherein each alkylene is optionally substituted with C1-C4 alkyl.

In one embodiment of Formula Ib, R2 is C1-C6 alkyl.

In one embodiment of Formula Ib, R2 is branched C3-C8 alkyl.

In one embodiment of Formula Ib, R2 is C3-C8 cycloalkyl.

In one embodiment of Formula Ib, R2 is —(CH$_2$)$_m$—OR8, wherein each alkylene is optionally substituted with C1-C4 alkyl.

In one embodiment of Formula Ib, R2 is a 3-8 membered heterocyclic ring.

In one embodiment of Formula Ib, R1 is hydrogen, and R2 is C1-C6alkyl, branched C3-C8 alkyl or C3-C8 cycloalkyl.

In one embodiment of Formula Ib, R1 is C1-C6alkyl, and R2 is C1-C6alkyl, branched C3-C8 alkyl or C3-C8 cycloalkyl.

In one embodiment of Formula Ib, R1 is methyl, and R2 is C1-C6alkyl, branched C3-C8 alkyl or C3-C8 cycloalkyl.

In one embodiment of Formula Ib, R5 is hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8 (R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl.

In one embodiment of Formula Ib, R5 is hydrogen, C1-C6 alkyl, or deutero-C1-C6 alkyl wherein the alkyl chain is partially or completely deuterated, or branched C3-C8 alkyl.

In one embodiment of Formula Ib, R5 is C1-C6 alkyl, or deutero-C1-C6 alkyl wherein the alkyl chain is partially or completely deuterated.

In one embodiment of Formula Ib, R5 is C1-C6 alkyl.

In one embodiment, the compound of Formula I is a compound of Formula Ic wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof.

Formula Ic

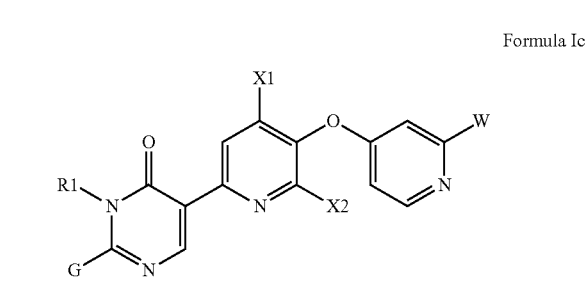

In one embodiment of Formula Ic, W is C5-C6heteroaryl optionally substituted by one, two, or three R5.

In one embodiment of Formula Ic, W is pyrazolyl, imidazolyl, isoxazolyl, oxazolyl, thiazolyl, triazolyl, or pyridinyl and wherein each W is optionally substituted by one, two, or three R5.

In one embodiment of Formula Ic, W is pyrazolyl optionally substituted by one, two, or three R5.

In one embodiment of Formula Ic, W is imidazolyl optionally substituted by one, two, or three R5.

In one embodiment of Formula Ic, W is isoxazolyl optionally substituted by one or two R5.

In one embodiment of Formula Ic, W is oxazolyl optionally substituted by one or two R5.

In one embodiment of Formula Ic, W is thiazolyl optionally substituted by one or two R5.

In one embodiment of Formula Ic, W is triazolyl optionally substituted by one or two R5.

In one embodiment of Formula Ic, W is pyridinyl optionally substituted by one, two, or three R5.

In one embodiment of Formula Ic, W is —NHC(O)R6, —NHC(O)R7, or —NHC(O)N(R8)R9.

In one embodiment of Formula Ic, W is —NHC(O)R6.

In one embodiment of Formula Ic, W is —NHC(O)R7.

In one embodiment of Formula Ic, W is —NHC(O)N(R8)R9.

In one embodiment of Formula Ic, W is —C(O)N(R8)R9.

In one embodiment of Formula Ic, W is phenyl optionally substituted by one, two, or three R5.

In one embodiment of Formula Ic, X1 and X2 are individually and independently hydrogen or C1-C6 alkyl.

In one embodiment of Formula Ic, X1 and X2 are hydrogen.

In one embodiment of Formula Ic, one of X1 and X2 is hydrogen and the other is C1-C6alkyl.

In one embodiment of Formula Ic, R1 is hydrogen, C1-C6 alkyl, deutero-C1-C6 alkyl wherein the alkyl chain is partially or completely deuterated, or branched C3-C8 alkyl.

In one embodiment of Formula Ic, R1 is hydrogen.

In one embodiment of Formula Ic, R1 is C1-C6alkyl.

In one embodiment of Formula Ic, G is selected from the group consisting of wherein the symbol (**) is the point of attachment to the pyrimidine ring;
and wherein each G moiety may be further substituted with one, two, or three R4 moieties.

In one embodiment of Formula Ic, R1 is hydrogen and G is selected from the group consisting of wherein the symbol (**) is the point of attachment to the pyrimidine ring;
and wherein each G moiety may be further substituted with one, two, or three R4 moieties.

In one embodiment of Formula Ic, R1 is C1-C6alkyl and G is selected from the group consisting of wherein the symbol (**) is the point of attachment to the pyrimidine ring;
and wherein each G moiety may be further substituted with one, two, or three R4 moieties.

In one embodiment of Formula Ic, R1 is methyl and G is selected from the group consisting of wherein the symbol (**) is the point of attachment to the pyrimidine ring;
and wherein each G moiety may be further substituted with one, two, or three R4 moieties.

In one embodiment, the compound of Formula I is a compound of Formula Id wherein: X1 and X2 are individually and independently hydrogen or C1-C6 alkyl; or a pharmaceutically acceptable salt, enantiomer, stereoisomer, or tautomer thereof.

Formula Id

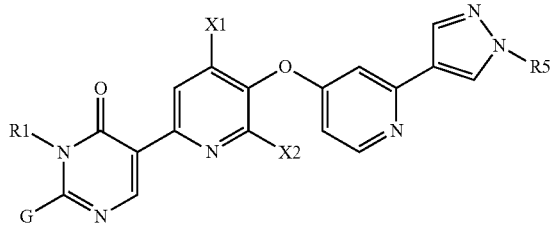

In one embodiment, the compound of Formula Id is a compound wherein: X1 and X2 are hydrogen.

In one embodiment, the compound of Formula Id is a compound wherein: one of X1 and X2 is hydrogen and the other is C1-C6alkyl.

In one embodiment, the compound of Formula Id is a compound wherein: R1 is hydrogen, C1-C6 alkyl, deutero-C1-C6 alkyl wherein the alkyl chain is partially or completely deuterated, or branched C3-C8 alkyl.

In one embodiment, the compound of Formula Id is a compound wherein: R1 is hydrogen.

In one embodiment, the compound of Formula Id is a compound wherein: R1 is C1-C6alkyl.

In one embodiment, the compound of Formula Id is a compound wherein: G is selected from the group consisting of

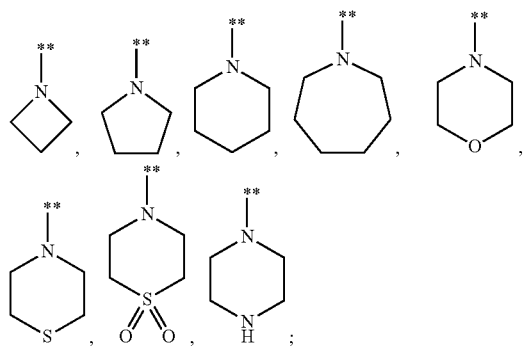

wherein the symbol (**) is the point of attachment to the pyrimidine ring;
and wherein each G moiety may be further substituted with one, two, or three R4 moieties.

In one embodiment, the compound of Formula Id is a compound wherein: R1 is hydrogen and G is selected from the group consisting of

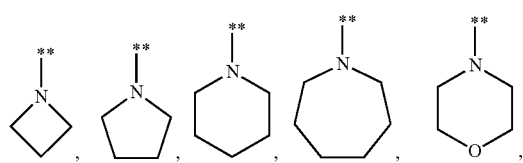

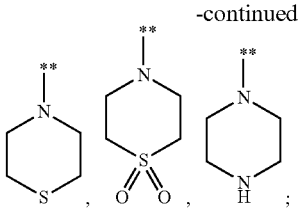

wherein the symbol (**) is the point of attachment to the pyrimidine ring;
and wherein each G moiety may be further substituted with one, two, or three R4 moieties.

In one embodiment, the compound of Formula Id is a compound wherein: R1 is C1-C6alkyl and G is selected from the group consisting of

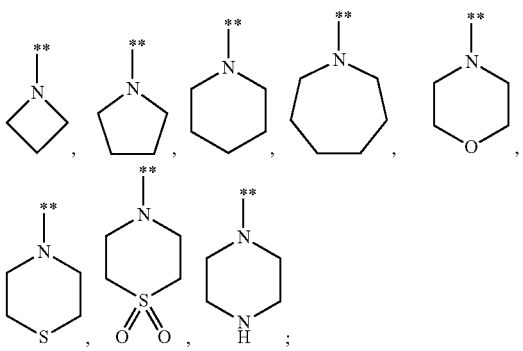

wherein the symbol (**) is the point of attachment to the pyrimidine ring;
and wherein each G moiety may be further substituted with one, two, or three R4 moieties.

In one embodiment, the compound of Formula Id is a compound wherein: R1 is methyl and G is selected from the group consisting of

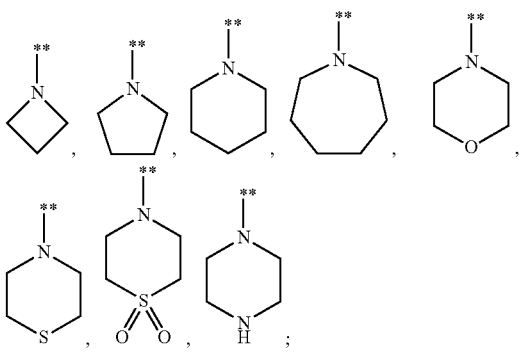

wherein the symbol (**) is the point of attachment to the pyrimidine ring;
and wherein each G moiety may be further substituted with one, two, or three R4 moieties.

In one embodiment, the compound of Formula Id is a compound wherein: R5 is hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH2)m-C(O)NR8(R9), —(CH2)m-C(O)R7, —(CH2)m-OR8, —(CH2)m-NR8(R9), or —(CH2)m-R7, wherein each alkylene is optionally substituted with C1-C4 alkyl.

In one embodiment, the compound of Formula Id is a compound wherein: R5 is hydrogen, C1-C6 alkyl, or deutero-C1-C6 alkyl wherein the alkyl chain is partially or completely deuterated, or branched C3-C8 alkyl.

In one embodiment, the compound of Formula Id is a compound wherein: R5 is C1-C6 alkyl, or deutero-C1-C6 alkyl wherein the alkyl chain is partially or completely deuterated.

In one embodiment, the compound of Formula Id is a compound wherein: R5 is C1-C6 alkyl.

In some embodiments, the invention comprises a compound selected from the group consisting of 2-(ethylamino)-5-(6-methyl-5-((2-(1-methyl-1H-pyrazol-4-yl)pyridin-4-yl)oxy)pyridin-2-yl)pyrimidin-4(3H)-one, 2-(dimethylamino)-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(6-methyl-5-((2-(1-methyl-1H-pyrazol-4-yl)pyridin-4-yl)oxy)pyridin-2-yl)pyrimidin-4(3H)-one, 2-(ethylamino)-5-(6-methyl-5-((6'-methyl-[2,3'-bipyridin]-4-yl)oxy)pyridin-2-yl)pyrimidin-4(3H)-one, 2-(ethylamino)-5-(6-methyl-5-((2-(4-methyl-1H-imidazol-1-yl)pyridin-4-yl)oxy)pyridin-2-yl)pyrimidin-4(3H)-one, 2-((2-methoxyethyl)amino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(methylamino)pyrimidin-4(3H)-one, 2-(ethylamino)-5-(5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one, 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one, 4-((6-(2-(isopropylamino)-6-oxo-1,6-dihydropyrimidin-5-yl)pyridin-3-yl)oxy)-N-methylpicolinamide, 5-(6-methyl-5-((2-(1-methyl-1H-pyrazol-4-yl)pyridin-4-yl)oxy)pyridin-2-yl)-2-morpholinopyrimidin-4(3H)-one, 5-(6-methyl-5-((2-(1-methyl-1H-pyrazol-4-yl)pyridin-4-yl)oxy)pyridin-2-yl)-2-(piperidin-1-yl)pyrimidin-4(3H)-one, 2-(cyclopropylamino)-5-(6-methyl-5-((2-(1-methyl-1H-pyrazol-4-yl)pyridin-4-yl)oxy)pyridin-2-yl)pyrimidin-4(3H)-one, 2-(cyclopentylamino)-5-(6-methyl-5-((2-(1-methyl-1H-pyrazol-4-yl)pyridin-4-yl)oxy)pyridin-2-yl)pyrimidin-4(3H)-one, 3-methyl-5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one, 2-(cyclopropylamino)-3-methyl-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(4-methyl-5-((2-(1-methyl-1H-pyrazol-4-yl)pyridin-4-yl)oxy)pyridin-2-yl)pyrimidin-4(3H)-one, N-(4-((6-(2-(isopropylamino)-6-oxo-1,6-dihydropyrimidin-5-yl)-2-methylpyridin-3-yl)oxy)pyridin-2-yl)acetamide, 5-(4-methyl-5-((2-(1-methyl-1H-pyrazol-4-yl)pyridin-4-yl)oxy)pyridin-2-yl)-2-(pyrrolidin-1-yl)pyrimidin-4(3H)-one, 5-(5-((2-(1-ethyl-1H-pyrazol-4-yl)pyridin-4-yl)oxy)-6-methylpyridin-2-yl)-2-(isopropylamino)pyrimidin-4(3H)-one, (R)-2-((1-methoxypropan-2-yl)amino)-5-(6-methyl-5-((2-(1-methyl-1H-pyrazol-4-yl)pyridin-4-yl)oxy)pyridin-2-yl)pyrimidin-4(3H)-one, (R)-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidin-4(3H)-one, (S)-2-(3-(dimethylamino)pyrrolidin-1-yl)-5-(6-methyl-5-((2-(1-methyl-1H-pyrazol-4-yl)pyridin-4-yl)oxy)pyridin-2-yl)pyrimidin-4(3H)-one, 2-(ethylamino)-3-methyl-5-(6-methyl-5-((2-(1-methyl-1H-pyrazol-4-yl)pyridin-4-yl)oxy)pyridin-2-yl)pyrimidin-4(3H)-one, 2-((2-methoxyethyl)amino)-3-methyl-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-((tetrahydro-2H-pyran-4-yl)amino)pyrimidin-4(3H)-one, 2-(tert-butylamino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(neopentylamino)pyrimidin-4(3H)-one, and 2-(3,3-difluoropyrrolidin-1-yl)-5-(6-methyl-5-((2-(1-methyl-1H-pyrazol-4-yl)pyridin-4-yl)oxy)pyridin-2-yl)pyrimidin-4(3H)-one.

In certain embodiments, the invention comprises a method of treating mammalian disease at least partially mediated by the kinase activity of c-FMS, PDGFR-β, or c-KIT kinases, wherein the kinase is a wildtype form, a mutant oncogenic form, an aberrant fusion protein form or a polymorph thereof, the method comprising administering to a mammal in need thereof an effective amount of a compound of formula I.

In other embodiments, the present invention comprises a pharmaceutical composition, comprising a compound of formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention includes a method of treating glioblastomas, breast cancers, pancreatic cancers, metastasis of primary tumor sites, or cancers that are metastatic to bone, the method comprising administering to a patient in need thereof an effective amount of a compound of formula I.

In certain embodiments of the present methods, the compound is administered orally, parenterally, by inhalation, or subcutaneously.

In some embodiments, the invention provides the use of a compound of Formula I, or a pharmaceutically acceptable salt thereof, in the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention provides the use of a compound of Formula I, or a pharmaceutically acceptable salt thereof, in the treatment of glioblastomas, breast cancers, pancreatic cancers, metastasis of primary tumor sites, or cancers that are metastatic to bone, the method comprising administering to a patient in need thereof an effective amount of a compound of formula I.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia.

In certain embodiments, the invention provides for the use of a compound of Formula I, or a pharmaceutically acceptable salt thereof, for the manufacture of a medicament for the treatment of glioblastomas, breast cancers, pancreatic cancers, metastasis of primary tumor sites, or cancers that are metastatic to bone.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts. Thus, the terms "compound", "compounds", "test compound" or "test compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl, 2-pentyl, 3-pentyl, 2-hexyl, and 3-hexyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH$_2$—, —CH$_2$CH$_2$—, and —CH$_2$CH$_2$CH$_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized ρ electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands through which the heterocyclyl ring is connected to an adjacent moiety. For example, in some embodiments, a ring N atom from the heterocyclyl is the bonding atom of the heterocylic moiety. In exemplary embodiments, "heterocyclyl" refers to a monocyclic hydrocarbon containing 4, 5, 6, 7 or 8 ring atoms (i.e., C4-C8 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized ρ electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, feline, horse, cow, pig, monkey, chimpanzee, baboon, or rhesus monkey.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The compounds of Formula I, or pharmaceutically acceptable salts thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5th Edition, Michael B. Smith and Jerry March, Wiley Interscience, 2001; Advanced Organic Chemistry, 4th Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate "conc." is concentrated, "DBU" is 1,8-diazabicyclo [5.4.0]undec-7-ene, "DCE" is 1,2-dichloroethane, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphryl azide, "ESI" is electrospray ionization, "$Et_2O$" is diethylether, "EtOAc" is ethyl acetate, "EtOH" is ethanol, "GST" is glutathione S-transferase, "h" is hour or hours, "Hex" is hexane, "$IC_{50}$" is half maximal inhibitory concentration, "LiMHDS" is lithium bis (trimethylsilyl)amide, "mCPBA" is 3-chloroperbenzoic acid, "MeCN" is acetonitrile, "MeOH" is methanol, "$Me_4tBuXPhos$" is di-tert-butyl(2',4',6'-triisopropyl-3,4,5,6-tetramethyl-[1,1'-biphenyl]-2-yl)phosphine, "MHz" is megahertz, "min" is minute or minutes, "MS" is mass spectrometry, "MTBE" is methyl tert-butyl ether, "NADH" is nicotinamide adenine dinucleotide, "NBS" is N-bromosuccinimide, "NMR" is nuclear magnetic resonance, "PBS" is phosphate buffered saline, "Pd/C" is palladium on carbon, "$Pd_2(dba)_3$" is tris(dibenzylideneacetone)dipalladium(0), "$Pd(PPh_3)_4$" is tetrakis(triphenylphosphine)palladium (0), "prep-HPLC" is preparative high performance liquid chromatography, "RT" is room temperature which is also known as "ambient temp," which will be understood to consist of a range of normal laboratory temperatures ranging from 15-25° C., "satd." is saturated, "TEA" is triethylamine, "TFA" is trifluoroacetic acid, "THF" is tetrahydrofuran, "Tris" is tris (hydroxymethyl)aminomethane, "Xantphos" is 4,5-bis (diphenylphosphino)-9,9-dimethylxanthene, and "X-Phos" is 2-dicyclohexylphosphino-2',4',6'-triisopropylbiphenyl.

General Chemistry

The compounds of Formula I are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula 1 is dependent upon the particular compound being synthesized, the starting compound, and the relative lability of the substituted moieties, as is well appreciated by the ordinary skilled chemist. All substituents, unless otherwise indicated, are as defined above.

The compounds of Formula I may contain —NH or —OH moieties in the W and A positions. It will be understood by those skilled in the art that in some instances it may be advantageous to use an amine protecting group during synthesis to temporarily mask one or more —NH or —OH moieties. Said protecting group can be removed from any subsequent intermediate of the synthetic sequence, using standard conditions that effect removal of said protecting group, said conditions of which will be familiar to those skilled in the art. When not specified in a scheme, it will be understood by those skilled in the art that the W and A moieties represented in the schemes below may optionally contain standard amino or hydroxyl protecting groups that can be removed at any opportune time in the synthetic sequence.

Compounds 1 (Formula I wherein R1 is H) of the invention can be prepared as illustrated in Scheme 1. In one embodiment, the di-pyridine 2 can react with boronate 3 or boronic acid 4 to provide intermediate 5. The reaction of 2 with 3 or 4 is generally performed in the presence of a palladium catalyst, for example for example Pd(PPh$_3$)$_4$, and a base, for example potassium carbonate with heating. Further conversion of 5 to 7 is effected by reaction of 5 with reagent M-W (6), wherein M is trialkylstanyl or a boronic acid or boronate ester (when W is heteroaryl), or alternately wherein M is H (when W is —NHC(O)R6, —NHC(O)R7, —NHC(O)N(R8)R9. Conditions for the transformation of 5 to 7 are dependent on the nature of the W-moiety, but generally include the use of palladium catalysts, for example Pd(PPh$_3$)$_4$ or Pd$_2$(dba)$_3$, optionally in the presence of additional ligands, for example Xantphos. General conditions to accomplish these transformations are well known to those skilled in the art and are further illustrated in the accompanying examples. Finally, cleavage of the methyl ether of 7, for example by treatment with HBr or trimethylsilyl iodide, provides compounds of formula 1 wherein R1 is H.

In another embodiment of Scheme 1, compound 7 can be prepared directly from 8 (Z is bromo or iodo) by reaction with 3 or 4.

In another embodiment of Scheme 1, intermediate 7 can be prepared from 2 by a sequence commencing with the reaction of 2 with 9 or 10 to provide 11. Reaction of 11 with M-W (6) as described above provides 12. In another embodiment, reaction of 8 with 9 or 10 affords 12 directly. Reaction of 12 with amine A-H 13 provides 7. In one embodiment, the conversion of 12 to 7 is accomplished by sequential treatment with an oxidant, such as m-chloroperoxybenzoic acid, to effect the oxidation of the thiomethyl moiety of 12 to a methylsulfoxide or methylsulfone intermediate followed by treatment of said intermediate with A-H 13.

Scheme 1

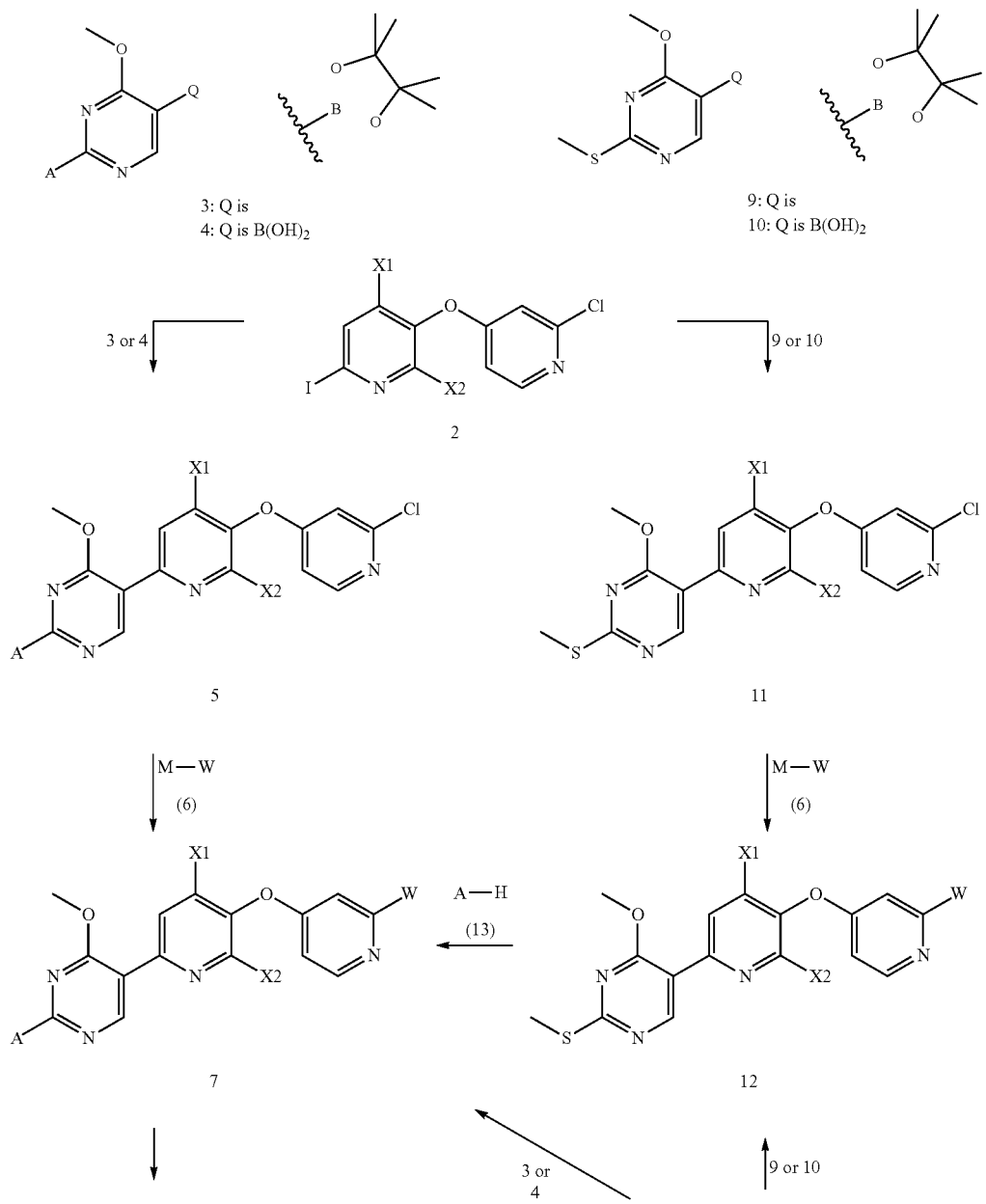

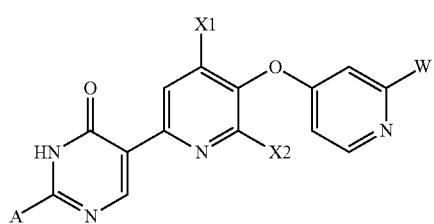

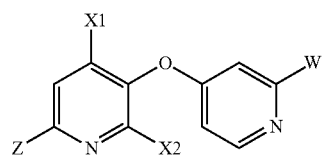

Scheme 2 illustrates the preparation of compounds of formula 18 (Formula I wherein R1 is alkyl or branched alkyl). In a manner similar to Scheme 1, compound 2 can be reacted with 14 or 15 and a palladium catalyst to afford 16. Further reaction of 16 with M-W (6) as described above provides 17. Intermediate 17 can also be prepared by the reaction of 8 (Z is bromo or iodo) with 14 or 15 and a palladium catalyst. Reaction of 17 with amine A-H (13) affords 18. In one embodiment, the thiomethyl moiety of 17 is oxidized to a methylsulfoxide or methylsulfone prior to treatment with amine A-H 13.

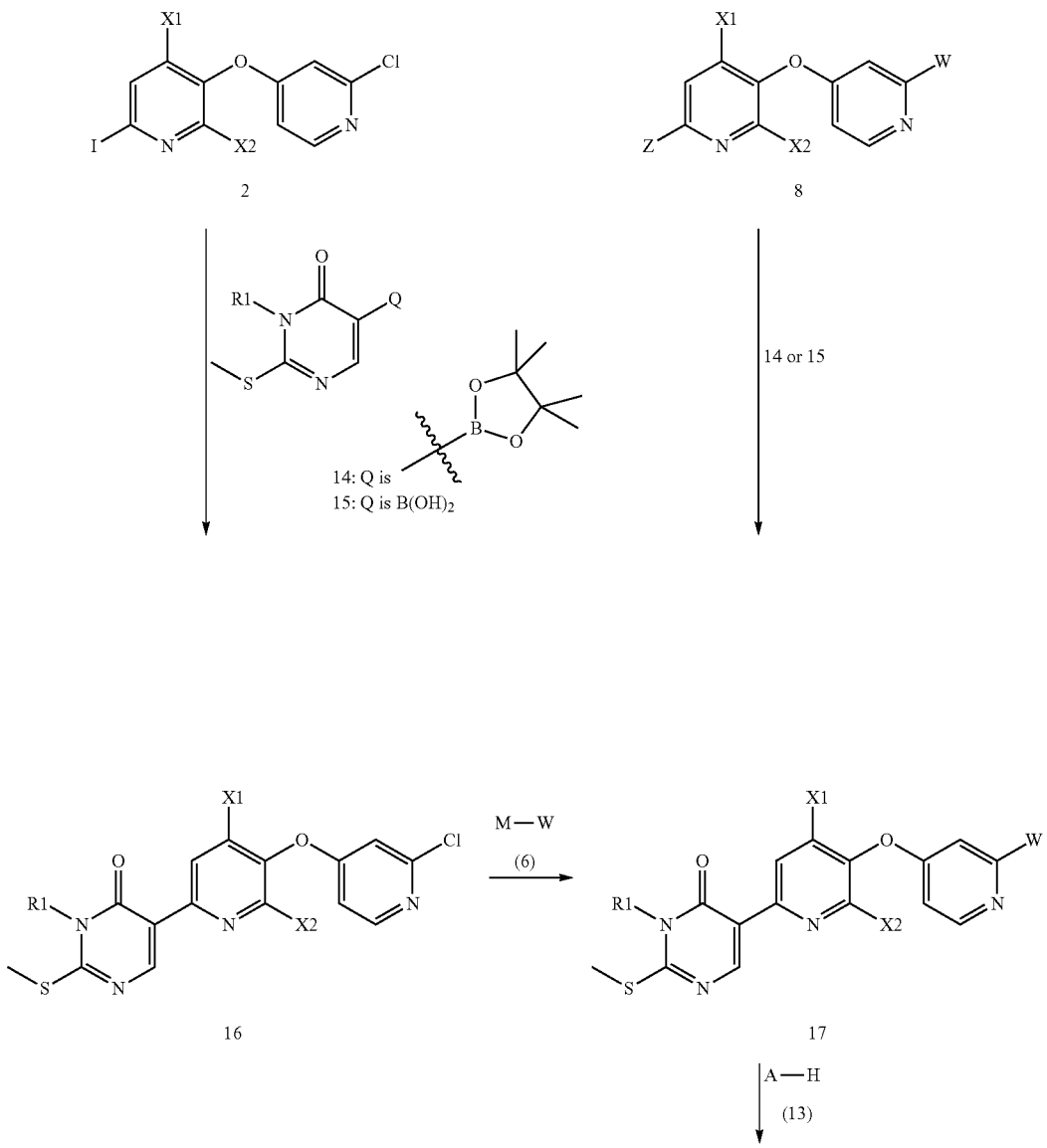

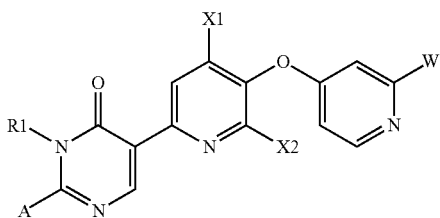

18

General intermediate 2 is prepared as illustrated in Scheme 3. Treatment of hydroxypyridine 19 with iodine in the presence of a carbonate base affords iodide 20. Further treatment of 20 with 2,4-dichloropyridine (21) in the presence of a base, for example potassium carbonate, provides 2.

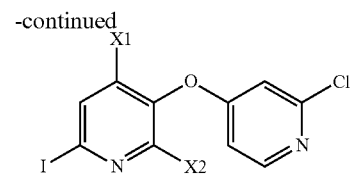

2

General intermediate 8 is prepared as illustrated in Scheme 4. Thus, intermediate 22 (Y is halogen) is reacted with 2-chloro-4-hydroxypyridine (23) in the presence of a base, for example potassium carbonate to provide the nitro ether 24. Reduction of the nitro moiey of 24 provides amine 25. Conditions to effect the conversion of 24 to 25 are known by those skilled in the art and include the use of zinc powder in the presence of ammonium chloride in a protic solvent such as methanol. Further reaction of 25 with M-W (6) as described above provides 26. In one embodiment, the order of steps for the conversion of 24 to 26 is reversed, such that 24 is first reacted with M-W 6. The product of said reaction containing a nitro moiety is then reduced to provide 26. Conversion of amine 26 to 8 is accomplished by conversion of the amino moiety of 26 to a diazonium salt and the in situ replacement of the diazonium moiety with halogen. Conditions to effect the transformation of 26 to 8 (Z is bromo) include treatment of a mixture of 26 and tetrabutylamminum bromide in dibromomethane with tert-butyl nitrite. Conditions to effect the transformation of 26 to 8 (Z is iodo) include treatment of a mixture of 26 and potassium iodide in diiodomethane with tert-butyl nitrite.

Scheme 3

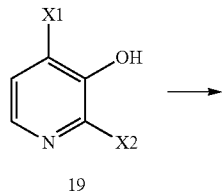

19

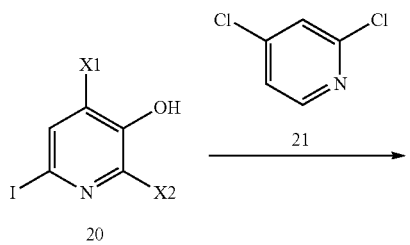

Scheme 4

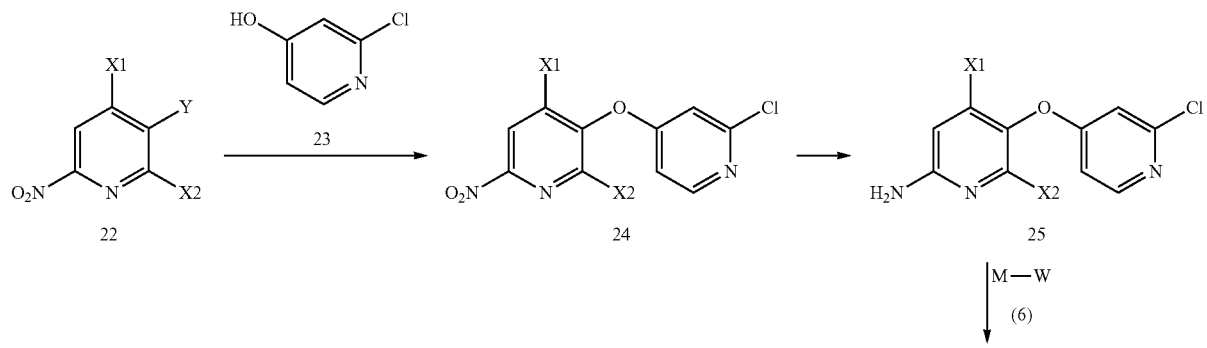

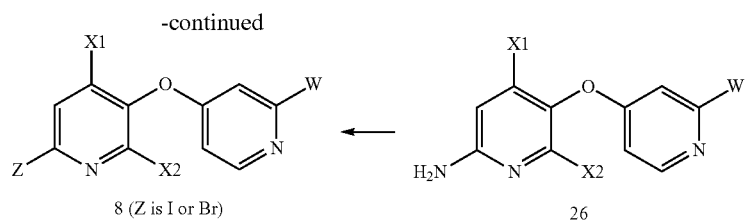

Scheme 5 illustrates the synthesis of boronate esters/boronic acids 3/4, 9/10, and 14/15. In one embodiment of Scheme 5, chloro-pyrimidine 27 is reacted with amine A-H 13 to afford 28. Conditions for the transformation include combining 27 and 13 in a solvent, for example THF, and heating the mixture to effect the reaction. Further reaction of 28 with bis(pinacolto)diboron (34) in the presence of a palladium catalyst, for example $PdCl_2$(dppf), and a mild base, for example potassium acetate, with heating provides sensitive boronate 3 and/or boronic acid 4. In practice, it is not necessary to separate potential mixtures of 3 and 4 for further use and the product(s) of the reaction of 28 and 34 is typically used in a crude form, without further purification. In another embodiment, 29 and 34 are reacted under the same conditions to provide 9 and/or 10. In practice, the product(s) of the reaction of 29 and 34 can be used in a crude form, without further purification.

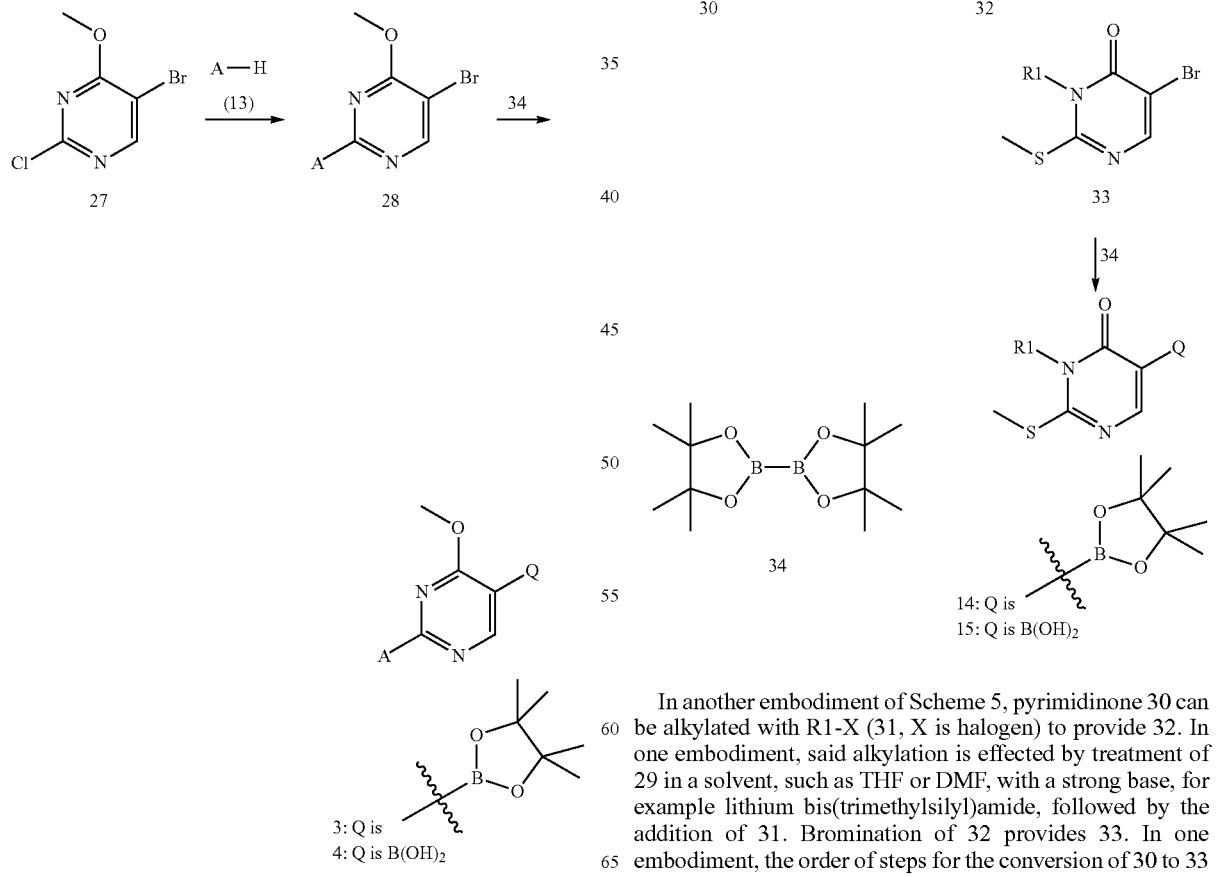

In another embodiment of Scheme 5, pyrimidinone 30 can be alkylated with R1-X (31, X is halogen) to provide 32. In one embodiment, said alkylation is effected by treatment of 29 in a solvent, such as THF or DMF, with a strong base, for example lithium bis(trimethylsilyl)amide, followed by the addition of 31. Bromination of 32 provides 33. In one embodiment, the order of steps for the conversion of 30 to 33 is reversed, such that 30 is brominated prior to alkylation with R1-X 31. Finally, reaction of 33 with 34 provides boronate 14 and/or boronic acid 15. In practice, the product(s) of the reaction of 33 and 34 can be used in a crude form, without further purification.

General intermediate 38, an example 8 wherein W is —C(O)N(R8)R9, is prepared as illustrated in Scheme 6. Thus, hydroxypyridine 35 is reacted with chloropicolinamide 36 in the presence of a base, for example potassium tert-butoxide, to provide ether 37. Diazotization of the amino moiety of 37 in the presence of iodide affords iodopyridine 38.

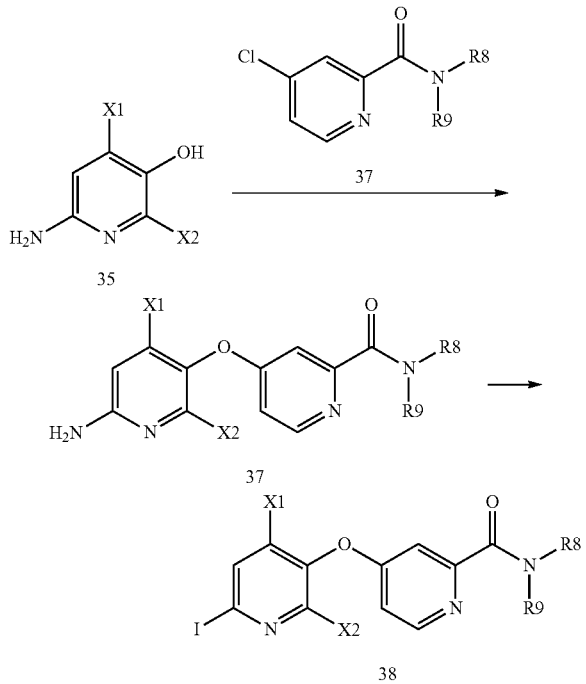

Using the synthetic procedures and methods described herein and methods known to those skilled in the art, the following compounds were made: 2-(ethylamino)-5-(6-methyl-5-((2-(1-methyl-1H-pyrazol-4-yl)pyridin-4-yl)oxy)pyridin-2-yl)pyrimidin-4(3H)-one, 2-(dimethylamino)-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(6-methyl-5-((2-(1-methyl-1H-pyrazol-4-yl)pyridin-4-yl)oxy)pyridin-2-yl)pyrimidin-4(3H)-one, 2-(ethylamino)-5-(6-methyl-5-((6'-methyl-[2,3'-bipyridin]-4-yl)oxy)pyridin-2-yl)pyrimidin-4(3H)-one, 2-(ethylamino)-5-(6-methyl-5-((2-(4-methyl-1H-imidazol-1-yl)pyridin-4-yl)oxy)pyridin-2-yl)pyrimidin-4(3H)-one, 2-((2-methoxyethyl)amino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(methylamino)pyrimidin-4(3H)-one, 2-(ethylamino)-5-(5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one, 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one, 4-((6-(2-(isopropylamino)-6-oxo-1,6-dihydropyrimidin-5-yl)oxy)-N-methylpicolinamide, 5-(6-methyl-5-((2-(1-methyl-1H-pyrazol-4-yl)pyridin-4-yl)oxy)pyridin-2-yl)-2-morpholinopyrimidin-4(3H)-one, 5-(6-methyl-5-((2-(1-methyl-1H-pyrazol-4-yl)pyridin-4-yl)oxy)pyridin-2-yl)-2-(piperidin-1-yl)pyrimidin-4(3H)-one, 2-(cyclopropylamino)-5-(6-methyl-5-((2-(1-methyl-1H-pyrazol-4-yl)pyridin-4-yl)oxy)pyridin-2-yl)pyrimidin-4(3H)-one, 2-(cyclopentylamino)-5-(6-methyl-5-((2-(1-methyl-1H-pyrazol-4-yl)pyridin-4-yl)oxy)pyridin-2-yl)pyrimidin-4(3H)-one, 3-methyl-5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one, 2-(cyclopropylamino)-3-methyl-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(4-methyl-5-((2-(1-methyl-1H-pyrazol-4-yl)pyridin-4-yl)oxy)pyridin-2-yl)pyrimidin-4(3H)-one, N-(4-((6-(2-(isopropylamino)-6-oxo-1,6-dihydropyrimidin-5-yl)-2-methylpyridin-3-yl)oxy)pyridin-2-yl)acetamide, 5-(4-methyl-5-((2-(1-methyl-1H-pyrazol-4-yl)pyridin-4-yl)oxy)pyridin-2-yl)-2-(pyrrolidin-1-yl)pyrimidin-4(3H)-one, 5-(5-((2-(1-ethyl-1H-pyrazol-4-yl)pyridin-4-yl)oxy)-6-methylpyridin-2-yl)-2-(isopropylamino)pyrimidin-4(3H)-one, (R)-2-((1-methoxypropan-2-yl)amino)-5-(6-methyl-5-((2-(1-methyl-1H-pyrazol-4-yl)pyridin-4-yl)oxy)pyridin-2-yl)pyrimidin-4(3H)-one, (R)-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidin-4(3H)-one, (S)-2-(3-(dimethylamino)pyrrolidin-1-yl)-5-(6-methyl-5-((2-(1-methyl-1H-pyrazol-4-yl)pyridin-4-yl)oxy)pyridin-2-yl)pyrimidin-4(3H)-one, 2-(ethylamino)-3-methyl-5-(6-methyl-5-((2-(1-methyl-1H-pyrazol-4-yl)pyridin-4-yl)oxy)pyridin-2-yl)pyrimidin-4(3H)-one, 2-((2-methoxyethyl)amino)-3-methyl-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-((tetrahydro-2H-pyran-4-yl)amino)pyrimidin-4(3H)-one, 2-(tert-butylamino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(neopentylamino)pyrimidin-4(3H)-one, and 2-(3,3-difluoropyrrolidin-1-yl)-5-(6-methyl-5-((2-(1-methyl-1H-pyrazol-4-yl)pyridin-4-yl)oxy)pyridin-2-yl)pyrimidin-4(3H)-one.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

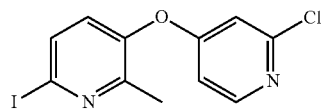 [SMILES: Cc1nc(I)ccc1Oc1ccnc(Cl)c1]

Example A1

A solution of 3-hydroxy-2-methylpyridine (20.0 g, 183 mmol) and Na$_2$CO$_3$ (38.8 g, 367 mmol) in H$_2$O (320 mL) and MeOH (200 mL) was treated with I₂ (46.5 g, 183 mmol) and stirred at RT for 1 h. The mixture was acidified with HCl (2 M), extracted with EtOAc (2×) and the combined organics were washed with brine, dried over Na₂SO₄ and concentrated to dryness. The material was suspended in 1:1 EtOAc/Hex, sonicated and the solid collected via filtration and dried. The filtrate was concentrated to dryness, treated with DCM, the solid collected via filtration and combined with the first solid to afford 6-iodo-2-methylpyridin-3-ol (20.5 g, 48%). MS (ESI) m/z: 236.0 (M+H⁺).

A mixture of 6-iodo-2-methylpyridin-3-ol (6.8 g, 28.9 mmol), 2,4-dichloropyridine (8.56 g, 57.9 mmol) and K₂CO₃ (4.00 g, 28.9 mmol) in DMA (50 mL) was heated at 110° C. for 16 h under argon. The mixture was cooled to RT, treated with H₂O, extracted with EtOAc (2×) and the combined organics were washed with H₂O, then brine, dried over Na₂SO₄, concentrated to dryness and purified via silica gel chromatography (EtOAc/Hex) to afford 3-((2-chloropyridin-4-yl)oxy)-6-iodo-2-methylpyridine (7.35 g, 73%) as a white solid. MS (ESI) m/z: 346.9 (M+H⁺).

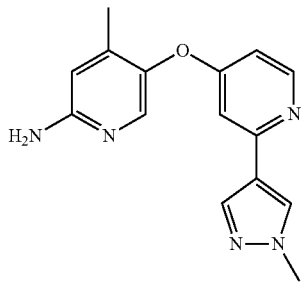 [SMILES: Cc1cc(N)ncc1Oc1ccnc(-c2cnn(C)c2)c1]

Example A2

A 0° C. solution of H₂SO₄ (12 mL) was treated with H₂O₂ (9.72 mL, 95 mmol), stirred for 10 min, treated with a solution of 2-amino-5-fluoro-4-methylpyridine (2 g, 15.86 mmol) in H₂SO₄ (8 mL), stirred for 15 min, then warmed to RT and stirred for 3 h. The mixture was re-cooled to 0° C., neutralized slowly with solid NaHCO₃ and the resulting solid was collected by filtration and dried to afford 5-fluoro-4-methyl-2-nitropyridine (2 g, 81%). ¹H NMR (400 MHz, DMSO-d₆): δ 8.57 (s, 1H), 8.42 (d, J=5.3 Hz, 1H), 2.42 (d, J=1.9 Hz, 3H); MS (ESI) m/z: 157.1 (M+H⁺).

A mixture of 5-fluoro-4-methyl-2-nitropyridine (2 g, 12.81 mmol) and 2-chloro-4-hydroxypyridine (1.66 g, 12.81 mmol) in DMF (26 mL) was sparged with Ar, treated with K₂CO₃ (2.66 g, 19.22 mmol), heated at 88° C. for 24 h, then at 50° C. for 2 days. The mixture was treated with water and the resulting solid collected via filtration and dried to afford 5-((2-chloropyridin-4-yl)oxy)-4-methyl-2-nitropyridine (2.72 g, 80%). ¹H NMR (400 MHz, DMSO-d₆): δ 8.49 (s, 1H), 8.47 (s, 1H), 8.35 (d, J=5.7 Hz, 1H), 7.24 (d, J=2.3 Hz, 1H), 7.12 (dd, J=5.7, 2.3 Hz, 1H), 2.32 (s, 3H); MS (ESI) m/z: 266.0 (M+H⁺).

A solution of 5-((2-chloropyridin-4-yl)oxy)-4-methyl-2-nitropyridine (1.5 g, 5.65 mmol) and 1-methyl-4-(4,4,5,5-tetramethyl-1,3,2-dioxaborolan-2-yl)-1H-pyrazole (1.527 g, 7.34 mmol) in dioxane (20 mL) was sparged with Ar, treated with a solution of K₂CO₃ (1.171 g, 8.47 mmol) in water (5 mL) and Pd(PPh₃)₄ (0.326 g, 0.282 mmol) and heated at 80° C. overnight. The mixture was cooled to RT, treated with water, extracted with DCM (4×) and the combined organics were dried over Na₂SO₄, concentrated to dryness and purified via silica gel chromatography (MeOH/DCM) to afford 4-methyl-5-((2-(1-methyl-1H-pyrazol-4-yl)pyridin-4-yl)oxy)-2-nitropyridine (2.3 g, 75%). ¹H NMR (400 MHz, DMSO-d₆): δ 8.48 (s, 1H), 8.43-8.42 (m, 2H), 8.27 (s, 1H), 7.98 (s, 1H), 7.30 (d, J=2.4 Hz, 1H), 6.83 (dd, J=5.7, 2.4 Hz, 1H), 3.84 (s, 3H), 2.34 (s, 3H); MS (ESI) m/z: 312.1 (M+H⁺).

A solution of 4-methyl-5-((2-(1-methyl-1H-pyrazol-4-yl)pyridin-4-yl)oxy)-2-nitropyridine (2.3 g, 7.39 mmol) in MeOH (37 mL) and THF (37 mL) was treated with NH₄Cl (11.86 g, 222 mmol) followed by the portion-wise addition of zinc dust (4.83 g, 73.9 mmol) and the mixture stirred at RT overnight. The mixture was diluted with EtOAc, the solids removed via filtration through diatomaceous earth and the filtrate concentrated to dryness and purified via silica gel chromatography (MeOH/DCM) to afford 4-methyl-5-((2-(1-methyl-1H-pyrazol-4-yl)pyridin-4-yl)oxy)pyridin-2-amine (1.4 g, 67%). MS (ESI) m/z: 282.1 (M+H⁺).

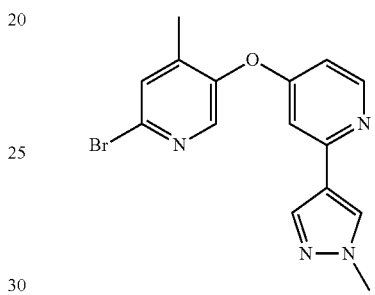

Example A3

A solution of Example A2 (0.2 g, 0.71 mmol) in dibromomethane (5 mL) was treated with tetrabutylammonium bromide (0.92 g, 2.84 mmol) and t-butylnitrite (0.7 g, 7.11 mmol) and stirred at RT for 4 h. The mixture was diluted with EtOAc, washed successively with satd. NaHCO₃, water, and brine, dried over Na₂SO₄ and concentrated to dryness to afford 2-bromo-4-methyl-5-((2-(1-methyl-1H-pyrazol-4-yl)pyridin-4-yl)oxy)pyridine as off-white solid (0.21 g, 86%). MS (ESI) m/z: 345.1 (M+H⁺).

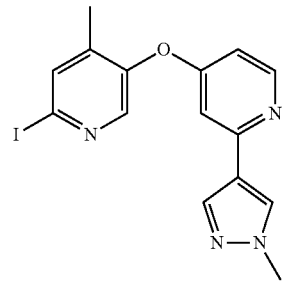 [SMILES: Cc1cc(I)ncc1Oc1ccnc(-c2cnn(C)c2)c1]

Example A4

A suspension of Example A2 (0.62 g, 2.2 mmol), KI (3.7 g, 22.3 mmol), and diiodomethane (5 mL, 62 mmol) was treated with t-butylnitrite (1.4 mL, 11.7 mmol) and stirred at RT for 12 h. The mixture was treated with EtOAc, washed successively with satd. NaHCO₃ (3×), 10% Na₂S₂O₃ (2×), and brine (2×) and the combined aqueous washes were back-extracted with EtOAc (2×). The combined organics were dried over MgSO₄, concentrated to dryness and purified by silica gel chromatography (EtOAc/DCM) to afford 2-iodo-4-methyl-5-((2-(1-methyl-1H-pyrazol-4-yl)pyridin-4-yl)oxy)pyridine (0.51 g, 59%). MS (ESI) m/z: 393.0 (M+H⁺).

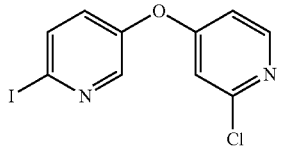 [SMILES: Clc1cc(Oc2ccc(I)nc2)ccn1]

Example A5

A solution of 5-bromo-2-nitropyridine (15 g, 73.9 mmol) in DMF (300 mL) was sparged with Ar, treated with Cs₂CO₃ (48.2 g, 148 mmol) and 2-chloro-4-hydroxypyridine (10.53 g, 81 mmol), sparged again with Ar and heated at 85° C. overnight. The mixture was cooled to RT, filtered through a bed of silica gel, washed thoroughly with EtOAc, and the filtrate treated with 5% LiCl and stirred overnight. The layers were separated, the aqueous layer extracted with additional EtOAc (4×) and the combined organics were dried over Na₂SO₄ and concentrated to dryness. The residue was dissolved in EtOAc, treated with 5% LiCl, stirred for 1 h, the layers separated and the aqueous layer extracted with EtOAc (3×). The combined organics were dried over Na₂SO₄, concentrated to dryness and purified via silica gel chromatography (EtOAc/Hex). The material was suspended in MTBE, sonicated and the resulting solid collected via filtration to afford 2-chloro-4-((6-nitropyridin-3-yl)oxy)pyridine (6.06 g, 33%). ¹H NMR (400 MHz, DMSO-d₆): δ 8.62 (d, J=2.4, 1H), 8.43-8.39 (m, 2H), 8.06 (dd, J=8.8, 2.8 Hz, 1H), 7.36 (d, J=2.0 Hz, 1H), 7.23 (dd, J=5.6, 2.0 Hz, 1H); MS (ESI) m/z: 252.0 (M+H⁺).

A solution of 2-chloro-4-((6-nitropyridin-3-yl)oxy)pyridine (20.0 g, 79 mmol) in MeOH (40 mL) was hydrogenated in presence of Raney Nickel (2.00 g, 34.1 mmol) at 40 psi for 3 h. The catalyst was removed via filtration, rinsed with MeOH and the filtrate concentrated to dryness to afford 5-((2-chloropyridin-4-yl)oxy)pyridin-2-amine (18.52 g, 105%) as a brown solid. MS (ESI) m/z: 222.0 (M+H⁺).

A mixture of 5-((2-chloropyridin-4-yl)oxy)pyridin-2-amine (1.00 g, 4.51 mmol) and potassium iodide (3.74 g, 22.5 mmol) in DCM (15 mL) was treated dropwise with t-butyl nitrite (4.65 g, 45.1 mmol) and the mixture was stirred overnight at RT. The mixture was diluted with EtOAc (75 mL) and washed with 10% Na₂CO₃ (50 mL), then water (50 mL) and finally brine (50 mL) and dried over sodium sulfate. The solvents were evaporated at reduced pressure to give a thick oily solution. EtOAc (100 mL) was added and the solution was washed with 0.1M sodium thiosulfate (75 mL), brine (50 mL) and dried over sodium sulfate. The solvents were evaporated at reduced pressure, and the residual oil was purified by silica gel chromatography to provide 2-chloro-4-((6-iodopyridin-3-yl)oxy)pyridine (695 mg, 46%). ¹H NMR (400 MHz, DMSO-d₆): δ 8.80 (d, J=3.0 Hz, 1H), 8.73 (d, J=5.8 Hz, 1H), 8.35 (d, J=8.6 Hz, 1H), 7.91 (dd, J=8.6, 3.1 Hz, 1H), 7.61 (d, J=2.3 Hz, 1H), 7.48 (dd, J=5.8, 2.3 Hz, 1H).

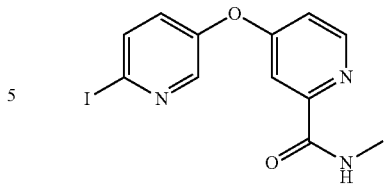

Example A6

DMF (25 mL) was slowly treated with SOCl₂ (125 mL) to maintain a temperature of 40-50° C. The mixture was then treated portion-wise with pyridine-2-carboxylic acid (25 g, 0.2 mol) over 0.5 h, then heated at reflux for 16 h, cooled to RT, diluted with toluene (80 mL) and concentrated to dryness (this process was repeated three times). The resulting residue was washed with toluene and dried under reduced pressure to yield 4-chloro-pyridine-2-carbonyl chloride (27.6 g, 79% yield), which was used in the next step without purification.

A 0° C. solution of 4-chloro-pyridine-2-carbonyl chloride (27.6 g, 0.16 mol) in THF (100 mL) at was treated drop-wise with a solution of MeNH₂ in EtOH, stirred at 3° C. for 4 h, then concentrated to dryness. The material was suspended in EtOAc, the solids removed via filtration and the filtrate was washed with brine (2×), dried and concentrated to yield 4-chloro-N-methylpicolinamide (16.4 g, 60%) as a yellow solid. ¹H NMR (400 MHz, DMSO-d₆) δ 8.78 (br s, 1H), 8.55 (d, J=5.2 Hz, 1H), 7.97 (d, J=2.0 Hz, 1H), 7.66 (m, 1H), 2.82 (d, J=4.8 Hz, 3H); MS (ESI) m/z: 171.0 (M+H⁺).

A solution of 2-amino-5-hydroxypyridine (0.968 g, 8.79 mmol) in DMA (15 mL) was treated with potassium tert-butoxide (0.987 g, 8.79 mmol), stirred at RT for 3 h, treated with 4-chloro-N-methylpicolinamide (1.5 g, 8.79 mmol) and stirred at RT for 2 days. The mixture was concentrated to dryness, treated with water, extracted with EtOAc (3×) and the combined organics were washed with brine, dried over Na₂SO₄, concentrated to dryness and purified via silica gel chromatography (EtOAc, MeOH/DCM) to afford 4-((6-aminopyridin-3-yl)oxy)-N-methylpicolinamide (1.3 g, 61%). ¹H NMR (400 MHz, DMSO-d₆): δ 8.75 (m, 1H), 8.46 (d, J=5.6 Hz, 1H), 7.82 (d, J=2.9 Hz, 1H), 7.34 (d, J=2.6 Hz, 1H), 7.30 (dd, J=8.9, 3.0 Hz, 1H), 7.10 (dd, J=5.6, 2.7 Hz, 1H), 6.53 (d, J=8.9 Hz, 1H), 6.07 (s, 2H), 2.77 (d, J=4.8 Hz, 3H); MS (ESI) m/z: 245.1 (M+H⁺).

A mixture of 4-((6-aminopyridin-3-yl)oxy)-N-methylpicolinamide (0.4 g, 1.64 mmol) and potassium iodide (1.36 g, 8.19 mmol) in methylene iodide (5.46 mL) was treated drop-wise with t-butylnitrite (1.95 mL, 16.4 mmol). The mixture was stirred overnight at RT, diluted with EtOAc (75 mL), and washed with 10% sodium carbonate (50 mL), 10% thiosulfate (50 mL), and brine (50 mL). The organics were dried over sodium sulfate, evaporated to dryness and purified by silica gel chromatography ((EtOAc/Hex) to afford 4-((6-iodopyridin-3-yl)oxy)-N-methylpicolinamide (0.214 g, 36.8%). ¹H NMR (400 MHz, DMSO-d₆): δ 8.78 (br d, J=5.6 Hz, 1H), 8.54 (d, J=5.6 Hz, 1H), 8.40 (d, J=3.0 Hz, 1H), 7.95 (d, J=8.6 Hz, 1H), 7.50 (dd, J=8.6, 3.1 Hz, 1H), 7.45 (d, J=2.6 Hz, 1H), 7.23 (dd, J=5.6, 2.7 Hz, 1H), 2.78 (d, J=4.9 Hz, 3H); MS (ESI) m/z: 356.0 (M+H⁺).

Example B1

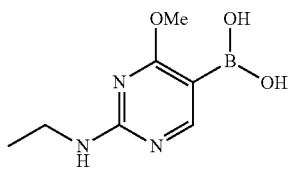

A solution of 5-bromo-2-chloro-4-methoxypyrimidine (0.6 g, 2.69 mmol) in THF (10 mL) was treated with ethylamine (2.0M in THF, 6.71 mL, 13.43 mmol) was heated at 60° C. for 1 h, cooled to RT and diluted with water. The mixture was extracted with EtOAc (2×) and the combined organics were washed with brine, dried over $Na_2SO_4$, concentrated to dryness and purified by column chromatography (EtOAc/Hex) to afford 5-bromo-N-ethyl-4-methoxypyrimidin-2-amine as a white solid (0.54 g, 87%). MS (ESI) m/z: 232.03 (M+H$^+$).

A solution of 5-bromo-N-ethyl-4-methoxypyrimidin-2-amine (0.73 g, 3.15 mmol) in dioxane (25 mL) was sparged with Ar, treated with bis(pinacalato)diboran (1.04 g, 4.1 mmol), KOAc (0.62 g, 6.29 mmol), PdCl$_2$(dppf) (0.23 g, 0.315 mmol) and heated at 100° C. for 20 h. The mixture was cooled to RT to afford a solution of crude (2-(ethylamino)-4-methoxypyrimidin-5-yl)boronic acid (50% yield assumed) which was used without further purification. MS (ESI) m/z: 198.1 (M+H$^+$).

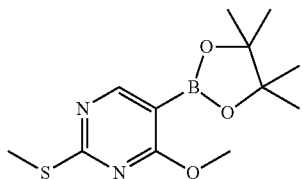

Example B2

A mixture of 5-bromo-4-methoxy-2-(methylthio)pyrimidine (1.0 g, 4.25 mmol), bis(pinacalato)diboran (1.30 g, 5.10 mmol), and KOAc (1.25 g, 12.76 mmol) in dioxane (10 mL) was sparged with Ar, treated with PdCl$_2$(dppf)-DCM adduct (0.17 g, 0.21 mmol), sparged again with Ar and heated at 85° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (MeOH/EtOAc) to obtain (4-methoxy-2-(methylthio)pyrimidin-5-yl)boronic acid pinacol ester (100% yield assumed) which was used without further purification. MS (ESI) m/z: 201.1 (M+H$^+$).

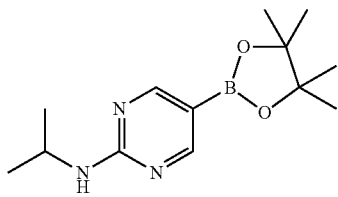 [SMILES: CC(C)Nc1ncc(B2OC(C)(C)C(C)(C)O2)cn1]

Example B3

A solution of 5-bromo-2-chloro-4-methoxypyrimidine (1.2 g, 5.37 mmol) in THF (20 mL) was treated with TEA (1.57 mL, 10.74 mmol) and isopropylamine (0.7 mL, 8.1 mmol) and heated at 60° C. for 5 h. The mixture was cooled to RT, treated with water, extracted with EtOAc (2×) and the combined organics were washed with brine, dried over Na$_2$SO$_4$, concentrated to dryness and purified by silica gel chromatography (EtOAc/Hex) to afford 5-bromo-N-isopropyl-4-methoxypyrimidin-2-amine (0.84 g, 634%). $^1$H NMR (400 MHz, DMSO-d$_6$): δ 8.10 (s, 1H), 7.17 (br s, 1H), 3.96-3.94 (m, 1H), 3.87 (s, 3H), 1.12 (d, J=6.5 Hz, 6H); MS (ESI) m/z: 246.0 (M+H$^+$).

A solution of 5-bromo-N-isopropyl-4-methoxypyrimidin-2-amine (0.84 g, 3.41 mmol) in dioxane (20 mL) was sparged with Ar, treated with bis(pinacolato)diboran (1.127 g, 4.44 mmol), KOAc (0.502 g, 5.12 mmol) and PdCl2(dppf)-DCM adduct (0.279 g, 0.341 mmol) and heated at 95° C. for 16 h. The mixture was cooled to RT and concentrated to dryness to afford crude N-isopropyl-4-methoxy-5-(4,4,5,5-tetramethyl-1,3,2-dioxaborolan-2-yl)pyrimidin-2-amine (60% yield assumed) which was used without further purification. MS (ESI) m/z: 212.1 (M+H$^+$) [ion for corresponding boronic acid].

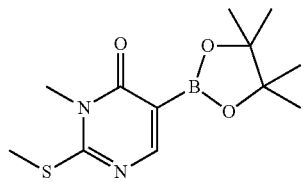

Example B4

A 0° C. suspension of 2-(methylthio)pyrimidin-4(3H)-one (2.0 g, 14.1 mmol) in DMF (40 mL) was treated with solid LiHMDS (3.06 g, 18.3 mmol), followed by methyl iodide (1.14 mL, 18.3 mmol), warmed to RT and stirred overnight. The mixture was quenched with water, extracted with EtOAc (3×) and the combined organics were dried over Na$_2$SO$_4$, concentrated to dryness and purified via silica gel chromatography (EtOAc/Hex) to afford 3-methyl-2-(methylthio)pyrimidin-4(3H)-one (1.37 g, 62%). $^1$H NMR (400 MHz, DMSO-d$_6$): δ 7.83 (d, J=6.5 Hz, 1H), 6.17 (d, J=6.5 Hz, 1H), 3.39 (s, 3H), 2.54 (s, 3H); MS (ESI) m/z: 157.1 (M+H$^+$).

A 0° C. solution of 3-methyl-2-(methylthio)pyrimidin-4(3H)-one (1.37 g, 8.77 mmol) in CHCl$_3$ (15 mL) was treated with bromine (0.54 mL, 10.5 mmol), stirred at 0° C. for 1 h, quenched with satd. NaHCO$_3$ (15 mL), warmed to RT slowly and stirred overnight. The mixture was extracted with DCM (3×) and the combined organics were dried over Na$_2$SO$_4$ and concentrated to dryness to afford 5-bromo-3-methyl-2-(methylthio)pyrimidin-4(3H)-one (2.0 g, 97% yield). $^1$H NMR (400 MHz, DMSO-d$_6$): δ 8.24 (s, 1H), 3.45 (s, 3H), 2.55 (s, 3H); MS (ESI) m/z: 235.0 (M+H$^+$).

A mixture of 5-bromo-3-methyl-2-(methylthio)pyrimidin-4(3H)-one (1.0 g, 4.25 mmol), bis(pinacalato)diboran (1.30 g, 5.10 mmol), and KOAc (1.25 g, 12.7 mmol) in dioxane (10 mL) was sparged with Ar, treated with PdCl$_2$(dppf)-DCM-adduct (0.17 g, 0.21 mmol), sparged again with Ar and heated at 85° C. overnight. The mixture was cooled to RT, quenched with satd. NaHCO$_3$, extracted with EtOAc (3×) and the combined organics were dried over Na$_2$SO$_4$ and concentrated to dryness to afford 3-methyl-2-(methylthio)-5-(4,4,5,5-tetramethyl-1,3,2-dioxaborolan-2-yl)pyrimidin-4(3H)-one (100% yield assumed). MS (ESI) m/z: 202.1 (mass of boronic acid+H⁺).

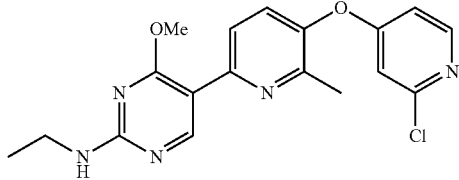 [SMILES: CCNc1ncc(-c2ccc(Oc3ccnc(Cl)c3)c(C)n2)c(OC)n1]

Example C1

A solution of crude Example B1 (0.310 g, 1.574 mmol) in dioxane (25 mL) was treated with a degassed solution of K₂CO₃ (0.65 g, 4.72 mmol) in water (4 mL), Example A1 (0.55 g, 1.58 mmol) and Pd(PPh₃)₄ (0.18 g, 0.16 mmol) and heated at 90° C. for 16 h. The mixture was cooled to RT, diluted with water, extracted with EtOAc (3×) and the combined organics were washed with brine, dried over Na₂SO₄, concentrated to dryness and purified by column chromatography (EtOAc/DCM) to afford 5-(5-((2-chloropyridin-4-yl)oxy)-6-methylpyridin-2-yl)-N-ethyl-4-methoxypyrimidin-2-amine (350 mg, 60%). ¹H NMR (400 MHz, DMSO-d₆): δ 8.73 (s, 1H), 8.29 (d, J=5.8 Hz, 1H), 7.77 (d, J=8.9 Hz, 1H), 7.61 (d, J=8.6 Hz, 1H), 7.38 (br s, 1H), 7.06 (d, J=2.3 Hz, 1H), 6.94 (dd, J=5.8, 2.3 Hz, 1H), 4.01-3.91 (m, 3H), 3.36-3.34 (m, 2H), 2.33 (s, 3H), 1.15 (t, J=7.4 Hz, 3H); MS (ESI) m/z: 372.1 (M+H⁺).

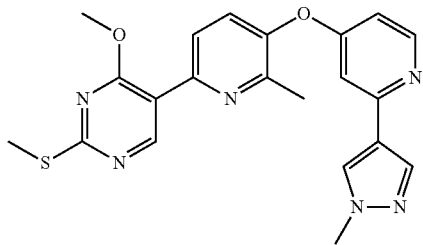 [SMILES: COc1nc(SC)ncc1-c1ccc(Oc2ccnc(-c3cnn(C)c3)c2)c(C)n1]

Example C2

A mixture of B2 (0.63 g, 2.25 mmol), Example A1 (0.65 g, 1.88 mmol), and K₂CO₃ (0.78 g, 5.63 mmol) in 5:1 dioxane/H₂O (6 mL) was sparged with Ar, treated with Pd(PPh₃)₄ (0.22 g, 0.19 mmol), sparged again with Ar and heated at 90° C. overnight. The mixture was cooled to RT, treated with satd. NaHCO₃, extracted with EtOAc (3×) and the combined organics were dried over Na₂SO₄, concentrated to dryness and purified via silica gel chromatography (EtOAc/Hex) to obtain 5-(5-((2-chloropyridin-4-yl)oxy)-6-methylpyridin-2-yl)-4-methoxy-2-(methylthio)pyrimidine (0.49 g, 70%). ¹H NMR (400 MHz, DMSO-d₆): δ 8.91 (s, 1H), 8.31 (d, J=5.8 Hz, 1H), 7.89 (d, J=8.5 Hz, 1H), 7.72 (d, J=8.5 Hz, 1H), 7.11 (d, J=2.3 Hz, 1H), 6.99 (dd, J=5.8, 2.3 Hz, 1H), 4.06 (s, 3H), 2.58 (s, 3H), 2.39 (s, 3H); MS (ESI) m/z: 375.1 (M+H⁺).

A mixture of 1-methyl-4-(4,4,5,5-tetramethyl-1,3,2-dioxaborolan-2-yl)-1H-pyrazole (0.30 g, 1.44 mmol), 5-(5-((2-chloropyridin-4-yl)oxy)-6-methylpyridin-2-yl)-4-methoxy-2-(methylthio)pyrimidine (0.49 g, 1.31 mmol), and K₂CO₃ (0.54 g, 3.92 mmol) in 5:1 dioxane/water (18 mL) was sparged with Ar, treated with Pd(PPh₃)₄ (0.15 g, 0.13 mmol), sparged again with Ar and heated at 90° C. for 4 h. The mixture was cooled to RT, treated with satd. NaHCO₃, extracted with EtOAc (3×) and the combined organics were dried over Na₂SO₄, concentrated to dryness and purified via silica gel chromatography (MeOH/DCM) to obtain 4-methoxy-5-(6-methyl-5-((2-(1-methyl-1H-pyrazol-4-yl)pyridin-4-yl)oxy)pyridin-2-yl)-2-(methylthio)pyrimidine (0.54 g, 98%). ¹H NMR (400 MHz, DMSO-d₆): δ 8.93 (s, 1H), 8.39 (d, J=5.7 Hz, 1H), 8.28 (s, 1H), 7.99 (d, J=0.7 Hz, 1H), 7.88 (d, J=8.5 Hz, 1H), 7.65 (d, J=8.6 Hz, 1H), 7.30 (d, J=2.4 Hz, 1H), 6.66 (dd, J=5.7, 2.4 Hz, 1H), 4.06 (s, 3H), 3.85 (s, 3H), 2.58 (s, 3H), 2.42 (s, 3H); MS (ESI) m/z: 421.1 (M+H⁺).

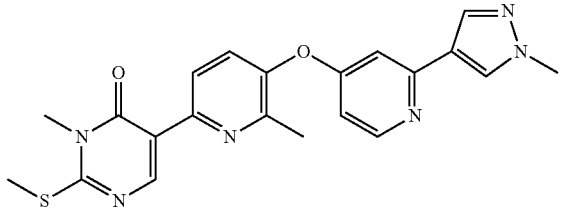

Example C3

A mixture of Example B4 (0.35 g, 1.73 mmol), Example A1 (0.50 g, 1.44 mmol), and K₂CO₃ (0.60 g, 4.33 mmol) in 5:1 dioxane/water (12 mL) was sparged with Ar, treated with Pd(PPh₃)₄ (0.17 g, 0.14 mmol), sparged again with Ar and heated at 90° C. overnight. The mixture was quenched with satd. NaHCO₃, extracted with EtOAc (3×) and the combined organics were dried over Na₂SO₄, concentrated to dryness and purified via silica gel chromatography (EtOAc/Hex) to afford 5-(5-((2-chloropyridin-4-yl)oxy)-6-methylpyridin-2-yl)-3-methyl-2-(methylthio)pyrimidin-4(3H)-one (0.52 g, 67%). MS (ESI) m/z: 375.1 (M+H⁺).

A mixture of 5-(5-((2-chloropyridin-4-yl)oxy)-6-methylpyridin-2-yl)-3-methyl-2-(methylthio)pyrimidin-4(3H)-one (0.52 g, 0.97 mmol), 1-methyl-4-(4,4,5,5-tetramethyl-1,3,2-dioxaborolan-2-yl)-1H-pyrazole (0.22 g, 1.07 mmol), and K₂CO₃ (0.40 g, 2.9 mmol) in 5:1 dioxane/water (6 mL) was sparged with Ar, treated with Pd(PPh₃)₄ (0.12 g, 0.10 mmol), sparged again with Ar and heated at 90° C. overnight. The solids were removed via filtration, the filtrate treated with satd. NaHCO₃, extracted with EtOAc (3×) and the combined organics were dried over Na₂SO₄, concentrated to dryness and purified via silica gel chromatography (MeOH/DCM) to afford 3-methyl-5-(6-methyl-5-((2-(1-methyl-1H-pyrazol-4-yl)pyridin-4-yl)oxy)pyridin-2-yl)-2-(methylthio)pyrimidin-4(3H)-one (140 mg, 34%). MS (ESI) m/z: 421.1 (M+H⁺).

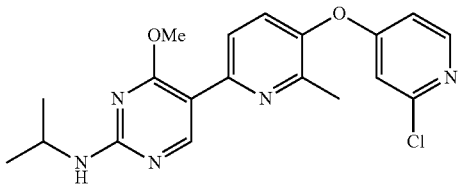 [SMILES: COc1nc(NC(C)C)ncc1-c1ccc(Oc2ccnc(Cl)c2)c(C)n1]

Example C4

A solution of Example B3 (0.698 g, 2.381 mmol) in dioxane (20 mL) was treated with Example A1 (0.7 g, 2.4 mmol), a solution of K$_2$CO$_3$ (0.22 g, 1.6 mmol) in water (6 mL) and Pd(PPh$_3$)$_4$ (0.18 g, 0.16 mmol), sparged with Ar and heated at 90° C. overnight. The mixture was cooled to RT, treated with water, extracted with EtOAc (2×) and the combined organics were washed with brine, dried over Na$_2$SO$_4$, concentrated to dryness and purified by silica gel chromatography (EtOAc/Hex) to afford 5-(5-((2-chloropyridin-4-yl)oxy)-6-methylpyridin-2-yl)-N-isopropyl-4-methoxypyrimidin-2-amine (0.48 g, 55%). MS (ESI) m/z: 386.2 (M+H$^+$).

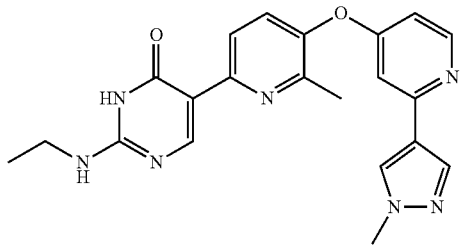 [SMILES: CCNc1ncc(-c2ccc(Oc3ccnc(-c4cnn(C)c4)c3)c(C)n2)c(=O)[nH]1]

Example 1

A solution of Example C1 (0.12 g, 0.26 mmol) and 1-methyl-4-(4,4,5,5-tetramethyl-1,3,2-dioxaborolan-2-yl)-1H-pyrazole (0.070 g, 0.35 mmol) in dioxane (4 mL) was sparged with Ar, treated with a solution of K$_2$CO$_3$ (0.07 g, 0.51 mmol) in water (1 mL), Pd(PPh$_3$)$_4$ (0.03 g, 0.026 mmol) and heated at 90° C. for 2 h. The mixture was cooled to RT, diluted with water, extracted with EtOAc (2×) and the combined organics were washed with brine, dried over Na$_2$SO$_4$, concentrated to dryness and purified by column chromatography (MeOH/DCM) to afford N-ethyl-4-methoxy-5-(6-methyl-5-((2-(1-methyl-1H-pyrazol-4-yl)pyridin-4-yl)oxy)pyridin-2-yl)pyrimidin-2-amine as a white solid (77 mg, 71%). $^1$H NMR (400 MHz, DMSO-d$_6$): δ 8.74 (s, 1H), 8.36 (d, J=5.7 Hz, 1H), 8.26 (s, 1H), 7.97 (d, J=0.7 Hz, 1H), 7.76 (d, J=8.5 Hz, 1H), 7.55 (d, J=8.6 Hz, 1H), 7.36 (br s, 1H), 7.25 (d, J=2.4 Hz, 1H), 6.61 (dd, J=5.7, 2.4 Hz, 1H), 3.96 (s, 3H), 3.84 (s, 3H), 3.40-3.30 (m, 2H), 2.37 (s, 3H), 1.14 (br m, 3H); MS (ESI) m/z: 418.2 (M+H$^+$).

A mixture of N-ethyl-4-methoxy-5-(6-methyl-5-((2-(1-methyl-1H-pyrazol-4-yl)pyridin-4-yl)oxy)pyridin-2-yl)pyrimidin-2-amine (0.29 g, 0.7 mmol) and 48% aq. HBr (0.32 mL, 2.78 mmol) in acetic acid (5 mL) was heated at 90° C. for 6 h. The mixture was cooled to RT, diluted with water (60 mL), made basic with solid NaHCO$_3$, extracted with 1:1 EtOAc/THF (3×) and the combined organics were washed with brine, dried over Na$_2$SO$_4$ and concentrated to dryness. The residue was stirred with MeCN for 1 h and the resulting solid was collected via filtration to afford 2-(ethylamino)-5-(6-methyl-5-((2-(1-methyl-1H-pyrazol-4-yl)pyridin-4-yl)oxy)pyridin-2-yl)pyrimidin-4(3H)-one as white solid (210 mg, 75%). $^1$H NMR (400 MHz, DMSO-d$_6$): δ 11.20 (br s, 1H), 8.67 (s, 1H), 8.35 (d, J=5.7 Hz, 1H), 8.24-8.26 (m, 2H), 7.96 (s, 1H), 7.50 (d, J=8.6 Hz, 1H), 7.21 (d, J=2.4 Hz, 1H), 6.88 (br s, 1H), 6.60 (dd, J=5.7, 2.4 Hz, 1H), 3.84 (s, 3H), 3.34-3.32 (m, 2H), 2.34 (s, 3H), 1.12 (t, J=7.2 Hz, 3H); MS (ESI) m/z: 404.2 (M+H$^+$).

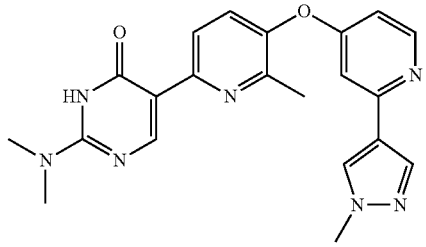 [SMILES: Cc1nc(-c2cnc(N(C)C)[nH]c2=O)ccc1Oc1ccnc(-c2cnn(C)c2)c1]

Example 2

A solution of Example C2 (0.13 g, 0.309 mmol) in DCM (5 mL) was treated portion-wise with mCPBA (0.09 g, 0.37 mmol), stirred at RT overnight, treated with TEA (0.5 mL) and N,N-dimethylamine HCl salt (500 mg) and stirred at RT for 2 h. The mixture was treated with satd. NaHCO$_3$, extracted with DCM (2×) and the combined organics were dried over Na$_2$SO$_4$, concentrated to dryness and purified via silica gel chromatography (MeOH/DCM) to obtain 4-methoxy-N,N-dimethyl-5-(6-methyl-5-((2-(1-methyl-1H-pyrazol-4-yl)pyridin-4-yl)oxy)pyridin-2-yl)pyrimidin-2-amine (60 mg, 47%). MS (ESI) m/z: 418.2 (M+H$^+$).

A solution of 4-methoxy-N,N-dimethyl-5-(6-methyl-5-((2-(1-methyl-1H-pyrazol-4-yl)pyridin-4-yl)oxy)pyridin-2-yl)pyrimidin-2-amine (0.060 g, 0.144 mmol) in acetic acid (5 mL) was treated with HBr (0.065 mL, 0.575 mmol), heated at 90° C. for 6 h, cooled to RT and quenched with ice water. The solution was treated with NaHCO$_3$ and NaCl, extracted with 1:1 THF/EtOAc (3×) and the combined organics were dried over Na$_2$SO$_4$ and concentrated to dryness. The material was treated with MeCN (1 mL), allowed to stand at RT and the resulting solid was collected via filtration to afford 2-(dimethylamino)-5-(6-methyl-5-((2-(1-methyl-1H-pyrazol-4-yl)pyridin-4-yl)oxy)pyridin-2-yl)pyrimidin-4(3H)-one (43 mg, 71%). $^1$H NMR (400 MHz, DMSO-d$_6$): δ 11.23 (s, 1H), 8.73 (s, 1H), 8.36 (d, J=5.7 Hz, 1H), 8.30 (m, 1H), 8.26 (s, 1H), 7.97 (s, 1H), 7.51 (m, 1H), 7.23 (d, J=2.4 Hz, 1H), 6.62 (br s, 1H), 3.85 (s, 3H), 3.12 (s, 6H), 2.35 (s, 3H); MS (ESI) m/z: 404.2 (M+H$^+$).

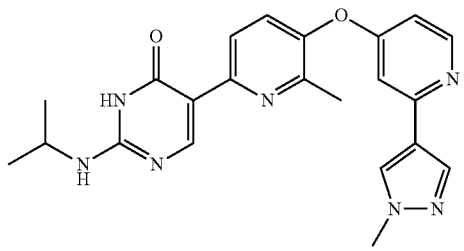 [SMILES: Cc1nc(-c2cnc(NC(C)C)[nH]c2=O)ccc1Oc1ccnc(-c2cnn(C)c2)c1]

Example 3

A solution of Example C2 (0.13 g, 0.309 mmol) in DCM (5 mL) was treated portion-wise with mCPBA (0.09 g, 0.37 mmol), stirred at RT overnight, treated with isopropyl amine (0.5 mL) and stirred at RT overnight. The mixture was treated with satd. NaHCO$_3$, extracted with DCM (2×) and the combined organics were dried over Na$_2$SO$_4$, concentrated to dryness and purified via silica gel chromatography (MeOH/DCM) to obtain N-isopropyl-4-methoxy-5-(6-methyl-5-((2-

(1-methyl-1H-pyrazol-4-yl)pyridin-4-yl)oxy)pyridin-2-yl)pyrimidin-2-amine (63 mg, 47%). MS (ESI) m/z: 432.2 (M+H⁺).

A solution of N-isopropyl-4-methoxy-5-(6-methyl-5-((2-(1-methyl-1H-pyrazol-4-yl)pyridin-4-yl)oxy)pyridin-2-yl)pyrimidin-2-amine (0.063 g, 0.14 mmol) in acetic acid (5 mL) was treated with HBr (0.066 mL, 0.58 mmol), heated at 90° C. for 4 h, cooled to RT and quenched with ice water. The solution was treated with NaHCO₃ and NaCl, extracted with 1:1 THF/EtOAc (3×) and the combined organics were dried over Na₂SO₄ and concentrated to dryness. The material was treated with MeCN (1 mL), allowed to stand at RT and the resulting solid was collected via filtration to afford 2-(isopropylamino)-5-(6-methyl-5-((2-(1-methyl-1H-pyrazol-4-yl)pyridin-4-yl)oxy)pyridin-2-yl)pyrimidin-4(3H)-one (25 mg, 38%). ¹H NMR (400 MHz, DMSO-d₆): δ 10.8 (br s, 1H), 8.68 (s, 1H), 8.36 (d, J=5.7 Hz, 1H), 8.27 (s, 1H), 8.26 (s, 1H), 7.96 (s, 1H), 7.51 (d, J=8.6 Hz, 1H), 7.22 (d, J=2.4 Hz, 1H), 6.67 (br s, 1H), 6.61 (d, J=5.6 Hz, 1H), 4.07 (m, 1H), 3.85 (s, 3H), 2.34 (s, 3H), 1.17 (d, J=6.5 Hz, 6H); MS (ESI) m/z: 418.2 (M+H⁺).

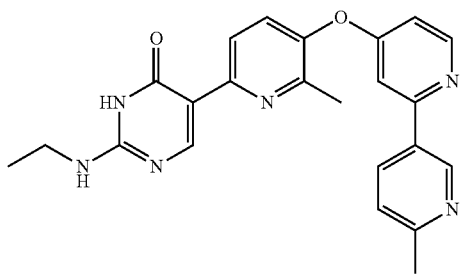 [SMILES: CCNc1ncc(-c2ccc(Oc3ccnc(-c4ccc(C)nc4)c3)c(C)n2)c(=O)[nH]1]

Example 4

A solution of Example C1 (0.15 g, 0.4 mmol) and 2-methyl-5-(4,4,5,5-tetramethyl-1,3,2-dioxaborolan-2-yl)pyridine (0.13 g, 0.57 mmol) in dioxane (4 mL) was sparged with Ar, treated with a solution of K₂CO₃ (0.11 g, 0.8 mmol) in water (1 mL) and heated at 90° C. for 2 h. The mixture was cooled to RT, diluted with water, extracted with EtOAc (3×) and the combined organics were washed with brine, dried over Na₂SO₄, concentrated to dryness and purified by silica gel chromatography (MeOH/DCM) to afford N-ethyl-4-methoxy-5-(6-methyl-5-((6'-methyl-[2,3'-bipyridin]-4-yl)oxy)pyridin-2-yl)pyrimidin-2-amine as an orange foam (0.106 g, 61%). ¹H NMR (400 MHz, DMSO-d₆): δ 9.11 (d, J=2.4 Hz, 1H), 8.74 (s, 1H), 8.54 (d, J=5.7 Hz, 1H), 8.29 (dd, J=8.1, 2.4 Hz, 1H), 7.77 (d, J=8.6 Hz, 1H), 7.65 (d, J=2.4 Hz, 1H), 7.59 (d, J=8.6 Hz, 1H), 7.34 (d, J=8.2 Hz, 1H), 7.02 (d, J=1.9 Hz, 1H), 6.79 (dd, J=5.7, 2.4 Hz, 1H), 3.96 (s, 3H), 3.36-3.34 (m, 2H), 2.51 (s, 3H), 2.38 (s, 3H), 1.15 (s, 3H); MS (ESI) m/z: 429.2 (M+H⁺).

Using the procedure of Example 1, N-ethyl-4-methoxy-5-(6-methyl-5-((6'-methyl-[2,3'-bipyridin]-4-yl)oxy)pyridin-2-yl)pyrimidin-2-amine (0.13 g, 0.3 mmol) and 48% HBr (0.66 mL, 12 mmol) were combined to afford 2-(ethylamino)-5-(6-methyl-5-((6'-methyl-[2,3'-bipyridin]-4-yl)oxy)pyridin-2-yl)pyrimidin-4(3H)-one as a white solid (0.09 g, 73%). ¹H NMR (400 MHz, DMSO-d₆): δ 11.08 (s, 1H), 9.10 (s, 1H), 8.68 (s, 1H), 8.53 (d, J=5.7 Hz, 1H), 8.28 (d, J=8.3 Hz, 2H), 7.62 (s, 1H), 7.54 (d, J=8.7 Hz, 1H), 7.34 (d, J=8.2 Hz, 1H), 6.82 (br s, 1H), 6.78 (d, J=5.7 Hz, 1H), 3.35-3.32 (m, 2H), 2.50 (s, 3H), 2.35 (s, 3H), 1.12 (t, J=7.2 Hz, 3H); MS (ESI) m/z: 415.2 (M+H⁺).

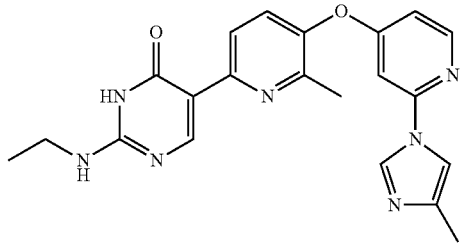 [SMILES: CCNc1ncc(-c2ccc(Oc3ccnc(-n4cnc(C)c4)c3)c(C)n2)c(=O)[nH]1]

Example 5

A mixture of Me₄tBuXPhos (0.018 g, 0.043 mmol) and Pd₂(dba)₃ (0.020 g, 0.022 mmol) in dioxane (1 mL) was sparged with Ar, heated at 100° C. for a few minutes, treated with Example C1 (0.16 g, 0.43 mmol), 4-methyl-1H-imidazole (0.1 g, 1.3 mmol) and K₃PO4 (0.18 g, 0.86 mmol) and heated at 100° C. for 20 h. The mixture was cooled to RT, diluted with EtOAc, the solids removed via filtration through diatomaceous earth and washed with EtOAc. The filtrate was washed with water, then brine, dried over Na₂SO₄, concentrated to dryness and purified by silica gel chromatography (MeOH/DCM) to afford N-ethyl-4-methoxy-5-(6-methyl-5-((2-(4-methyl-1H-imidazol-1-yl)pyridin-4-yl)oxy)pyridin-2-yl)pyrimidin-2-amine as a white solid (0.12 g, 67%). ¹H NMR (400 MHz, DMSO-d₆): δ 8.75 (s, 1H), 8.40 (d, J=1.4 Hz, 1H), 8.32 (d, J=5.8 Hz, 1H), 7.77 (d, J=8.7 Hz, 1H), 7.65 (s, 1H), 7.59 (d, J=8.6 Hz, 1H), 7.49 (br s, 1H), 7.42 (d, J=2.2 Hz, 1H), 6.74 (dd, J=5.8, 2.2 Hz, 1H), 3.96 (s, 3H), 3.36-3.34 (m, 2H), 2.37 (s, 3H), 2.13 (s, 3H), 1.14 (s, 3H); MS (ESI) m/z: 418.2 (M+H⁺).

Using the procedure of Example 1, N-ethyl-4-methoxy-5-(6-methyl-5-((2-(4-methyl-1H-imidazol-1-yl)pyridin-4-yl)oxy)pyridin-2-yl)pyrimidin-2-amine (0.12 g, 0.29 mmol) and 48% HBr (0.63 mL, 11.5 mmol) were combined to afford 2-(ethylamino)-5-(6-methyl-5-((2-(4-methyl-1H-imidazol-1-yl)pyridin-4-yl)oxy)pyridin-2-yl)pyrimidin-4(3H)-one as a white solid (0.06 g, 51%). ¹H NMR (400 MHz, DMSO-d₆): δ 10.60 (br s, 1H), 8.68 (s, 1H), 8.40 (d, J=1.3 Hz, 1H), 8.31-8.30 (m, 2H), 7.64 (s, 1H), 7.54 (d, J=8.6 Hz, 1H), 7.39 (d, J=2.2 Hz, 1H), 6.93 (br s, 1H), 6.73 (dd, J=5.8, 2.2 Hz, 1H), 3.35-3.33 (m, 2H), 2.35 (s, 3H), 2.13 (s, 3H), 1.12 (t, J=7.1 Hz, 3H); MS (ESI) m/z: 404.2 (M+H⁺).

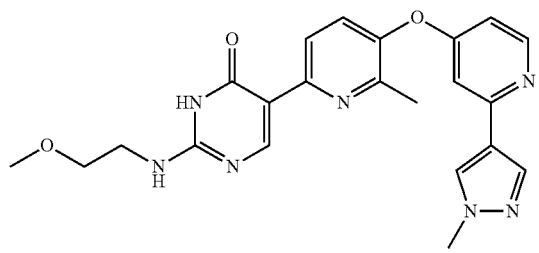 [SMILES: COCCNc1ncc(-c2ccc(Oc3ccnc(-c4cnn(C)c4)c3)c(C)n2)c(=O)[nH]1]

Example 6

A solution of Example C2 (0.15 g, 0.36 mmol) in DCM (5 mL) was treated portion-wise with mCPBA (0.11 g, 0.43 mmol), stirred at RT overnight, treated with 2-methoxyethanamine (0.5 mL) and stirred at RT for 4 h. The mixture was treated with satd. NaHCO₃, extracted with DCM (3×) and the combined organics were dried over Na₂SO₄, concentrated to dryness and purified via silica gel chromatography (MeOH/DCM) to obtain 4-methoxy-N-(2-methoxyethyl)-5-(6-methyl-5-((2-(1-methyl-1H-pyrazol-4-yl)pyridin-4-yl)oxy)pyridin-2-yl)pyrimidin-2-amine (100 mg, 63%). MS (ESI) m/z: 448.2 (M+H+).

A solution of 4-methoxy-N-(2-methoxyethyl)-5-(6-methyl-5-((2-(1-methyl-1H-pyrazol-4-yl)pyridin-4-yl)oxy)pyridin-2-yl)pyrimidin-2-amine (0.10 g, 0.22 mmol) in acetic acid (5 mL) was treated with HBr (0.10 mL, 0.90 mmol), heated at 90° C. for 4 h, cooled to RT and quenched with ice water. The solution was treated with NaHCO$_3$ and NaCl, extracted with EtOAc (3×) and the combined organics were dried over Na$_2$SO$_4$ and concentrated to dryness. The material was treated with MeCN (3 mL) and the resulting solid was collected via filtration to afford 2-((2-methoxyethyl)amino)-5-(6-methyl-5-((2-(1-methyl-1H-pyrazol-4-yl)pyridin-4-yl)oxy)pyridin-2-yl)pyrimidin-4(3H)-one (65 mg, 61%). $^1$H NMR (400 MHz, DMSO-d$_6$): δ 11.02 (br s, 1H), 8.67 (s, 1H), 8.35 (d, J=5.7 Hz, 1H), 8.29-8.23 (m, 2H), 7.96 (d, J=0.7 Hz, 1H), 7.50 (d, J=8.6 Hz, 1H), 7.22 (d, J=2.4 Hz, 1H), 6.85 (br s, 1H), 6.60 (dd, J=5.7, 2.4 Hz, 1H), 3.84 (s, 3H), 3.53-3.44 (m, 4H), 3.28 (s, 3H), 2.34 (s, 3H); MS (ESI) m/z: 434.2 (M+H+).

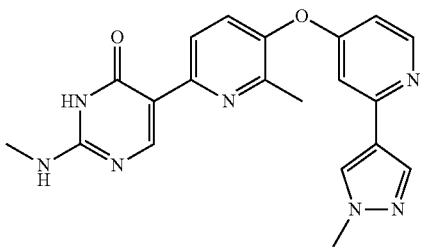 [SMILES: CNc1ncc(-c2ccc(Oc3ccnc(-c4cnn(C)c4)c3)c(C)n2)c(=O)[nH]1]

Example 7

A solution of Example C2 (0.15 g, 0.357 mmol) in DCM (5 mL) was treated portion-wise with mCPBA (0.11 g, 0.43 mmol), stirred at RT overnight, treated with methylamine (2.0M in THF, 3.6 mL, 7.2 mmol) and stirred at RT for 4 h. The mixture was treated with satd. NaHCO$_3$, extracted with DCM (3×) and the combined organics were dried over Na$_2$SO$_4$, concentrated to dryness and purified via silica gel chromatography (MeOH/DCM) to obtain 4-methoxy-N-methyl-5-(6-methyl-5-((2-(1-methyl-1H-pyrazol-4-yl)pyridin-4-yl)oxy)pyridin-2-yl)pyrimidin-2-amine (100 mg, 70%). MS (ESI) m/z: 404.2 (M+H+).

A solution of 4-methoxy-N-methyl-5-(6-methyl-5-((2-(1-methyl-1H-pyrazol-4-yl)pyridin-4-yl)oxy)pyridin-2-yl)pyrimidin-2-amine (0.10 g, 0.25 mmol) in acetic acid (5 mL) was treated with HBr (0.12 mL, 1.0 mmol) and heated at 90° C. for 4 h. The mixture was cooled to RT, quenched with ice water, treated with NaHCO$_3$ and NaCl, and extracted with EtOAc (3×). The combined organics were dried over Na$_2$SO$_4$, concentrated to dryness, the resulting material treated with MeCN (3 mL) and the solid was collected via filtration to afford 5-(6-methyl-5-((2-(1-methyl-1H-pyrazol-4-yl)pyridin-4-yl)oxy)pyridin-2-yl)-2-(methylamino)pyrimidin-4(3H)-one (52 mg, 53%). $^1$H NMR (400 MHz, DMSO-d$_6$): δ 11.26 (s, 1H), 8.70 (s, 1H), 8.36 (d, J=5.7 Hz, 1H), 8.28 (m, 1H), 8.26 (s, 1H), 7.97 (s, 1H), 7.51 (d, J=8.6 Hz, 1H), 7.22 (d, J=2.4 Hz, 1H), 6.70 (br s, 1H), 6.61 (dd, J=5.7, 2.4 Hz, 1H), 3.85 (s, 3H), 2.85 (d, J=4.7 Hz, 3H), 2.35 (s, 3H); MS (ESI) m/z: 390.2 (M+H+).

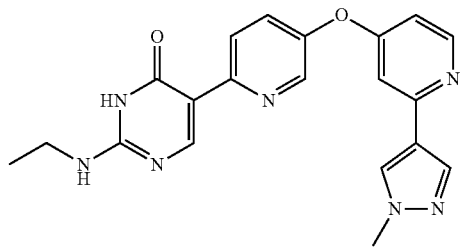 [SMILES: CCNc1ncc(-c2ccc(Oc3ccnc(-c4cnn(C)c4)c3)cn2)c(=O)[nH]1]

Example 8

A mixture of Example B1 (0.20 g, 0.51 mmol), Example A5 (0.17 g, 0.51 mmol) and K$_2$CO$_3$ (0.21 g, 1.52 mmol) in dioxane (6 mL) and water (1.5 mL) was sparged with Ar, treated with Pd(PPh$_3$)$_4$ (0.06 g, 0.051 mmol), sparged again with Ar and heated at 90° C. for 7 h. The mixture was cooled to RT, treated with satd. NaHCO$_3$, extracted with EtOAc (3×) and the combined organics were washed with brine, dried over Na$_2$SO$_4$, concentrated to dryness and purified via silica gel chromatography (EtOAc/Hex) to obtain 5-(5-((2-chloropyridin-4-yl)oxy)pyridin-2-yl)-N-ethyl-4-methoxypyrimidin-2-amine (90 mg, 50%). MS (ESI) m/z: 358.1 (M+H+).

A mixture of 5-(5-((2-chloropyridin-4-yl)oxy)pyridin-2-yl)-N-ethyl-4-methoxypyrimidin-2-amine (0.090 g, 0.25 mmol), 1-methyl-4-(4,4,5,5-tetramethyl-1,3,2-dioxaborolan-2-yl)-1H-pyrazole (0.060 g, 0.28 mmol), and K$_2$CO$_3$ (0.10 g, 0.76 mmol) in 5:1 dioxane/water (6 mL) was sparged with Ar, treated with Pd(PPh$_3$)$_4$ (0.03 g, 0.025 mmol), sparged again with Ar and heated at 90° C. for 7 h. The mixture was cooled to RT, quenched with satd. NaHCO$_3$, extracted with EtOAc (3×) and the combined organics were washed with brine, dried over Na$_2$SO$_4$, concentrated to dryness and purified via silica gel chromatography (MeOH/DCM) to obtain N-ethyl-4-methoxy-5-(5-((2-(1-methyl-1H-pyrazol-4-yl)pyridin-4-yl)oxy)pyridin-2-yl)pyrimidin-2-amine (80 mg, 79%). MS (ESI) m/z: 404.2 (M+H+).

Using the procedure of Example 7, N-ethyl-4-methoxy-5-(5-((2-(1-methyl-1H-pyrazol-4-yl)pyridin-4-yl)oxy)pyridin-2-yl)pyrimidin-2-amine (0.080 g, 0.20 mmol) was combined with acetic acid (3 mL) and HBr (0.090 mL, 0.79 mmol) to afford 2-(ethylamino)-5-(5-((2-(1-methyl-1H-pyrazol-4-yl)pyridin-4-yl)oxy)pyridin-2-yl)pyrimidin-4(3H)-one (40 mg, 51%). $^1$H NMR (400 MHz, DMSO-d$_6$): δ 11.12 (s, 1H), 8.66 (s, 1H), 8.43 (m, 2H), 8.38 (d, J=5.7 Hz, 1H), 8.26 (s, 1H), 7.97 (d, J=0.7 Hz, 1H), 7.62 (dd, J=8.8, 2.9 Hz, 1H), 7.28 (d, J=2.4 Hz, 1H), 63.80 (br s, 1H), 6.72 (dd, J=5.7, 2.4 Hz, 1H), 3.85 (s, 3H), 3.35 (m, 2H), 1.12 (t, J=7.2 Hz, 3H); MS (ESI) m/z: 390.2 (M+H+).

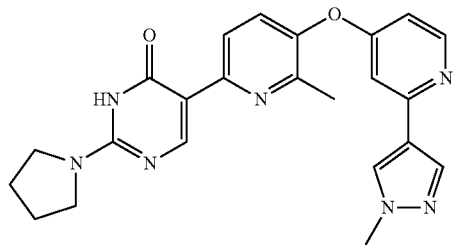 [SMILES: Cc1nc(-c2cnc(N3CCCC3)[nH]c2=O)ccc1Oc1ccnc(-c2cnn(C)c2)c1]

Example 9

A solution of Example C2 (0.15 g, 0.36 mmol) in DCM (5 mL) was treated with mCPBA (0.11 g, 0.43 mmol), stirred at RT for 2 h, treated with pyrrolidine (0.5 mL) and stirred at RT overnight. The mixture was treated with satd. NaHCO$_3$, extracted with DCM (3×) and the combined organics were dried over Na$_2$SO$_4$, concentrated to dryness and purified via silica gel chromatography (MeOH/DCM) to obtain 4-methoxy-5-(6-methyl-5-((2-(1-methyl-1H-pyrazol-4-yl)pyridin-4-yl)oxy)pyridin-2-yl)-2-(pyrrolidin-1-yl)pyrimidine (100 mg, 63%). MS (ESI) m/z: 444.2 (M+H$^+$).

A solution of 4-methoxy-5-(6-methyl-5-((2-(1-methyl-1H-pyrazol-4-yl)pyridin-4-yl)oxy)pyridin-2-yl)-2-(pyrrolidin-1-yl)pyrimidine (0.1 g, 0.22 mmol) in acetic acid (3 mL) was treated with HBr (0.1 mL, 0.90 mmol) and heated at 90° C. for 6.5 h. The mixture was cooled to RT, quenched with ice water, neutralized with NaHCO$_3$ to pH=8 and extracted with EtOAc (3×). The combined organics were dried over Na$_2$SO$_4$, concentrated to dryness, the resulting material treated with MeCN and the solid was collected via filtration to afford 5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one (89 mg, 91%). $^1$H NMR (400 MHz, DMSO-d$_6$): δ 11.21 (s, 1H), 8.73 (s, 1H), 8.36 (d, J=5.7 Hz, 1H), 8.31 (m, 1H), 8.26 (s, 1H), 7.97 (d, J=0.7 Hz, 1H), 7.52 (m, 1H), 7.22 (d, J=2.4 Hz, 1H), 6.61 (d, J=5.6 Hz, 1H), 3.85 (s, 3H), 3.50 (m, 4H), 2.35 (s, 3H), 1.91 (m, 4H); MS (ESI) m/z: 430.2 (M+H$^+$).

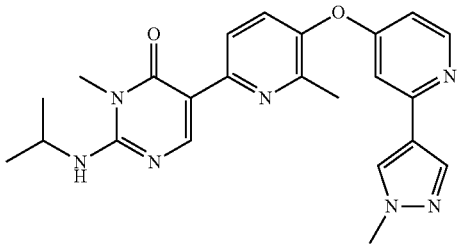 [SMILES: Cc1nc(-c2cnc(NC(C)C)n(C)c2=O)ccc1Oc1ccnc(-c2cnn(C)c2)c1]

Example 10

A mixture of Example C3 (0.14 g, 0.33 mmol) and isopropyl amine (3 mL, 35.0 mmol) was heated at 100° C. for 2 days in a sealed tube. The mixture was cooled to RT, the solid removed via filtration and the filtrate concentrated to dryness and purified via silica gel chromatography to obtain 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one (88 mg, 59%). $^1$H NMR (400 MHz, DMSO-d$_6$): δ 8.68 (s, 1H), 8.36 (d, J=5.7 Hz, 1H), 8.28 (d, J=8.7 Hz, 1H), 8.25 (s, 1H), 7.96 (d, J=0.7 Hz, 1H), 7.52 (d, J=8.6 Hz, 1H), 7.23 (d, J=2.4 Hz, 1H), 7.05 (d, J=7.6 Hz, 1H), 6.60 (dd, J=5.7, 2.4 Hz, 1H), 4.33 (m, 1H), 3.85 (s, 3H), 3.37 (s, 3H), 2.35 (s, 3H), 1.23 (d, J=6.6 Hz, 6H); MS (ESI) m/z: 432.2 (M+H$^+$).

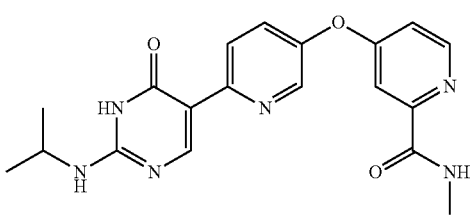 [SMILES: CNC(=O)c1cc(Oc2ccc(-c3cnc(NC(C)C)[nH]c3=O)nc2)ccn1]

Example 11

A suspension of PdCl$_2$(dppf).CH$_2$Cl$_{12}$ (0.048 g, 0.059 mmol), KOAc (0.086 g, 0.879 mmol), bis(pinacolato)diboron (0.186 g, 0.732 mmol), and 5-bromo-N-isopropyl-4-methoxypyrimidin-2-amine (0.144 g, 0.586 mmol) in dioxane (6 mL) was sparged with Ar and heated at 90° C. for 20 h. The mixture was cooled to RT, treated with additional PdCl$_2$(dppf).CH$_2$Cl$_{12}$ (0.048 g, 0.059 mmol), KOAc (0.086 g, 0.879 mmol) and bis(pinacolato)diboron (0.186 g, 0.732 mmol), sparged with Ar and heated at 100° C. for 20 h. The mixture was cooled to RT, treated with Pd(PPh$_3$)$_4$ (0.034 g, 0.029 mmol), K$_2$CO$_3$ (0.121 g, 0.879 mmol), Example A6 (0.104 g, 0.293 mmol) and water (1.5 mL), sparged with Ar, heated at 85° C. for 18 h, then cooled to RT. The mixture was treated with satd. NaHCO$_3$, extracted with EtOAc (4×) and the combined organics were washed with brine, dried over Na$_2$SO$_4$, concentrated to dryness and purified by silica gel chromatography (EtOAc/DCM) to afford 4-((6-(2-(isopropylamino)-4-methoxypyrimidin-5-yl)pyridin-3-yl)oxy)-N-methylpicolinamide (72 mg, 62%). MS (ESI) m/z: 395.2 (M+H$^+$).

A solution of 4-((6-(2-(isopropylamino)-4-methoxypyrimidin-5-yl)pyridin-3-yl)oxy)-N-methylpicolinamide (0.072 g, 0.183 mmol) in DCE (10 mL) was treated with iodotrimethylsilane (0.497 mL, 3.65 mmol), heated at 50° C. for 20 h, treated with additional iodotrimethylsilane (0.25 mL, 1.84 mmol) and heated at 60° C. for 20 h. The mixture was cooled to RT, treated with DCM/THF (5:1), washed with satd. NaHCO$_3$, 10% sodium bisulfite, then brine. The combined aqueous washes were back-extracted with DCM/THF (5:1) (1×) and the combined organics were dried over Na$_2$SO$_4$, concentrated to dryness and purified by preparatory TLC (EtOAc) to afford 4-((6-(2-(isopropylamino)-6-oxo-1,6-dihydropyrimidin-5-yl)pyridin-3-yl)oxy)-N-methylpicolinamide (16 mg, 23%). $^1$H NMR (400 MHz, DMSO-d$_6$): δ 10.89 (br s, 1H), 8.79 (d, J=5.2 Hz, 1H), 8.66 (s, 1H), 8.52 (d, J=5.6 Hz, 1H), 8.47 (d, J=2.9 Hz, 1H), 8.44 (d, J=8.8 Hz, 1H), 7.67 (dd, J=8.8, 2.9 Hz, 1H), 7.42 (d, J=2.6 Hz, 1H), 7.21 (dd, J=5.6, 2.6 Hz, 1H), 6.74 (br s, 1H), 4.08 (m, 1H), 2.77 (d, J=4.8 Hz, 3H), 1.16 (d, J=6.5 Hz, 6H); MS (ESI) m/z: 381.2 (M+H$^+$).

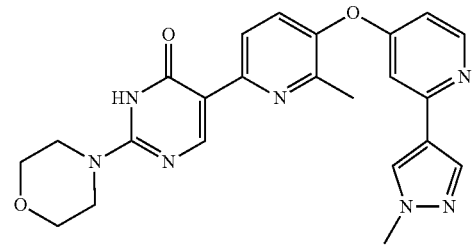 [SMILES: Cc1nc(-c2cnc(N3CCOCC3)[nH]c2=O)ccc1Oc1ccnc(-c2cnn(C)c2)c1]

Example 12

Using the procedure of Example 6, Example C2 (0.15 g, 0.357 mmol), mCPBA (0.106 g, 0.428 mmol) and morpholine (0.5 mL, 5.78 mmol) were combined to afford 4-(4-methoxy-5-(6-methyl-5-((2-(1-methyl-1H-pyrazol-4-yl)pyridin-4-yl)oxy)pyridin-2-yl)pyrimidin-2-yl)morpholine (127 mg, 77%). MS (ESI) m/z: 460.2 (M+H$^+$).

Using the procedure of Example 6, 4-(4-methoxy-5-(6-methyl-5-((2-(1-methyl-1H-pyrazol-4-yl)pyridin-4-yl)oxy)pyridin-2-yl)pyrimidin-2-yl)morpholine (0.127 g, 0.276 mmol)

and HBr (0.126 mL, 1.106 mmol) were combined in acetic acid (3 mL) to afford 5-(6-methyl-5-((2-(1-methyl-1H-pyrazol-4-yl)pyridin-4-yl)oxy)pyridin-2-yl)-2-morpholinopyrimidin-4(3H)-one (75 mg, 59%). $^1$H NMR (400 MHz, DMSO-d$_6$): δ 11.57 (br s, 1H), 8.77 (s, 1H), 8.36 (d, J=5.7 Hz, 1H), 8.27-8.22 (m, 2H), 7.97 (s, 1H), 7.59 (m, 1H), 7.24 (d, J=2.4 Hz, 1H), 6.63 (dd, J=5.7, 2.4 Hz, 1H), 3.84 (s, 3H), 3.68-3.63 (m, 8H), 2.36 (s, 3H); MS (ESI) m/z: 446.2 (M+H$^+$).

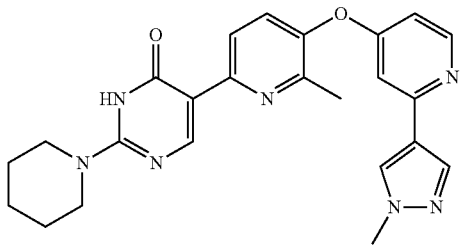 [SMILES: Cc1nc(-c2cnc(N3CCCCC3)[nH]c2=O)ccc1Oc1ccnc(-c2cnn(C)c2)c1]

Example 13

Using the procedure of Example 6, Example C2 (0.15 g, 0.357 mmol), mCPBA (0.106 g, 0.428 mmol) and piperidine (0.6 mL, 6.07 mmol) were combined to afford 4-methoxy-5-(6-methyl-5-((2-(1-methyl-1H-pyrazol-4-yl)pyridin-4-yl)oxy)pyridin-2-yl)-2-(piperidin-1-yl)pyrimidine (134 mg, 82%). MS (ESI) m/z: 458.2 (M+H$^+$).

Using the procedure of Example 6,4-methoxy-5-(6-methyl-5-((2-(1-methyl-1H-pyrazol-4-yl)pyridin-4-yl)oxy)pyridin-2-yl)-2-(piperidin-1-yl)pyrimidine (0.134 g, 0.293 mmol) and HBr (0.133 mL, 1.172 mmol) were combined in acetic acid (3 mL) to afford 4-methoxy-5-(6-methyl-5-((2-(1-methyl-1H-pyrazol-4-yl)pyridin-4-yl)oxy)pyridin-2-yl)-2-(piperidin-1-yl)pyrimidine (103 mg, 79%). $^1$H NMR (400 MHz, DMSO-d$_6$): δ 11.33 (br s, 1H), 8.71 (br s, 1H), 8.35 (d, J=5.7 Hz, 1H), 8.31-8.18 (m, 2H), 7.96 (s, 1H), 7.53 (br s, 1H), 7.23 (d, J=2.4 Hz, 1H), 6.61 (m, 1H), 3.84 (s, 3H), 3.68 (m, 4H), 2.35 (s, 3H), 1.61 (m, 2H), 1.53 (m, 4H); MS (ESI) m/z: 444.2 (M+H$^+$).

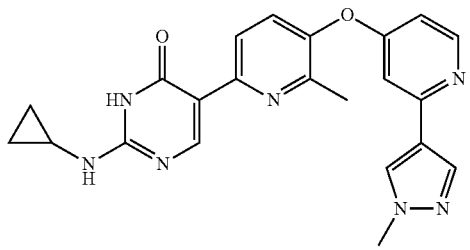 [SMILES: Cc1nc(-c2cnc(NC3CC3)[nH]c2=O)ccc1Oc1ccnc(-c2cnn(C)c2)c1]

Example 14

Using the procedure of Example 6, Example C2 (0.100 g, 0.238 mmol), mCPBA (0.070 g, 0.285 mmol) and cyclopropylamine (0.300 mL, 4.33 mmol) were combined to afford N-cyclopropyl-4-methoxy-5-(6-methyl-5-((2-(1-methyl-1H-pyrazol-4-yl)pyridin-4-yl)oxy)pyridin-2-yl)pyrimidin-2-amine (82 mg, 80%). MS (ESI) m/z: 430.2 (M+H$^+$).

A solution of N-cyclopropyl-4-methoxy-5-(6-methyl-5-((2-(1-methyl-1H-pyrazol-4-yl)oxy)pyridin-2-yl)pyrimidin-2-amine (0.082 g, 0.191 mmol) in acetic acid (2 mL) was treated with HBr (0.087 mL, 0.764 mmol) and heated at 90° C. for 4 h. The mixture was cooled to RT, treated with ice, neutralized with satd. NaHCO3 and extracted with EtOAc (3×). The combined organics were washed with brine, dried over MgSO$_4$, concentrated to dryness, treated with MeCN, sonicated, heated to near-boiling and allowed to stand at RT overnight. The resulting solid was collected via filtration. The combined aqueous washes were filtered, the solid washed with water, dried and combined with the above-isolated solid to afford 2-(cyclopropylamino)-5-(6-methyl-5-((2-(1-methyl-1H-pyrazol-4-yl)pyridin-4-yl)oxy)pyridin-2-yl)pyrimidin-4(3H)-one (35 mg, 44%). $^1$H NMR (400 MHz, DMSO-d$_6$): δ 11.09 (br s, 1H), 8.68 (s, 1H), 8.35 (d, J=5.7 Hz, 1H), 8.28 (m, 1H), 8.25 (s, 1H), 7.96 (d, J=0.8 Hz, 1H), 7.66 (br s, 1H), 7.52 (d, J=8.6 Hz, 1H), 7.22 (d, J=2.4 Hz, 1H), 6.60 (dd, J=5.7, 2.4 Hz, 1H), 3.84 (s, 3H), 2.73-2.68 (m, 1H), 2.34 (s, 3H), 0.75 (m, 2H), 0.55-0.53 (m, 2H); MS (ESI) m/z: 416.2 (M+H$^+$).

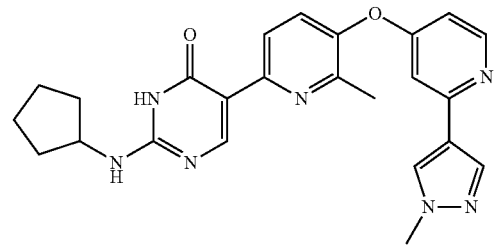 [SMILES: Cc1nc(-c2cnc(NC3CCCC3)[nH]c2=O)ccc1Oc1ccnc(-c2cnn(C)c2)c1]

Example 15

Using the procedure of Example 6, Example C2 (0.100 g, 0.238 mmol), mCPBA (0.070 g, 0.285 mmol) and cyclopentylamine (0.400 mL, 4.04 mmol) were combined to afford N-cyclopentyl-4-methoxy-5-(6-methyl-5-((2-(1-methyl-1H-pyrazol-4-yl)pyridin-4-yl)oxy)pyridin-2-yl)pyrimidin-2-amine (85 mg, 78%). MS (ESI) m/z: 458.2 (M+H$^+$).

Using the procedure of Example 6, N-cyclopentyl-4-methoxy-5-(6-methyl-5-((2-(1-methyl-1H-pyrazol-4-yl)pyridin-4-yl)oxy)pyridin-2-yl)pyrimidin-2-amine (0.085 g, 0.186 mmol) and HBr (0.085 mL, 0.743 mmol) were combined in acetic acid (2 mL) to afford 2-(cyclopentylamino)-5-(6-methyl-5-((2-(1-methyl-1H-pyrazol-4-yl)pyridin-4-yl)oxy)pyridin-2-yl)pyrimidin-4(3H)-one (58 mg, 70%). $^1$H NMR (400 MHz, DMSO-d$_6$): δ 10.78 (br s, 1H), 8.67 (s, 1H), 8.35 (d, J=5.7 Hz, 1H), 8.29-8.23 (m, 2H), 7.96 (s, 1H), 7.50 (d, J=8.6 Hz, 1H), 7.22 (d, J=2.4 Hz, 1H), 6.94 (br s, 1H), 6.60 (dd, J=5.7, 2.4 Hz, 1H), 4.21-4.18 (m, 1H), 3.84 (s, 3H), 2.34 (s, 3H), 1.92-1.89 (m, 2H), 1.68-1.64 (m, 2H), 1.58-1.54 (m, 2H), 1.49-1.40 (m, 2H); MS (ESI) m/z: 444.2 (M+H$^+$).

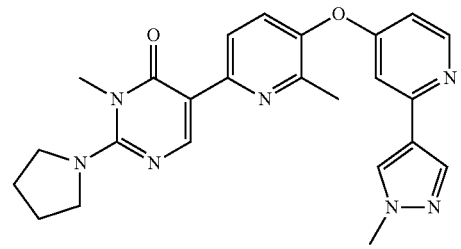 [SMILES: Cc1nc(-c2cnc(N3CCCC3)n(C)c2=O)ccc1Oc1ccnc(-c2cnn(C)c2)c1]

Example 16

A solution of Example C3 (0.087 g, 0.207 mmol) in pyrrolidine (1.75 mL, 21.31 mmol) was heated at 100° C. in a sealed vessel overnight, cooled to RT, concentrated to dryness and purified via silica gel chromatography (EtOAc, MeOH/DCM). The material was treated with MeCN, sonicated and the resulting solid collected via filtration and dried to afford 3-methyl-5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one (62 mg, 67%). $^1$H NMR (400 MHz, DMSO-d$_6$): δ 8.65 (s, 1H), 8.35 (d, J=5.7 Hz, 1H), 8.30 (d, J=8.6 Hz, 1H), 8.25 (s, 1H), 7.96 (s, 1H), 7.54 (d, J=8.6 Hz, 1H), 7.24 (d, J=2.4 Hz, 1H), 6.60 (dd, J=5.7, 2.4 Hz, 1H), 3.84 (s, 3H), 3.58 (m, 4H), 3.45 (s, 3H), 2.35 (s, 3H), 1.87 (m, 4H); MS (ESI) m/z: 444.2 (M+H$^+$).

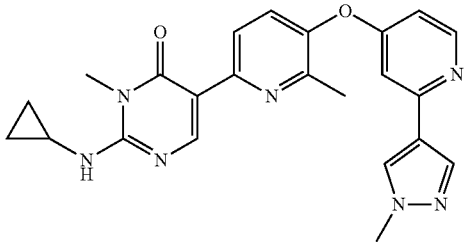 [SMILES: Cc1nc(-c2cnc(NC3CC3)n(C)c2=O)ccc1Oc1ccnc(-c2cnn(C)c2)c1]

Example 17

Using the procedure of Example 16, Example C3 (0.087 g, 0.207 mmol) and cyclopropylamine (1.5 mL, 21.65 mmol) were combined to afford 2-(cyclopropylamino)-3-methyl-5-(6-methyl-5-((2-(1-methyl-1H-pyrazol-4-yl)pyridin-4-yl)oxy)pyridin-2-yl)pyrimidin-4(3H)-one (49 mg, 55%). $^1$H NMR (400 MHz, DMSO-d$_6$): δ 8.70 (s, 1H), 8.35 (d, J=5.7 Hz, 1H), 8.29-8.25 (m, 2H), 7.96 (s, 1H), 7.52 (d, J=8.6 Hz, 1H), 7.48 (d, J=3.1 Hz, 1H), 7.23 (d, J=2.4 Hz, 1H), 6.60 (dd, J=5.7, 2.4 Hz, 1H), 3.84 (s, 3H), 3.33 (s, 3H), 2.88-2.87 (m, 1H), 2.35 (s, 3H), 0.77-0.71 (m, 2H), 0.65-0.61 (m, 2H); MS (ESI) m/z: 430.2 (M+H$^+$).

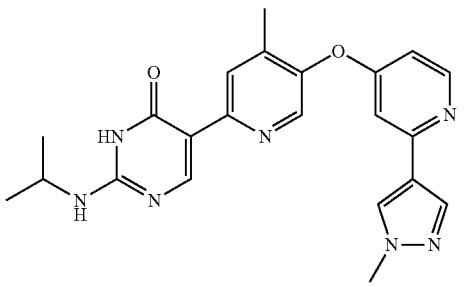 [SMILES: Cc1cc(-c2cnc(NC(C)C)[nH]c2=O)ncc1Oc1ccnc(-c2cnn(C)c2)c1]

Example 18

A solution of Example B3 (0.13 g, 0.44 mmol) in dioxane (4 mL) was treated with Example A3 (0.09 g, 0.26 mmol), Pd(PPh$_3$)$_4$ (0.03 g, 0.026 mmol), a solution of K$_2$CO$_3$ (0.036 g, 0.26 mmol) in water (1 mL) and heated at 90° C. overnight. The mixture was cooled to RT, treated with water, extracted with EtOAc (2×) and the combined organics were washed with brine, dried over Na$_2$SO$_4$, concentrated to dryness and purified by silica gel chromatography (MeOH/DCM) to afford N-isopropyl-4-methoxy-5-(4-methyl-5-((2-(1-methyl-1H-pyrazol-4-yl)pyridin-4-yl)oxy)pyridin-2-yl)pyrimidin-2-amine (55 mg, 49%). $^1$H NMR (400 MHz, DMSO-d$_6$): δ 8.69 (s, 1H), 8.35 (d, J=5.7 Hz, 2H), 8.26 (s, 1H), 7.97 (s, 1H), 7.84 (s, 1H), 7.25 (d, J=2.4 Hz, 1H), 6.59 (dd, J=5.7 Hz, 2.5 Hz, 1H), 4.15-4.12 (m, 1H), 3.97 (s, 3H), 3.84 (s, 3H), 2.17 (s, 3H), 1.175 (d, J=6.4 Hz, 6H); MS (ESI) m/z: 432.2 (M+H$^+$).

Using the procedure of Example 3, N-isopropyl-4-methoxy-5-(4-methyl-5-((2-(1-methyl-1H-pyrazol-4-yl)pyridin-4-yl)oxy)pyridin-2-yl)pyrimidin-2-amine (0.053 g, 0.12 mmol) and HBr (0.2 mL) were combined in acetic acid (3 mL) to afford 2-(isopropylamino)-5-(4-methyl-5-((2-(1-methyl-1H-pyrazol-4-yl)pyridin-4-yl)oxy)pyridin-2-yl)pyrimidin-4(3H)-one (0.03 g, 59%). $^1$H NMR (400 MHz, DMSO-d$_6$): δ 10.86 (s, 1H), 8.65 (s, 1H), 8.34 (m, 2H), 8.30 (s, 1H), 8.25 (s, 1H), 7.96 (s, 1H), 7.21 (d, J=2.4 Hz, 1H), 6.63 (br s, 1H), 6.58 (dd, J=5.7, 2.4 Hz, 1H), 4.09-4.07 (m, 1H), 3.84 (s, 3H), 2.14 (s, 3H), 1.16 (d, J=6.5 Hz, 6H); MS (ESI) m/z: 418.2 (M+H$^+$).

Example 19

A solution of Example C4 in dioxane (3 mL) was treated with acetamide (0.06 g, 1.0 mmol), Cs$_2$CO$_3$ (0.11 g, 0.34 mmol), X-Phos (0.03 g, 0.077 mmol) and Pd$_2$(dba)$_3$ (0.03 g, 0.034 mmol) and heated at 80° C. overnight. The mixture was diluted with EtOAc, the solids removed via filtration through diatomaceous earth, washed with EtOAc and the filtrate was washed with water, then brine, dried over Na$_2$SO$_4$, concentrated to dryness and purified by silica gel chromatography (MeOH/DCM) to afford N-(4-((6-(2-(isopropylamino)-4-methoxypyrimidin-5-yl)-2-methylpyridin-3-yl)oxy)pyridin-2-yl)acetamide (60 mg, 36%).

$^1$H NMR (400 MHz, DMSO-d$_6$): δ 10.56 (s, 1H), 8.73 (s, 1H), 8.18 (d, J=5.7 Hz, 1H), 7.76 (d, J=8.4 Hz, 1H), 7.62 (s, 1H), 7.55 (d, J=8.6 Hz, 1H), 7.44-7.18 (br m, 1H), 6.63 (dd, J=5.7, 2.4 Hz, 1H), 4.10 (m, 1H), 3.95 (s, 3H), 2.33 (s, 3H), 2.02 (s, 3H), 1.17 (d, J=6.4 Hz, 6H); MS (ESI) m/z: 409.2 (M+H$^+$).

A solution of N-(4-((6-(2-(isopropylamino)-4-methoxypyrimidin-5-yl)-2-methylpyridin-3-yl)oxy)pyridin-2-yl)acetamide (0.05 g, 0.12 mmol) in DCE (3 mL) was treated with TMS-I (0.5 mL, 3.67 mmol) and heated at 50° C. for 4 h. The mixture was diluted with 10% Na$_2$S$_2$O$_3$ and 1:1 THF/EtOAc, stirred for few minutes, the layers separated and the aqueous layer extracted with EtOAc (1×). The combined organics were washed with brine, dried over Na$_2$SO$_4$, concentrated to dryness and purified by silica gel chromatography (MeOH/EtOAc) to afford N-(4-((6-(2-(isopropylamino)-4-methoxypyrimidin-5-yl)-2-methylpyridin-3-yl)oxy)pyridin-2-yl)acetamide (0.018 g, 37%). $^1$H NMR (400 MHz, DMSO-d$_6$): δ 10.79 (s, 1H), 10.51 (s, 1H), 8.61 (s, 1H), 8.20 (d, J=8.6 Hz, 1H), 8.12 (d, J=5.7 Hz, 1H), 7.54 (s, 1H), 7.47-7.46 (m 1H), 6.64 (br s, 1H), 6.58 (dd, J=5.8, 2.4 Hz, 1H), 4.03-3.99 (m, 1H), 2.26 (s, 3H), 1.97 (s, 3H), 1.11 (d, J=6.5 Hz, 6H); MS (ESI) m/z: 395.2 (M+H⁺).

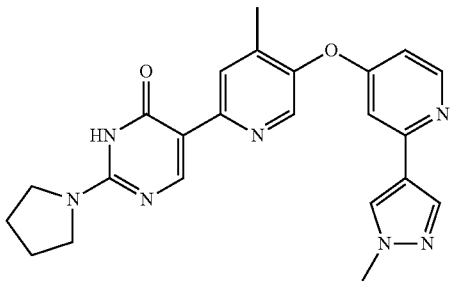 [SMILES: Cc1cc(-c2cnc(N3CCCC3)[nH]c2=O)ncc1Oc1ccnc(-c2cnn(C)c2)c1]

Example 20

A suspension of Example A4 (0.25 g, 0.64 mmol), Example B2 (0.22 g, 0.78 mmol), and K₂CO₃ (0.27 g, 2.0 mmol) in dioxane (5 mL) and water (1 mL) was sparged with Ar, treated with Pd(PPh₃)₄ (0.070 g, 0.061 mmol) and heated at 90° C. for 16 h. The mixture was cooled to RT, treated with satd. NaHCO₃, extracted with EtOAc (4×) and the combined organics were dried over MgSO₄, concentrated to dryness and purified by silica gel chromatography (MeOH/DCM) to afford 4-methoxy-5-(4-methyl-5-((2-(1-methyl-1H-pyrazol-4-yl)pyridin-4-yl)oxy)pyridin-2-yl)-2-(methylthio)pyrimidine (0.28 g, 99%). ¹H NMR (400 MHz, DMSO-d₆): δ 8.89 (s, 1H), 8.47 (s, 1H), 8.37 (d, J=5.7 Hz, 1H), 8.27 (s, 1H), 7.98 (d, J=5.7 Hz, 2H), 7.28 (d, J=2.4 Hz, 1H), 6.63 (dd, J=5.7, 2.5 Hz, 1H), 4.07 (s, 3H), 3.85 (s, 3H), 2.58 (s, 3H), 2.22 (s, 3H); MS (ESI) m/z: 421.1 (M+H⁺).

A solution of 4-methoxy-5-(4-methyl-5-((2-(1-methyl-1H-pyrazol-4-yl)pyridin-4-yl)oxy)pyri-dine-2-yl)-2-(methylthio)pyrimidine (0.28 g, 0.67 mmol) in DCM (10 mL) was treated with mCPBA (0.20 g, 0.80 mmol), stirred at RT for 3 h, treated with pyrrolidine (0.50 mL, 6.1 mmol) and stirred at RT overnight. The mixture was treated with satd. NaHCO₃, extracted with DCM (3×) and the combined organics were dried over MgSO₄, concentrated to dryness and purified by silica gel chromatography (MeOH/DCM) to afford 4-methoxy-5-(4-methyl-5-((2-(1-methyl-1H-pyrazol-4-yl)pyridin-4-yl)oxy)pyridin-2-yl)-2-(pyrrolidin-1-yl)pyrimidine (0.19 g, 64%). ¹H NMR (400 MHz, DMSO-d₆): δ 8.76 (s, 1H), 8.37 (s, 1H), 8.35 (d, J=5.7 Hz, 1H), 8.27 (s, 1H), 7.97 (s, 1H), 7.85 (s, 1H), 7.25 (d, J=2.4 Hz, 1H), 6.60 (dd, J=5.7, 2.5 Hz, 1H), 4.00 (s, 3H), 3.84 (s, 3H), 3.55 (s, 5H), 2.18 (s, 3H), 1.93-1.92 (m, 4H); MS (ESI) m/z: 444.2 (M+H⁺).

A solution of 4-methoxy-5-(4-methyl-5-((2-(1-methyl-1H-pyrazol-4-yl)pyridin-4-yl)oxy)pyridin-2-yl)-2-(pyrroli-din-1-yl)pyrimidine (0.19 g, 0.43 mmol) in acetic acid (2.5 mL) was treated with HBr (48%, 0.10 mL, 1.8 mmol) and heated at 90° C. for 16 h. The mixture was poured onto ice (10 g), neutralized with satd. NaHCO₃, and the resulting solid was collected by filtration, washed with water and MeCN and dried to afford 5-(4-methyl-5-((2-(1-methyl-1H-pyrazol-4-yl)pyridin-4-yl)oxy)pyridin-2-yl)-2-(pyrrolidin-1-yl)pyri-midin-4(3H)-one (0.11 g, 58%). ¹H NMR (400 MHz, DMSO-d₆): δ 11.22 (bs, 1H), 8.68 (s, 1H), 8.38 (s, 1H), 8.34 (d, J=5.7 Hz, 1H), 8.30 (s, 1H), 8.26 (s, 1H), 7.96 (s, 1H), 7.22 (d, J=2.4 Hz, 1H), 6.58 (m, 1H), 3.84 (s, 3H), 3.50 (bs, 4H), 2.15 (s, 3H), 1.91 (bs, 4H); MS (ESI) m/z: 430.2 (M+H⁺).

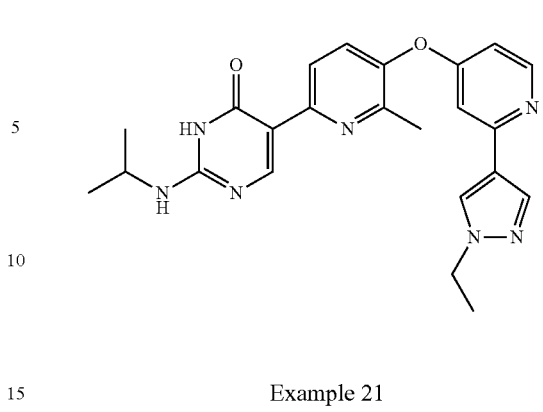

Example 21

Example C4 (0.30 g, 0.778 mmol), 1-ethyl-4-(4,4,5,5-tet-ramethyl-1,3,2-dioxaborolan-2-yl)-1H-pyrazole (0.19 g, 0.85 mmol), and potassium carbonate (0.32 g, 2.33 mmol) were combined in the mixture of dioxane:H2) (4:1, 10 mL). The mixture was sparge with Ar and then tetrakis(triph-enylphosphine)Palladium(0) (0.090 g, 0.078 mmol) was added. The mixture was sparge with Ar again and heated at 90° C. overnight. The mixture was quenched with NaHCO₃ and extracted with EtOAc (3×). The organic was dried over Na₂SO₄, filtered and concentrated to obtain the crude. The crude was purified via silica gel chromatography (EtOAc/hexane) to obtain 5-(5-((2-(1-ethyl-1H-pyrazol-4-yl)pyridin-4-yl)oxy)-6-methylpyridin-2-yl)-N-isopropyl-4-methoxy-pyrimidin-2-amine (0.25 g, 72.2% yield). ¹H NMR (400 MHz, DMSO-d₆): δ 8.75 (s, 1H), 8.37 (d, J=5.7 Hz, 1H), 8.32 (s, 1H), 7.99 (s, 1H), 7.77 (m, 1H), 7.56 (d, J=8.6 Hz, 1H), 7.27 (d, J=2.4 Hz, 1H), 6.61 (dd, J=5.7, 2.4 Hz, 1H), 4.14 (q, J=7.3 Hz, 2H), 4.01 (s, 1H), 3.95 (m, 3H), 2.37 (s, 3H), 1.38 (t, J=7.3 Hz, 3H), 1.18 (d, J=6.5 Hz, 6H); MS (ESI) m/z: 446.3 (M+H⁺).

5-(5-((2-(1-ethyl-1H-pyrazol-4-yl)pyridin-4-yl)oxy)-6-methylpyridin-2-yl)-N-isopropyl-4-methoxypyrimidin-2-amine (0.25 g, 0.56 mmol) was dissolved in AcOH (5 mL) and 48% hydrobromic acid (0.25 mL, 2.24 mmol) was added. The mixture was heated at 90° C. for 5 hours. The mixture was evaporated under high vacuum. The residue was treated with NaHCO₃ solution and the solution was extracted with EtOAc (3×). The organic was dried over Na₂SO₄, filtered, and concentrated. The residue was treated with hot MeCN. The solid was filtered, and dried under vacuum to obtain 5-(5-((2-(1-ethyl-1H-pyrazol-4-yl)pyridin-4-yl)oxy)-6-methylpyridin-2-yl)-2-(isopropylamino)pyrimidin-4(3H)-one (185 mg, 73.1% yield). ¹H NMR (400 MHz, DMSO-d₆): δ 10.81 (s, 1H), 8.68 (s, 1H), 8.36 (d, J=5.7 Hz, 1H), 8.31 (s, 1H), 8.26 (d, J=8.6 Hz, 1H), 7.98 (s, 1H), 7.51 (d, J=8.6 Hz, 1H), 7.24 (d, J=2.4 Hz, 1H), 6.60 (dd, J=5.7, 2.4 Hz, 1H), 4.14 (q, J=7.3 Hz, 2H), 4.07 (m, 1H), 2.34 (s, 3H), 1.37 (t, J=7.3 Hz, 3H), 1.17 (d, J=6.5 Hz, 6H); MS (ESI) m/z: 432.2 (M+H⁺).

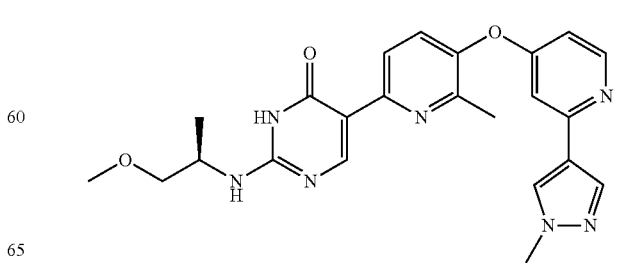

Example 22

Example C2 (0.15 g, 0.36 mmol) was dissolved in DCM (5 mL) and then mCPBA (0.11 g, 0.43 mmol) was added portion wise. The mixture was stirred at RT for 3 hours. (S)-(+)-1-methoxy-2-propylamine (0.45 mL) was added and the mixture was stirred at RT for 2 days. The mixture was quenched with NaHCO$_3$ solution and the solution was extracted with DCM (2×). The organic was dried over Na$_2$SO$_4$, filtered and concentrated to obtain the crude. The material was purified via silica gel chromatography (MeOH/DCM) to obtain (R)-4-methoxy-N-(1-methoxypropan-2-yl)-5-(6-methyl-5-((2-(1-methyl-1H-pyrazol-4-yl)pyridin-4-yl)oxy)pyridin-2-yl)pyrimidin-2-amine (98 mg, 59.5% yield). MS (ESI) m/z: 462.2 (M+H$^+$).

(R)-4-methoxy-N-(1-methoxypropan-2-yl)-5-(6-methyl-5-((2-(1-methyl-1H-pyrazol-4-yl)pyridin-4-yl)oxy)pyridin-2-yl)pyrimidin-2-amine (98 mg, 0.21 mmol) was dissolved in AcOH (3 mL) and then hydrobromic acid (0.1 mL, 0.85 mmol) was added. The mixture was heated at 90° C. for 3.5 hours. The mixture was concentrated and the residue was treated with NaHCO$_3$ solution. The solution was extracted with EtOAc (3×). The organic was washed with NaHCO$_3$, dried over Na$_2$SO$_4$, filtered and concentrated to obtain the crude. The crude was treated with hot MeCN and kept at RT. The solid was filtered and washed with MeCN and dried under vacuum to obtain (R)-2-((1-methoxypropan-2-yl)amino)-5-(6-methyl-5-((2-(1-methyl-1H-pyrazol-4-yl)pyridin-4-yl)oxy)pyridin-2-yl)pyrimidin-4(3H)-one (67 mg, 59.2% yield). $^1$H NMR (400 MHz, DMSO-d$_6$): δ 10.85 (s, 1H), 8.67 (s, 1H), 8.36 (d, J=5.7 Hz, 1H), 8.25 (m, 2H), 7.97 (s, 1H), 7.51 (d, J=8.6 Hz, 1H), 7.23 (d, J=2.4 Hz, 1H), 6.75 (br s, 1H), 6.60 (dd, J=5.7, 2.4 Hz, 1H), 4.19 (m, 1H), 3.85 (s, 3H), 3.38 (m, 2H), 3.30 (s, 3H), 2.34 (s, 3H), 1.15 (d, J=6.7 Hz, 3H); MS (ESI) m/z: 448.2 (M+H$^+$).

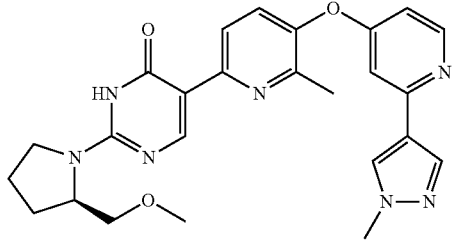 [SMILES: COC[C@H]1CCCN1c1ncc(-c2ccc(Oc3ccnc(-c4cnn(C)c4)c3)c(C)n2)c(=O)[nH]1]

Example 23

Example C2 (0.10 g, 0.24 mmol) was dissolved in DCM (5 mL) and then mCPBA (60 mg, 0.24 mmol) was added portion wise. The mixture was stirred at RT mfor 2 hours. (R)-2-(methoxymethyl)pyrrolidine (0.28 g, 2.38 mmol) was added and then the mixture was stirred at RT overnight. The mixture was quenched with NaHCO$_3$ solution and the solution was extracted with DCM (2×). The organic was dried over Na$_2$SO$_4$, filtered and concentrated to obtain the crude. The material was purified via silica gel chromatography (MeOH/DCM) to obtain (R)-4-methoxy-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidine (96 mg, 83% yield). MS (ESI) m/z: 488.3 (M+H$^+$).

(R)-4-methoxy-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidine (96 mg, 0.20 mmol) was dissolved in AcOH (3 mL) and then 48% hydrobromic acid (0.1 mL) was added. The mixture was heated at 90° C. FOR 3.5 hours. The mixture was concentrated and the residue was treated with NaHCO$_3$ solution. The solution was extracted with EtOAc (3×) and the organic was washed with NaHCO$_3$, dried over Na$_2$SO$_4$, filtered and concentrated to obtain the crude. The material was treated with ether and sonicated. The solid was filtered, washed with ether and dried under vacuum to obtain (R)-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidin-4(3H)-one (58 mg, 60.1% yield). $^1$H NMR (400 MHz, DMSO-d$_6$): δ 11.15 (br s, 1H), 8.73 (s, 1H), 8.36 (d, J=5.7 Hz, 1H), 8.28 (br s, 1H), 8.26 (s, 1H), 7.97 (s, 1H), 7.53 (m, 1H), 7.23 (d, J=2.4 Hz, 1H), 6.62 (m, 1H), 4.34 (m, 1H), 3.85 (s, 3H), 3.52-3.40 (m, 4H), 3.28 (s, 3H), 2.35 (s, 3H), 1.95 (br d, J=27.5 Hz, 4H); MS (ESI) m/z: 474.3 (M+H$^+$).

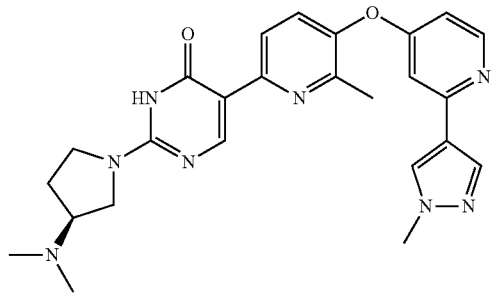 [SMILES: Cc1nc(-c2cnc(N3CC[C@H](N(C)C)C3)[nH]c2=O)ccc1Oc1ccnc(-c2cnn(C)c2)c1]

Example 24

Example C2 (0.10 g, 0.24 mmol) was dissolved in DCM (5 mL) and then mCPBA (60 g, 0.24 mmol) was added. The mixture was stirred at RT for 2.5 hours. (3S)-(−)-3-(dimethylamino)pyrrolidine (0.27 g, 2.37 mmol) was added and then the mixture was stirred at RT overnight. The mixture was quenched with NaHCO$_3$ and extracted with DCM (2×). The organic was dried over Na$_2$SO$_4$, filtered and concentrated to obtain the crude. The material was purified via silica gel chromatography (MeOH/DCM) to obtain (S)-1-(4-methoxy-5-(6-methyl-5-((2-(1-methyl-1H-pyrazol-4-yl)pyridin-4-yl)oxy)pyridin-2-yl)pyrimidin-2-yl)-N,N-dimethylpyrrolidin-3-amine (100 mg, 86% yield). MS (ESI) m/z: 487.3 (M+H$^+$).

(S)-1-(4-methoxy-5-(6-methyl-5-((2-(1-methyl-1H-pyrazol-4-yl)pyridin-4-yl)oxy)pyridin-2-yl)pyrimidin-2-yl)-N,N-dimethylpyrrolidin-3-amine (0.10 g, 0.21 mmol) was dissolved in AcOH (3 mL) and then 48% hydrobromic acid (0.1 mL) was added. The mixture was heated at 90° C. for 3.5 hours. The mixture was concentrated and the residue was treated with NaHCO$_3$ solution. The solution was extracted with EtOAc (3×) and the organic was washed with NaHCO$_3$, dried over Na$_2$SO$_4$, filtered and concentrated to obtain the crude. The crude was treated with hot MeCN and kept at RT. The solid was filtered, washed with MeCN, and dried under vacuum to obtain (S)-2-(3-(dimethylamino)pyrrolidin-1-yl)-5-(6-methyl-5-((2-(1-methyl-1H-pyrazol-4-yl)pyridin-4-yl)oxy)pyridin-2-yl)pyrimidin-4(3H)-one (62 mg, 62.8% yield). $^1$H NMR (400 MHz, DMSO-d$_6$): δ 8.73 (s, 1H), 8.36 (d, J=5.7 Hz, 1H), 8.29 (m, 1H), 8.26 (s, 1H), 7.97 (s, 1H), 7.53 (d, J=8.6 Hz, 1H), 7.23 (d, J=2.4 Hz, 1H), 6.62 (dd, J=5.7, 2.4 Hz, 1H), 3.85 (s, 3H), 3.74 (m, 2H), 3.44 (m, 1H), 3.31 (s, 3H), 3.22 (m, 1H), 2.75 (m, 1H), 2.35 (s, 3H), 2.18 (s, 6H), 2.11 (m, 1H), 1.77 (m, 1H) one proton is missing; MS (ESI) m/z: 473.3 (M+H$^+$).

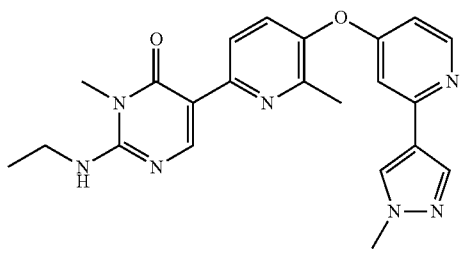 [SMILES: CCNc1ncc(-c2ccc(Oc3ccnc(-c4cnn(C)c4)c3)c(C)n2)c(=O)n1C]

Example 25

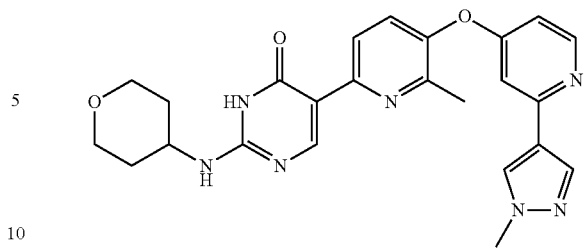

Example 27

To a microwave vessel, Example C3 (0.11 g, 0.26 mmol) was added and then 2.0Methylamine in THF (10 mL, 20.00 mmol) was added. The mixture was heated at 100° C. for 2 days. The mixture was concentrated to obtain the crude. The crude was purified via silica gel chromatography (MeOH/DCM) to obtain 2-(ethylamino)-3-methyl-5-(6-methyl-5-((2-(1-methyl-1H-pyrazol-4-yl)pyridin-4-yl)oxy)pyridin-2-yl)pyrimidin-4(3H)-one (90 mg, 82% yield). $^1$H NMR (400 MHz, DMSO-d$_6$): δ 8.69 (s, 1H), 8.39 (d, J=5.9 Hz, 1H), 8.29 (m, 2H), 8.01 (s, 1H), 7.56 (m, 2H), 7.30 (br s, 1H), 6.68 (br s, 1H), 3.86 (s, 3H), 3.45 (m, 2H), 3.36 (s, 4H), 2.36 (s, 3H), 1.18 (t, J=7.1 Hz, 3H); MS (ESI) m/z: 418.2 (M+H$^+$).

A solution of Example C2 (0.200 g, 0.476 mmol) in DCM (5 mL) was treated with mCPBA (0.141 g, 0.571 mmol), stirred at RT for 3 h, treated with 4-aminotetrahydropyran hydrochloride (0.524 g, 3.81 mmol) and TEA (0.530 mL, 3.81 mmol) and stirred at RT overnight. Additional 4-aminotetrahydropyran hydrochloride (0.524 g, 3.81 mmol) and TEA (0.530 mL, 3.81 mmol) were added and the mixture stirred at RT for an additional 24 h. The mixture was concentrated to dryness, transferred to a sealed vessel with DMF (10 mL), treated with additional 4-aminotetrahydropyran hydrochloride (0.524 g, 3.81 mmol) and TEA (0.530 mL, 3.81 mmol) and heated at 60° C. overnight. The mixture was cooled to RT, the solids removed via filtration and washed with DCM. The filtrate was treated with satd. NaHCO$_3$, extracted with DCM (3×) and the combined organics were washed with 5% LiCl (3×), then brine, dried over Na$_2$SO$_4$, concentrated to dryness and purified via silica gel chromatography (MeOH/DCM) to afford 4-methoxy-5-(6-methyl-5-((2-(1-methyl-1H-pyrazol-4-yl)pyridin-4-yl)oxy)pyridin-2-yl)-N-(tetrahydro-2H-pyran-4-yl)pyrimidin-2-amine (125 mg, 56%). MS (ESI) m/z: 474.2 (M+H$^+$).

A solution of 4-methoxy-5-(6-methyl-5-((2-(1-methyl-1H-pyrazol-4-yl)pyridin-4-yl)oxy)pyridin-2-yl)-N-(tetrahydro-2H-pyran-4-yl)pyrimidin-2-amine (0.125 g, 0.264 mmol) in DCE (3 mL) was treated with TMS-I (1.078 mL, 7.92 mmol), heated at 60° C. for 5 h, then cooled to RT and stirred overnight. The mixture was treated with 10% Na$_2$S$_2$O$_3$ and 1:1 THF/EtOAc, stirred for 0.5 h, the layers separated, the aqueous layer extracted with EtOAc (1×) and the combined organics were washed with brine, dried over MgSO$_4$ and concentrated to dryness. The material was treated with MeCN, heated to near-reflux and allowed to stand at RT over the weekend. The solid was removed via filtration, the filtrate concentrated to dryness and purified via silica gel chromatography (MeOH/EtOAc). The resulting material was treated with 10% MeOH/DCM, filtered to remove solids and concentrated to dryness to afford 5-(6-methyl-5-((2-(1-methyl-1H-pyrazol-4-yl)pyridin-4-yl)oxy)pyridin-2-yl)-2-((tetrahydro-2H-pyran-4-yl)amino)pyrimidin-4(3H)-one (7.7 mg, 6%). $^1$H NMR (400 MHz, DMSO-d$_6$): δ10.96 (br s, 1H), 8.67 (s, 1H), 8.35 (d, J=5.7 Hz, 1H), 8.29-8.24 (m, 2H), 7.96 (s, 1H), 7.51 (d, J=8.6 Hz, 1H), 7.22 (d, J=2.4 Hz, 1H), 7.00 (br s, 1H), 6.60 (dd, J=5.7, 2.4 Hz, 1H), 3.98 (m, 1H), 3.87-3.80 (m, 5H), 3.39 (m, 2H), 2.34 (s, 3H), 1.85 (m, 2H), 1.47 (m, 2H); MS (ESI) m/z: 460.2 (M+H$^+$).

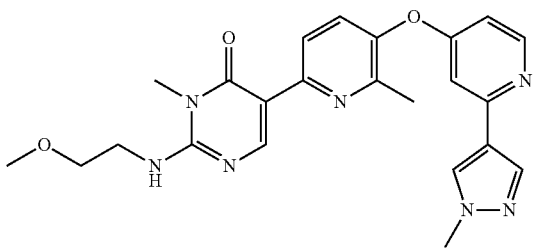 [SMILES: COCCNc1ncc(-c2ccc(Oc3ccnc(-c4cnn(C)c4)c3)c(C)n2)c(=O)n1C]

Example 26

To a microwave vessel, Example C3 (0.11 g, 0.26 mmol) was added and then 2-methoxyethanamine (3 mL, 34.5 mmol) was added. The mixture was heated at 100° C. for 2 days. The mixture was concentrated to obtain the crude. The crude was purified via silica gel chromatography (MeOH/DCM) to obtain 2-((2-methoxyethyl)amino)-3-methyl-5-(6-methyl-5-((2-(1-methyl-1H-pyrazol-4-yl)pyridin-4-yl)oxy)pyridin-2-yl)pyrimidin-4(3H)-one (98 mg, 84% yield). $^1$H NMR (400 MHz, DMSO-d$_6$): δ 8.68 (s, 1H), 8.37 (d, J=5.8 Hz, 1H), 8.28 (m, 2H), 7.99 (s, 1H), 7.57 (t, J=5.6 Hz, 1H), 7.54 (d, J=8.6 Hz, 1H), 7.27 (s, 1H), 6.64 (m, 1H), 3.85 (s, 3H), 3.56-3.54 (m, 4H), 3.37 (s, 3H), 3.28 (s, 3H), 2.35 (s, 3H); MS (ESI) m/z: 448.2 (M+H$^+$).

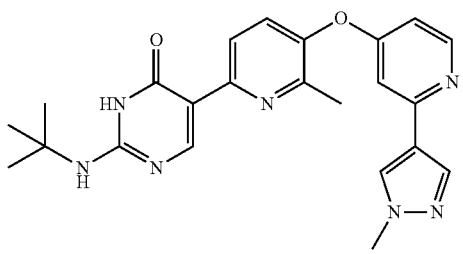 [SMILES: Cc1nc(-c2cnc(NC(C)(C)C)[nH]c2=O)ccc1Oc1ccnc(-c2cnn(C)c2)c1]

Example 28

A solution of Example C2 (0.100 g, 0.238 mmol) in DCM (5 mL) was treated with mCPBA (0.059 g, 0.238 mmol), stirred at RT for 2 h, treated with t-butylamine (0.4 mL, 3.81 mmol) and stirred at RT overnight. Additional t-butylamine (0.4 mL, 3.81 mmol) was added and the mixture stirred at RT for an additional 24 h. The mixture was concentrated to dryness, transferred to a sealed vessel with DMF (5 mL), treated with additional t-butylamine (0.4 mL, 3.81 mmol) and heated at 60° C. overnight. The mixture was cooled to RT, the solids removed via filtration and washed with DCM. The filtrate was treated with satd. NaHCO$_3$, extracted with DCM (3×) and the combined organics were washed with 5% LiCl (3×), then brine, dried over Na$_2$SO$_4$, concentrated to dryness and purified via silica gel chromatography (MeOH/DCM) to afford N-(tert-butyl)-4-methoxy-5-(6-methyl-5-((2-(1-methyl-1H-pyrazol-4-yl)pyridin-4-yl)oxy)pyridin-2-yl)pyrimidin-2-amine (69 mg, 65%). MS (ESI) m/z: 446.3 (M+H$^+$).

A solution of N-(tert-butyl)-4-methoxy-5-(6-methyl-5-((2-(1-methyl-1H-pyrazol-4-yl)pyridin-4-yl)oxy)pyridin-2-yl)pyrimidin-2-amine (0.069 g, 0.155 mmol) in acetic acid (1.5 mL) was treated with HBr (48% aq., 0.071 mL, 0.623 mmol) and heated at 90° C. for 4 h. The mixture was removed from heat, treated with ice and EtOAc, neutralized with satd. NaHCO$_3$, extracted with 1:1 EtOAc/THF (3×) and the combined organics were washed with brine, dried over MgSO$_4$ and concentrated to dryness. The resulting material was treated with MeCN, heated to near-reflux and allowed to stand at RT overnight. The solid was removed via filtration and the filtrate was concentrated to dryness and purified twice via silica gel chromatography (MeOH/DCM, then MeOH/EtOAc) to afford 2-(tert-butylamino)-5-(6-methyl-5-((2-(1-methyl-1H-pyrazol-4-yl)pyridin-4-yl)oxy)pyridin-2-yl)pyrimidin-4(3H)-one (11 mg, 15%). $^1$H NMR (400 MHz, DMSO-d$_6$): δ 10.59 (s, 1H), 8.67 (s, 1H), 8.37 (d, J=5.6 Hz, 1H), 8.27-8.22 (m, 2H), 7.97 (s, 1H), 7.52 (d, J=8.9 Hz, 1H), 7.23 (d, J=2.6 Hz, 1H), 6.60 (dd, J=6.1, 2.6 Hz, 1H), 6.52 (s, 1H), 3.84 (s, 3H), 2.34 (s, 3H), 1.41 (s, 9H); MS (ESI) m/z: 432.2 (M+H$^+$).

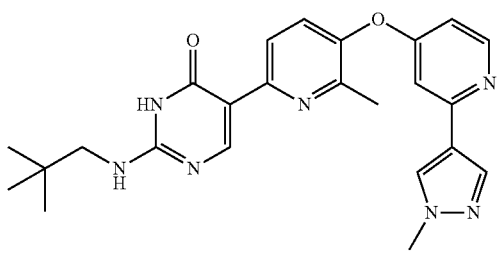 [SMILES: Cc1nc(-c2cnc(NCC(C)(C)C)[nH]c2=O)ccc1Oc1ccnc(-c2cnn(C)c2)c1]

Example 29

A solution of 2,2,2-trimethylacetamide (1.0 g, 9.89 mmol) in THF (100 mL) was treated slowly with LiAlH$_4$ (2.0M in THF, 14.83 mL, 29.7 mmol) and stirred at RT under Ar overnight. The mixture was slowly quenched with water (1.125 mL), 20% KOH (1.125 mL) and water (2.25 mL), stirred vigorously for 10 min, treated with Na$_2$SO$_4$, the solids removed via filtration through celite and the filter pad washed with THF. The filtrate was treated with 1M HCl in MeOH (15 mL) and concentrated to dryness to afford 2,2-dimethylpropan-1-amine hydrochloride (413 mg, 34%). $^1$H NMR (400 MHz, DMSO-d$_6$): δ 7.88 (br s, 2H), 2.57 (s, 2H), 0.93 (s, 9H).

A solution of Example C2 (0.100 g, 0.238 mmol) in DCM (5 mL) was treated with mCPBA (0.059 g, 0.238 mmol), stirred at RT for 2 h, treated with 2,2-dimethylpropan-1-amine hydrochloride (0.410 g, 3.32 mmol) and TEA (0.464 mL, 3.33 mmol) and stirred at RT for 5 days. The mixture was treated with satd. NaHCO$_3$, extracted with DCM (3×) and the combined organics were dried over Na$_2$SO$_4$, concentrated to dryness and purified via silica gel chromatography (MeOH/DCM) to afford 4-methoxy-5-(6-methyl-5-((2-(1-methyl-1H-pyrazol-4-yl)pyridin-4-yl)oxy)pyridin-2-yl)-N-neopentylpyrimidin-2-amine (81 mg, 74%). MS (ESI) m/z: 460.3 (M+H$^+$).

A solution of 4-methoxy-5-(6-methyl-5-((2-(1-methyl-1H-pyrazol-4-yl)pyridin-4-yl)oxy)pyridin-2-yl)-N-neopentylpyrimidin-2-amine (0.081 g, 0.176 mmol) in acetic acid (2 mL) was treated with HBr (48% aq, 0.080 mL, 0.705 mmol), heated at 80° C. for 6 h, then cooled to RT overnight. The mixture was treated with ice and EtOAc, neutralized with satd. NaHCO$_3$, extracted with EtOAc (3×) and the combined organics were washed with brine, dried over MgSO$_4$ and concentrated to dryness. The material was suspended in MeCN, heated to near-reflux and allowed to stand at RT for 3 h. The resulting solid was collected via filtration to afford 5-(6-methyl-5-((2-(1-methyl-1H-pyrazol-4-yl)pyridin-4-yl)oxy)pyridin-2-yl)-2-(neopentylamino)pyrimidin-4(3H)-one (44 mg, 56%). $^1$H NMR (400 MHz, DMSO-d$_6$): δ 10.84 (s, 1H), 8.68 (s, 1H), 8.35 (d, J=6.6 Hz, 1H), 8.28-8.23 (m, 2H), 7.96 (s, 1H), 7.52 (d, J=8.6 Hz, 1H), 7.22 (d, J=3.0 Hz, 1H), 6.73 (br s, 1H), 6.60 (dd, J=5.1, 2.3 Hz, 1H), 3.86 (s, 3H), 3.22 (d, J=6.2 Hz, 2H), 2.34 (s, 3H), 0.91 (s, 9H); MS (ESI) m/z: 446.2 (M+H$^+$).

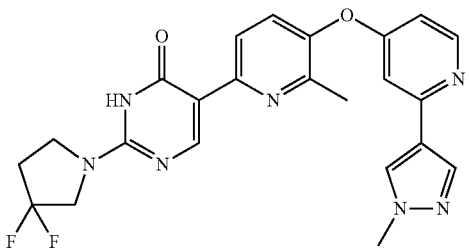 [SMILES: Cc1nc(-c2cnc(N3CCC(F)(F)C3)[nH]c2=O)ccc1Oc1ccnc(-c2cnn(C)c2)c1]

Example 30

Example C2 (0.10 g, 0.24 mmol) was dissolved in DCM (5 mL) and then mCPBA (60 mg, 0.24 mmol) was added portion wise. The mixture was stirred at RT for 5 days (the reaction was very slow). The mixture was transferred to microwave vessel and heated at 40° C. for 2 days. The mixture was quenched with NaHCO$_3$ and the solution was extracted with DCM (2×). The organic was dried over Na$_2$SO$_4$, filtered and concentrated to obtain the crude. The material was purified via silica gel chromatography (MeOH/DCM) to obtain 2-(3,3-difluoropyrrolidin-1-yl)-4-methoxy-5-(6-methyl-5-((2-(1-methyl-1H-pyrazol-4-yl)pyridin-4-yl)oxy)pyridin-2-yl)pyrimidine (80 mg, 70% yield). MS (ESI) m/z: 480.2 (M+H$^+$).

A solution of 2-(3,3-difluoropyrrolidin-1-yl)-4-methoxy-5-(6-methyl-5-((2-(1-methyl-1H-pyrazol-4-yl)pyridin-4-yl)oxy)pyridin-2-yl)pyrimidine (0.080 g, 0.167 mmol) in AcOH (3 mL) was treated with 48% hydrobromic acid (0.1 mL). The mixture was heated at 90° C. for 3 hours. The mixture was concentrated and the residue was treated with NaHCO$_3$ and EtOAc. The mixture was stirred at RT. The solid was filtered and washed with water, EtOAc, and dried under vacuum to obtain 2-(3,3-difluoropyrrolidin-1-yl)-5-(6-methyl-5-((2-(1-methyl-1H-pyrazol-4-yl)pyridin-4-yl)oxy)pyridin-2-yl)pyrimidin-4(3H)-one (42 mg, 52.3% yield). $^1$H NMR (400 MHz, DMSO-d$_6$): δ 8.76 (br s, 1H), 8.36 (d, J=5.7 Hz, 1H), 8.28 (br s, 1H), 8.27 (s, 1H), 7.97 (s, 1H), 7.58 (br s, 1H), 7.24 (d, J=2.4 Hz, 1H), 6.64 (s, 1H), 3.96 (m, 2H), 3.85 (s, 3H), 3.76 (m, 2H), 2.54 (m, 2H), 2.37 (s, 3H), one proton is missing; MS (ESI) m/z: 466.2 (M+H$^+$).

The following assays demonstrate that certain compounds of Formula I inhibit kinase activity of c-FMS kinase, c-KIT kinase, or PDGFRβ kinase in enzymatic assays and also inhibit the activity of c-FMS kinase in M-NFS-60 and THP-1 cell lines. In vivo evaluations of certain compounds of Formula I also demonstrate inhibition of c-FMS in a pharmcodynamic model or also exhibit efficacy in a peritibial implant model, a U-251 or GL-261 glioma model, or in a MDA-MB-231 breast cancer xenograft model.

uFMS Kinase (Seq. ID No. 1) Assay

Activity of unphosphorylated c-FMS kinase (uFMS, Seq. ID no. 1) was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophotometrically. The reaction mixture (100 μL) contained FMS (purchased from Millipore) (10 nM), polyE4Y (1 mg/mL), MgCl$_2$ (10 mM), pyruvate kinase (4 units), lactate dehydrogenase (0.7 units), phosphoenol pyruvate (1 mM), NADH (0.28 mM) and ATP (500 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). IC$_{50}$ values were calculated from a series of percent inhibition values determined at a range of inhibitor concentrations using software routines as implemented in the GraphPad Prism software package.

```
uFMS Kinase sequence (Y538-end) used for screening
                                      (Seq. ID No. 1)
YKYKQKPKYQ VRWKIIESYE GNSYTFIDPT QLPYNEKWEF

PRNNLQFGKT LGAGAFGKVV EATAFGLGKE

DAVLKVAVKM LKSTAHADEK EALMSELKIM SHLGQHENIV

NLLGACTHGG PVLVITEYCC YGDLLNFLRR

KAEAMLGPSL SPGQDPEGGV DYKNIHLEKK
```

```
-continued
YVRRDSGFSS QGVDTYVEMR PVSTSSNDSF SEQDLDKEDG

RPLELRDLLH FSSQVAQGMA FLASKNCIHR

DVAARNVLLT NGHVAKIGDF GLARDIMNDS

NYIVKGNARL PVKWMAPESI FDCVYTVQSD

VWSYGILLWE IFSLGLNPYP GILVNSKFYK LVKDGYQMAQ

PAFAPKNIYS IMQACWALEP THRPTFQQIC

SFLQEQAQED RRERDYTNLP SSSRSGGSGS SSSELEEESS

SEHLTCCEQG DIAQPLLQPN NYQFC
``` uKit Kinase (Seq. ID No. 2) Assay

Activity of unphosphorylated c-KIT kinase (uKIT, Seq. ID no. 2) was determined by following the production of ADP from the KIT kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophotometrically. The reaction mixture (100 μl) contained unphosphorylated KIT (12 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) and ATP (2000 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader (BioTech). Reaction rates around 3 to 4 h time frame were used to calculate % inhibitions, from which IC$_{50}$ values were generated.

```
uKit with N-terminal GST fusion used for screening
                                      (Seq ID No. 2)
LGYWKIKGLV QPTRLLLEYL EEKYEEHLYE RDEGDKWRNK

KFELGLEFPN LPYYIDGDVK LTQSMAIIRY

IADKHNMLGG CPKERAEISM LEGAVDIRYG VSRIAYSKDF

ETLKVDFLSK LPEMLKMFED RLCHKTYLNG

DHVTHPDFML YDALDVVLYM DPMCLDAFPK

LVCFKKRIEA IPQIDKYLKS SKYIWPLQGW QATFGGGDHP

PKSDLVPRHN QTSLYKKAGS AAAVLEENLY

FQGTYKYLQK PMYEVQKVV EEINGNNYVY

IDPTQLPYDH KWEFPRNRLS FGKTLGAGAF GKVVEATAYG

LIKSDAAMTV AVKMLKPSAH LTEREALMSE

LKVLSYLGNH MNIVNLLGAC TIGGPTLVIT

EYCCYGDLLN FLRRKRDSFI CSKQEDHAEA ALYKNLLHSK

ESSCSDSTNE YMDMKPGVSY VVPTKADKRR SVRIGSYIER

DVTPAIMEDD ELALDLEDLL SFSYQVAKGM AFLASKNCIH

RDLAARNILL THGRITKICD FGLARDIKND

SNYVVKGNAR LPVKWMAPES IFNCVYTFESD VWSYGIFLWE

LFSLGSSPYP GMPVDSKFYK MIKEGFRMLS

PEHAPAEMYD IMKTCWDADP LKRPTFKQIV QLIEKQISES
```

-continued

TNHIYSNLAN CSPNRQKPVV DHSVRINSVG

STASSSQPLL VHDDV

Unphosphorylated PDGFRβ (uPDGFRβ) Kinase (Seq. ID No. 3) Assay

Activity of unphosphorylated PDGFRβ kinase (uPDGFRβ, Seq. ID No. 3) was determined by following the production of ADP from the kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 µL) contained PDGFRβ (DeCode, 15.7 nM), polyE4Y (2.5 mg/mL), $MgCl_2$ (10 mM), pyruvate kinase (4 units), lactate dehydrogenase (0.7 units), phosphoenol pyruvate (1 mM) and NADH (0.28 mM) and ATP (500 µM) in a 90 mM Tris buffer containing 0.2% octyl-glucoside and 1% DMSO, at pH 7.5. The inhibition reaction was started by mixing serial diluted test compound with the above reaction mixture. The absorption at 340 nm was monitored continuously for 4 h at 30° C. on a Polarstar Optima or Synergy 2 plate reader. The reaction rate was calculated using the 1.5 to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

uPDGFRβ Kinase Sequence (residues 557-1106) used for screening (Seq ID No. 3)
QKKP RYEIRW KVIE SVSSDG HEYI YVDPMQ LPYDSTWELP

RDQLVLGRTL GSGAFGQVVE ATAHGLSHSQ ATMKVAVKML

KSTARSSEKQ ALMSELKIMS HLGPHLNVVN LLGACTKGGP

IYIITEYCRY GDLVDYLHRN KHTFLQHHSD KRRPPSAELY

SNALPVGLPL PSHVSLTGE SDGGYMDMSK DESVDYVPML

DMKGDVKYAD IESSNYMAPY DNYVPSAPER TCRAT LINES

PVLSYMDLVG FSYQVANGME FLASKNCVHR DLAARNVLIC

EGKLVKICDF GLARDIMRDS NYISKGSTFL PLKWMAPESI

FNSLYTTLSD VWSFGILLWE IFTLGGTPYP ELPMNEQFYN

AIKRGYRMAQ PAHASDEIYE IMQKCWEEKF EIRPPFSQLV

LLLERLLGEG YKKKYQQVDE EFLRSDHPAI LRSQARLPGF

HGLRSPLDTS SVLYTAVQPN EGDNDYIIPL PDPKPEVADE

GPLEGSPSLA SSTLNEVNTS STISCDSPLE PQDEPEPEPQ

LELQVEPEPE LEQLPDSGCP APRAEAEDSF L

Using the enzymatic protocols described above, compounds of Formula I were shown to be inhibitors in assays measuring the kinase activity of uFMS kinase, uKIT kinase, or uPDGFRβ kinase, as indicated below in Table 1.

TABLE 1

Activity of Compounds of Formula Ia in Enyzmatic Assays of uFMS kinase, uKIT kinase, or uPDGFRβ kinase.

| Example | uFMS | uKIT | uPDGFRβ |
| --- | --- | --- | --- |
| 1 | +++ | + | + |
| 2 | +++ | + | + |
| 3 | ++++ | ++ | + |
| 4 | ++ | + | + |
| 5 | ++ | + | + |
| 6 | +++ | ++ | + |
| 7 | ++ | ++ | + |
| 8 | +++ | ++ | + |
| 9 | +++ | + | + |
| 10 | ++++ | ++ | + |
| 11 | ++ | + | + |
| 12 | ++ | + | + |
| 13 | +++ | + | + |
| 14 | ++++ | + | + |
| 15 | ++++ | ++ | ++ |
| 16 | ++++ | + | ++ |
| 17 | ++++ | + | + |
| 18 | ++++ | +++ | +++ |
| 19 | +++ | ++ | ++ |
| 20 | +++ | ++ | ++ |
| 21 | +++ | + | + |
| 22 | +++ | + | + |
| 23 | +++ | + | + |
| 24 | ++ | + | + |
| 25 | +++ | ++ | + |
| 26 | +++ | + | + |
| 27 | +++ | + | + |
| 28 | ++++ | +++ | +++ |
| 29 | ++++ | +++ | ++ |
| 30 | +++ | + | + |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM M-NFS-60 Cell Culture M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

M-NFS-60 Cell Proliferation Assay

A serial dilution of test compound was dispensed into a 384-well black clear bottom plate (Corning, Corning, N.Y.). Two thousand five hundred cells were added per well in 50 µL complete growth medium. Plates were incubated for 67 h at 37° C., 5% $CO_2$, and 95% humidity. At the end of the incubation period 10 µL of a 440 M solution of resazurin (Sigma, St. Louis, Mo.) in PBS was added to each well and incubated for an additional 5 h at 37° C., 5% $CO_2$, and 95% humidity. Plates were read on a Synergy2 reader (Biotek, Winooski, Vt.) using an excitation of 540 nM and an emission of 600 nM. $IC_{50}$ values were calculated from a series of percent inhibition values determined at a range of inhibitor concentrations using software routines as implemented in the GraphPad Prism software package.

THP-1 Cell Culture

THP-1 cells (catalog #TIB-202) were obtained from the ATCC. Briefly, cells were grown in RPMI 1640 supplemented with 10% characterized fetal bovine serum, 1% sodium pyruvate, 1% Penicillin-Streptomycin-Glutamine (PSG) and 55 uM 2-mercaptoethanol (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

Phospho-FMS ELISA Assay

A serial dilution of test compound was diluted 1:100 in assay medium (RPMI 1640 supplemented with 10% characterized fetal bovine serum) in a 96 well black clear bottom plate (Corning, Corning, N.Y.). In a separate 96 well black clear bottom plate, one hundred and fifty thousand THP-1 cells were added per well in 100 µL in assay medium. Fifty microliters of diluted compound was then added to the cells. Plates were incubated for 4 hours at 37 degrees Celsius, 5% $CO_2$, 95% humidity. At the end of the incubation period, cells were stimulated with 50 µL of a 100 nM solution of recombinant human M-CSF (catalog #216-MC, R & D Systems, Minneapolis, Minn.) in assay medium and the plate was incubated for 5 minutes at 37 degrees Celsius, 5% $CO_2$, 95% humidity. Lysates were prepared and used to perform the phospho-FMS ELISA as described by the manufacturer (catalog #DYC3268, R & D Systems, Minneapolis, Minn.). GraphPad Prism was used to calculate $IC_{50}$ values obtained from data generated from the ELISA assay.

Osteoclast Tartrate-Resistant Acid Phosphatase Assay

A serial dilution of test compound was dispensed into a 384-well black clear bottom plate (Nalge Nunc International, Rochester, N.Y.). Compound was diluted by the addition of DMEM media supplemented with 10% characterized fetal bovine serum (Invitrogen, Carlsbad, Calif.). Diluted compound was transferred to a 384-well black clear bottom plate. Two-thousand five hundred osteoclast precursors (Lonza, Walkersville, Md.) were added per well in growth media containing Receptor Activator of Nuclear Factor Kappa-beta ligand (RANKL) and M-CSF (R&D Systems, Minneapolis, Minn.). Plates were incubated for 7-14 days at 37 degrees Celsius, 5% $CO_2$, and 95% humidity to allow differentiation of osteoclast precursors. At the end of the incubation period, 10 µL of supernatant from each well was transferred to a clear 384-well plate. Tartrate-resistant acid phosphatase activity in the supernatant samples was determined using an acid phosphatase assay kit (Sigma, St. Louis, Mo.). Absorbance was measured at 550 nm using a plate reader. Data was analyzed using Prism software (Graphpad, San Diego, Calif.) to calculate $IC_{50}$ values.

The compounds of formula I were demonstrated to be functional inhibitors in one or more of the cellular assays described above, as indicated in Table 2.

TABLE 2

Inhibitory effects of compounds of formula I versus M-NFS-60, THP-1 and Osteoclast Cells

| Example | M-NFS-60 cell proliferation | Osteoclast assay | pFMS inhibition in THP-1 cells |
|---|---|---|---|
| 1 | +++ | +++ | +++ |
| 2 | ++ | +++ | NT |
| 3 | ++++ | +++ | ++++ |
| 4 | + | ++ | NT |
| 5 | + | ++ | NT |
| 6 | ++ | +++ | NT |
| 7 | + | ++ | NT |
| 8 | +++ | ++ | NT |
| 9 | +++ | +++ | +++ |
| 10 | ++++ | ++++ | +++ |
| 11 | ++ | +++ | NT |
| 12 | ++ | +++ | NT |
| 13 | +++ | +++ | +++ |
| 14 | +++ | +++ | +++ |
| 15 | ++++ | ++++ | +++ |
| 16 | ++++ | ++++ | +++ |
| 17 | +++ | ++++ | +++ |
| 18 | ++++ | ++++ | ++++ |
| 19 | ++ | +++ | NT |
| 20 | +++ | ++++ | +++ |
| 21 | +++ | +++ | +++ |
| 22 | +++ | ++++ | ++ |
| 23 | +++ | +++ | NT |
| 24 | ++ | ++ | NT |
| 25 | +++ | +++ | +++ |
| 26 | +++ | +++ | +++ |
| 27 | ++ | +++ | ++ |
| 28 | +++ | +++ | +++ |
| 29 | +++ | +++ | +++ |
| 30 | ++ | +++ | +++ |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM Measurements of In Vivo Activity Analysis of cFOS mRNA Production in a c-FMS Mouse Spleen Pharmacodynamic Model To examine the in vivo modulation of FMS activity by compounds of formula I, spleen samples from female DBA/1 mice were collected and analyzed for M-CSF stimulated production of cFOS mRNA. Briefly, six to seven week old female Taconic DBA/1BO J Bom Tac mice were treated with a single oral dose (by gavage) of either vehicle or compound. Plasma and spleen samples were collected from four mice at each timepoint 2, 4, 6, 8, 12, 18, and 24 hours after dosing. Fifteen minutes prior to euthanasia, all mice were injected IV with 1 µg (100 µL fixed volume) of M-CSF. M-CSF, Recombinant Mouse Macrophage Colony Stimulating Factor (36.4 kDa homodimer, ≥98% purity) was obtained from Gibco. All procedures carried out in this experiment were conducted in compliance with all the laws, regulations and guidelines of the National Institutes of Health (NIH). cFOS mRNA levels in spleen extracts were determined using a quantitative reverse transcriptase PCR kit from Life Technologies. Plasma levels of FMS inhibitors were determined by mass spectrometer analysis. The degree of FMS inhibition was correlative to the amount of decrease observed in cFOS mRNA levels in the spleen samples of treated animals compared to vehicle.

In this model, Examples 3, 9 and 10 afforded ≥70% inhibition of cFOS mRNA levels out to 8 h post 30 mg/kg dose.

PC-3 Peritibial Implant Model of Cancer Bone Metastasis

To evaluate in vivo anti-cancer activity of compounds of formula I, the PC-3 M-luc peritibial injection model of bone invasiveness model was employed. Briefly, PC-3 M-luc cells were obtained from Xenogen Corporation (Caliper Life Sciences) and expanded using MEM media modified with L-Glutamine (Cell Gro® #10-045-CV) supplemented with 10% fetal bovine serum, 1% penicillin-streptomycin-glutamine, 1% non-essential amino acids, and 1% MEM vitamins in 5% $CO_2$ atmosphere at 37° C. Six to 7 week old male nude mice (Crl:NU-Foxn1nu) were obtained from Charles River Laboratories. Test mice were implanted peritibially on Day 0 with $1 \times 10^6$ cells/mouse (0.1 ml) using an insulin syringe with a fixed 28-gauge needle. The needle was inserted at the ankle between the tibia and fibula until the bevel of the needle reached approximately halfway between the knee and ankle. Treatments began on Day 0. Animals were dosed by oral gavage twice daily for the study duration. All procedures carried out in this experiment were conducted in compliance with all the laws, regulations and guidelines of the National Institutes of Health (NIH). When the primary tumor reached approximately 800 mg in size, ex-vivo micro-CT was performed on the tumor bearing fixed hind limb samples using a GE RS150 small animal micro-CT scanner using with the following settings:

X-ray tube voltage=70 kVp
X-ray tube current=25 mA
Exposure time=20 ms
Number of frames=500
Angle increment between frames=0.4 o
Number of averages per frame=2
Acquisition method=Parker Images were then reconstructed at high resolution (100 microns; isotropic). Isosurface volume renderings were used to delineate lesions in the hind limbs. A constant threshold was used to produce consistent representation of the isosurface between different anatomical sites and samples. Lesions in the right hind limb were scored with values of 0, 1, 2, 3, or 4 based on a qualitative assessment of lesion size as defined by:

0: Normal Bone
1: Minimal lesions. Some roughening of the isosurface. Small areas of apparent bone resorption.
2: Mild. More numerous lesions. Significant roughening of the isosurface. Full thickness lesions apparent.
3: Moderate. Full thickness lesions larger and more numerous.
4: Marked. Many, large, full thickness lesions. Significant distortion of remaining structure. Marked bone loss.

Example 10 was evaluated in this model at an oral dose of 30 mg/kg given twice daily for 39 days and demonstrated positive benefit with a lesion score of 2 compared to a lesion score of 4 in vehicle-treated animals.

U251 Intra-Cerebro-Ventricular Implant in Mice

To evaluate in vivo anti-cancer activity compounds of formula I in combination with fractionated, localized head radiation, an orthotopic U251-luc (Luc) human glioma carcinoma model in female outbred nu/nu mice is employed. Briefly, U251 cells are obtained from the ATCC and altered to be luciferase expressing. They are grown in RPMI 1640 Media supplemented with 10% FBS and 1% PSG. The growth environment is maintained in an incubator with a 5% $CO_2$ atmosphere at 37° C. Female Harlan Nude mice (Hsd:Athymic-Nude-Foxlnu) 8-9 weeks old are used in this study. Test animals are implanted intracranially with U251-luc (Lucm-Cherry) cells. Briefly, animals are injected subcutaneously with 5 mg/kg carprofen and anesthetized using 2% isoflurane in air. The animals are then secured in a stereotaxic frame (ASIinstruments, Inc.) and a hole drilled 2 mm right lateral, 1 mm anterior to the coronal suture. The cell suspension (stored on wet ice) is mixed thoroughly and drawn up into a 50 µl syringe. The syringe needle is centered over the burr hole and lowered 3 mm into the brain and retracted 1 mm to form a "reservoir" for the deposition of the cell suspension. 10 µl of the cell suspension ($1\times10^6$ cells/mouse) is then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. All procedures carried out in this experiment are conducted in compliance with all the laws, regulations and guidelines of the National Institutes of Health (NIH). Treatment begins when the mean brain bioluminescence signal for all groups in the experiment is $\sim1.3\times10^9$ photons/sec (typically 9 days post-implant). All mice receive 2Gy of radiation each day for five consecutive days from a RadSource RS-2000 irradiator. Additionally, mice receive test compound dosed by oral gavage or optionally with co-administered bevacizumab by tail vein injection. Bioluminescence images are acquired generally on days 8, 10, 14, 17, 21, 22, 24, 28 and 35 post-implant for tumor burden estimation. For each measurement, each mouse is injected subcutaneously with 150 mg/kg D-Luciferin (Promega) and imaged 10 minutes after the injection. Images are analyzed using Living Image (Xenogen, Alameda, Calif.) software. The BLI signal in the brain is calculated with a fixed area ROI to estimate the tumor burden. Average BLI signal for each group is compared to vehicle control to determine therapeutic benefit. Twenty-eight days after the first radiation treatment mice are euthanized, via over-exposure to carbon dioxide, for blood and brain collection. Whole blood is collected via terminal cardiac puncture and placed into EDTA Microtainer® tubes. Brains are excised and placed into 10% neutral buffered formalin.

GL261 Intracranial Implant Model

To evaluate the in vivo anti-cancer activity of compounds of formula I, an intracranial implant of GL261-luc2 murine glioma is employed. Briefly GL261-luc2 cells are obtained from Caliper Life Sciences, Inc and expaned in Dulbecco's Modified Eagle Media (DMEM) which is supplemented with 10% FBS and 1% PSG. The growth environment is maintained in an incubator with a 5% $CO_2$ atmosphere at 37° C. Following expansion, cells are re-suspended using serum-free media to generate a concentration of $1\times10^8$ cells/mL. Six to seven week old female C57BL/6J-Tyrc-2J/J from Jackson Labs are implanted intracranially on Day 0 with GL261-luc2 cells. For aseptic surgical implantation, animals are injected subcutaneously with 5 mg/kg carprofen, anesthetized using 2% isoflurane in air. The animals are then secured in a stereotaxic frame (ASIinstruments, Inc.) and a hole is drilled 2 mm right lateral, 1 mm anterior to the coronal suture. The cell suspension (stored on wet ice) is mixed thoroughly and drawn up into a 50 µL syringe. The syringe needle is centered over the burr hole and lowered 3 mm into the brain and retracted 1 mm to form a "reservoir" for the deposition of the cell suspension. 10 µL of the cell suspension ($1\times10^6$ cells/mouse) is then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. The quantity of emitted light from the tumor after systemic injection of D-Luciferin is expected to correlate with tumor size. Each mouse is injected intraperitoneally (IP) with 150 mg/kg D-Luciferin and imaged in the prone position 10 minutes after the injection. Medium and small binning of the CCD chip is used, and the exposure time is adjusted (10 seconds to 1 minute) to obtain at least several hundred counts from the tumors and to avoid saturation of the CCD chip. Images are analyzed using Living Image (Xenogen, Alameda, Calif.) software. Each unique signal is circled manually and labeled by group and mouse number. Treatment begins by oral gavage of test compound when the mean brain bioluminescence signal for all groups in the experiment is $280\times10^6$ photons/sec. All procedures carried out in this experiment are conducted in compliance with all the laws, regulations and guidelines of the National Institutes of Health (NIH).

At the end of study all mice are euthanized via over-exposure to carbon dioxide for blood and brain collection. Whole blood is collected via terminal cardiac puncture and placed into EDTA Microtainer® tubes. Brains are excised and placed into 10% neutral buffered formalin.

MDA-MB-231 Xenograft Study

To evaluate the in vivo anti-cancer activity compounds of formula I, a MDA-MB-231-luc-D3H2LN human breast carcinoma xenograft is employed. Briefly, MDA-MB-231-luc-D3H2LN cells are obtained from Xenogen and expanded in Minimal Essential Media (MEM) with EBSS which is modified with 1% L-glutamine and supplemented with 10% FBS, 1% PSG, 1% non-essential amino acids, and 1% sodium pyruvate. The growth environment is maintained in an incubator with a 5% $CO_2$ atmosphere at 37° C. Cells are harvested and re-suspended using 50% serum-free media and 50% Matrigel® to generate a stock concentration of $5 \times 10^6$ cells/mL.

Six to 7 week old female C.B-17/IcrHsd-PrkdcscidLystbg mice are injected with 200 µL of cell suspension subcutaneously, just below the right axilla. All procedures carried out in this experiment are conducted in compliance with all the laws, regulations and guidelines of the National Institutes of Health (NIH). Treatment begins when the mean tumor burden is approximately 150 mg. All mice are dosed with test compound by oral gavage. Body weights and tumor measurements are recorded three times weekly. Tumor burden (mg) is estimated from caliper measurements by the formula for the volume of a prolate ellipsoid assuming unit density as: Tumor burden (mg)=(L×W2)/2, where L and W are the respective orthogonal tumor length and width measurements (mm). The primary endpoints to evaluate efficacy is % T/C. % T/C is defined as the median tumor mass of a Treated Group divided by the median tumor mass of the Control Group×100. Ex vivo bioluminescence imaging is performed as animals exit the study, using an IVIS 50 optical imaging system (Xenogen, Alameda, Calif.). Animals are injected IP with 150 mg/kg D-Luciferin (Promega) and euthanized 10 minutes following the injection. The primary tumor is removed and snap frozen for future analysis and the mouse opened and imaged in the supine position. Large binning of the CCD chip is used, and the exposure time is adjusted (1 to 2 minutes) to obtain at least several hundred counts from the tumors and to avoid saturation of the CCD chip. Images are analyzed using Living Image (Xenogen, Alameda, Calif.) software. Each unique signal is circled manually and labeled by group and mouse number. Total BLI signal is correlative to tumor size and compared to vehicle control to determine treatment benefit.

Certain 2-aminopyrimidin-6-ones have been reported to be inhibitors of VEGFR/KDR and/or c-MET kinases in WO2008/079291 and are illustrated in FIG. 1, below. Evidence of kinase inhibition was only reported for certain inhibitors of WO2008/079291 versus cMET kinase, with $K_i$'s ranging from 6-87 nM (indicated in FIG. 1). No information regarding inhibition of c-FMS kinase was disclosed in WO2008/079291. These compounds of WO2008/079291 differ from compounds of the instant invention by the presence of an arylamino "A" moiety in Formula I of the instant invention [wherein A is NR2(R3), R2 is aryl and R3 is H].

These compounds of WO2008/079291 are outside the scope of the instant invention. Nonetheless, the compounds of the instant invention have been screened against both c-MET and KDR kinase. Unexpectedly, it has been found that the compounds of the instant invention afford high levels of selectivity for c-FMS kinase versus c-MET and KDR kinases. The most potent compound of Formula I in the c-MET assay exhibited an $IC_{50}$ value of 3.4 micromolar, versus 0.0016 micromolar in the u-FMS assay, a selectivity of 2125-fold. The most potent compound of Formula I in the KDR assay exhibited an $IC_{50}$ value of 1.4 micromolar, versus 0.0016 micromolar in the u-FMS assay, a selectivity of 875-fold. These data evidence that compounds of the present invention (A is non-aromatic moiety) potently inhibit c-FMS kinase but do not readily inhibit cMET and KDR kinase activity. These results could not be anticipated by the prior teachings of WO2008/079291.

Figure 1. cMET inhibitors of WO2008/079291.

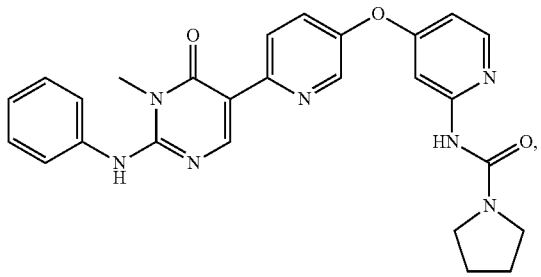

Ex 1

WO2008/079291
cMET Ki = 11 nM

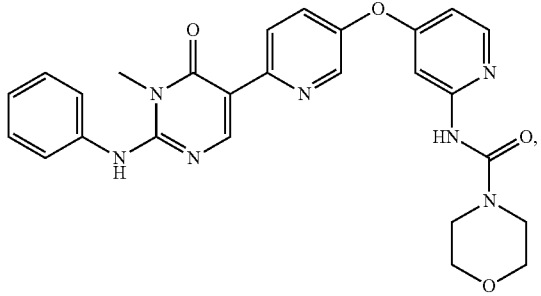

Ex 6

WO2008/079291
cMET Ki = 57 nM

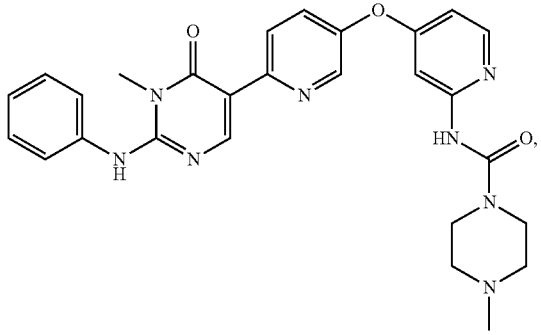

Ex 7

WO2008/079291
cMET Ki = 87 nM

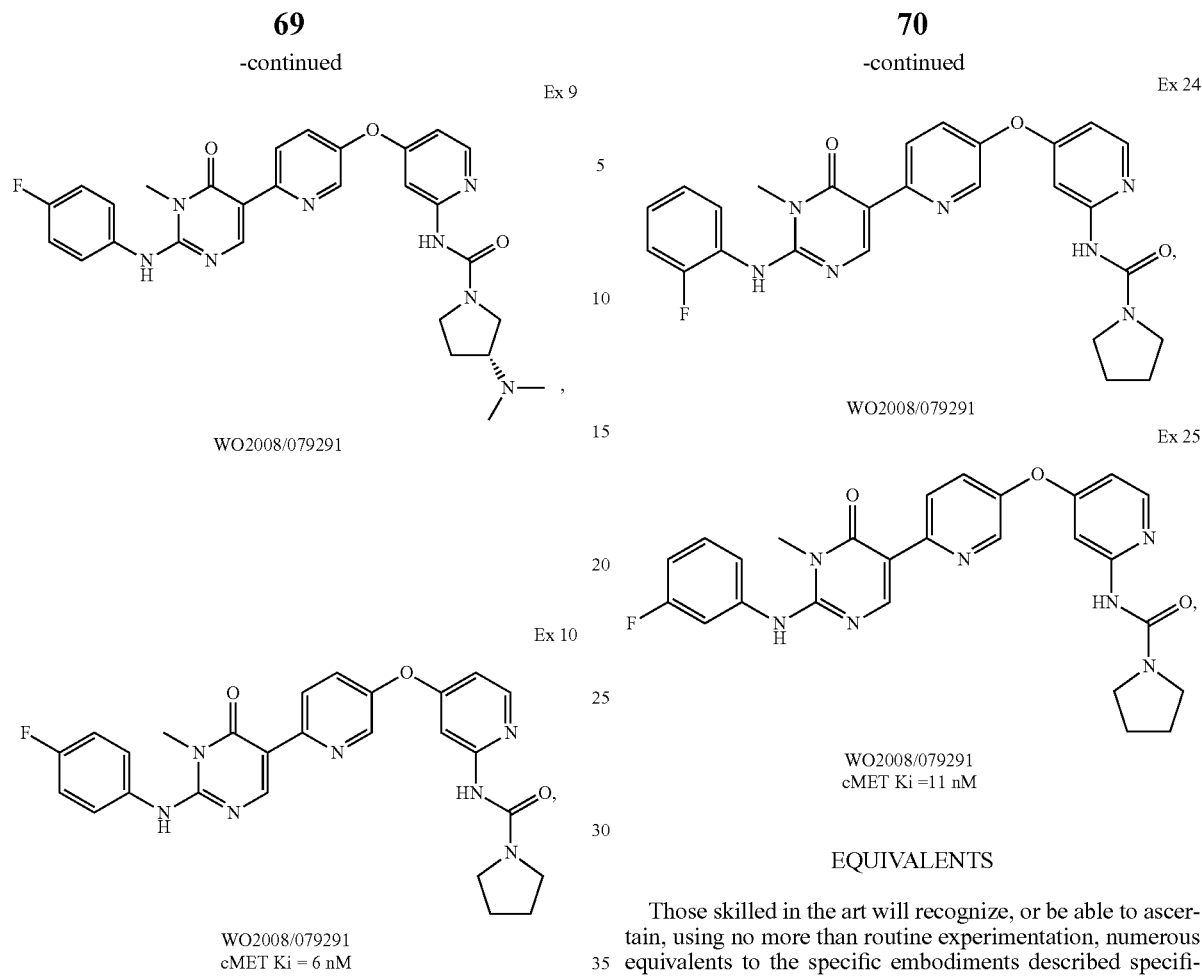

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I,

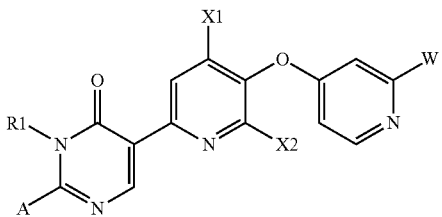

or a pharmaceutically acceptable salt, enantiomer, stereoisomer, or tautomer thereof, wherein A is taken from the group consisting of —N(R2)R3 and G;
G is selected from the group consisting of

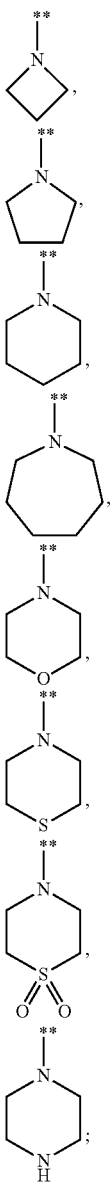

and wherein the symbol (**) is the point of attachment to the pyrimidine ring;

each G moiety may be further substituted with one, two, or three R4 moieties;

W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties;

X1 and X2 are individually and independently hydrogen or C1-C6 alkyl;

R1 is hydrogen, C1-C6 alkyl, deutero-C1-C6 alkyl wherein the alkyl chain is partially or completely deuterated, or branched C3-C8 alkyl;

R2 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated, —(CH$_2$)$_m$—OR8, or a 3-8 membered heterocyclic ring, wherein each alkylene is optionally substituted with C1-C4 alkyl;

R3 is hydrogen, C1-C6 alkyl, deutero-C1-C6 alkyl wherein the alkyl chain is partially or completely deuterated, branched C3-C8 alkyl, C3-C8 cycloalkyl, fluoroC1-C6alkyl wherein the alkyl is fully or partially fluorinated or a 3-8 membered heterocyclic ring;

each R4 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, —(CH$_2$)$_m$—OR8, —(CH$_2$)$_m$—NR8(R9), —(CH$_2$)$_m$—R7, or cyano, wherein each alkylene is optionally substituted with C1-C4 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl;

Each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkylene is optionally substituted with C1-C4 alkyl;

each R7 is independently and individually selected from the group consisting of

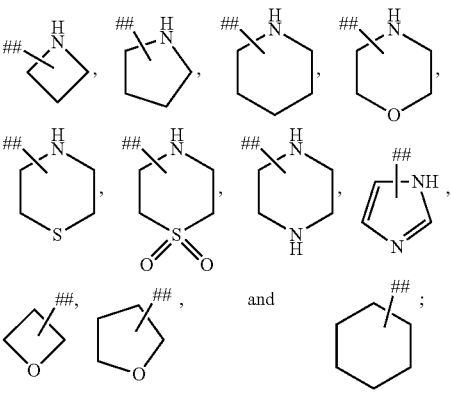

and wherein the symbol (##) is the point of attachment to respective W, R5 or R6 moieties containing a R7 moiety;

each R7 is optionally substituted with —(R10)$_p$;

each R8 and R9 is individually and independently hydrogen, C1-C6 alkyl, fluoro-C1-C6 alkyl wherein the alkyl chain is partially or completely fluorinated, or branched C3-C8 alkyl;

each R10 is individually and independently C1-C6 alkyl, —(CH$_2$)$_m$—CN, —(CH$_2$)$_m$—OR3, —(CH$_2$)$_m$—NR8 (R9), or —(CH$_2$)$_m$—C(O)—R6, wherein each alkyl or alkylene is optionally substituted with one or two C1-C6 alkyl;

wherein each alkylene is optionally substituted with C1-C4 alkyl each m is individually and independently 0, 1, 2, or 3; and each p is 0, 1, 2, or 3.

2. The compound of claim 1 wherein the compound is a compound of Formula Ia,

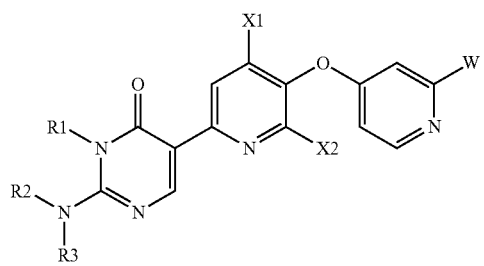

Formula Ia or a pharmaceutically acceptable salt, enantiomer, stereoisomer, or tautomer thereof.

3. The compound of claim 2 wherein R3 is hydrogen.

4. The compound of claim 3 wherein the compound is a compound of Formula Ib,

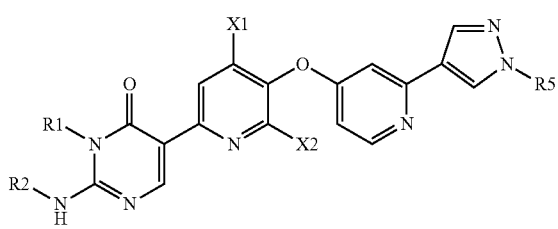

Formula Ib

5. The compound of claim 4 wherein one of X1 and X2 is C1-C6alkyl and the other is hydrogen.

6. The compound of claim 5, wherein R1 is hydrogen.

7. The compound of claim 5, wherein R1 is C1-C6alkyl.

8. The compound of claim 1 wherein the compound is a compound of Formula Ic,

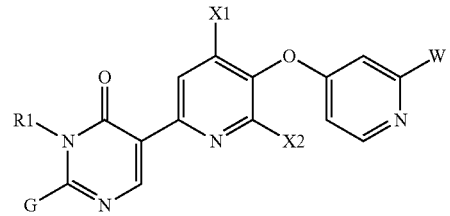

Formula Ic or a pharmaceutically acceptable salt, enantiomer, stereoisomer, or tautomer thereof.

9. The compound of claim 8 wherein the compound is a compound of Formula Id,

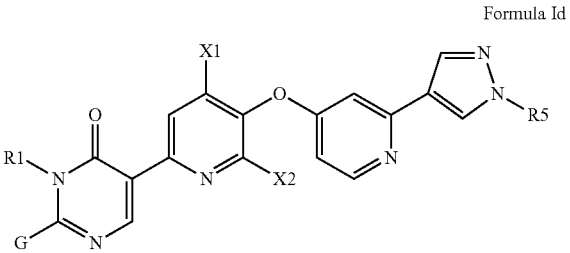

Formula Id

10. The compound of claim 9 wherein one of X1 and X2 is C1-C6alkyl and the other is hydrogen.

11. The compound of claim 10, wherein R1 is hydrogen.

12. The compound of claim 10, wherein R1 is C1-C6alkyl.

13. A compound selected from the group consisting of 2-(ethylamino)-5-(6-methyl-5-((2-(1-methyl-1H-pyrazol-4-yl)pyridin-4-yl)oxy)pyridin-2-yl)pyrimidin-4(3H)-one, 2-(dimethylamino)-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(6-methyl-5-((2-(1-methyl-1H-pyrazol-4-yl)pyridin-4-yl)oxy)pyridin-2-yl)pyrimidin-4(3H)-one, 2-(ethylamino)-5-(6-methyl-5-((6'-methyl-[2,3'-bipyridin]-4-yl)oxy)pyridin-2-yl)pyrimidin-4(3H)-one, 2-(ethylamino)-5-(6-methyl-5-((2-(4-methyl-1H-imidazol-1-yl)pyridin-4-yl)oxy)pyridin-2-yl)pyrimidin-4(3H)-one, 2-((2-methoxyethyl)amino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(methylamino)pyrimidin-4(3H)-one, 2-(ethylamino)-5-(5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(pyrrolidin-1-yl)pyrimidin-4(3H)-one, 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one, 4-((6-(2-(isopropylamino)-6-oxo-1,6-dihydropyrimidin-5-yl)pyridin-3-yl)oxy)-N-methylpicolinamide, 5-(6-methyl-5-((2-(1-methyl-1H-pyrazol-4-yl)pyridin-4-yl)oxy)pyridin-2-yl)-2-morpholinopyrimidin-4(3H)-one, 5-(6-methyl-5-((2-(1-methyl-1H-pyrazol-4-yl)pyridin-4-yl)oxy)pyridin-2-yl)-2-(piperidin-1-yl)pyrimidin-4(3H)-one, 2-(cyclopropylamino)-5-(6-methyl-5-((2-(1-methyl-1H-pyrazol-4-yl)pyridin-4-yl)oxy)pyridin-2-yl)pyrimidin-4(3H)-one, 2-(cyclopentylamino)-5-(6-methyl-5-((2-(1-methyl-1H-pyrazol-4-yl)pyridin-4-yl)oxy)pyridin-2-yl)pyrimidin-4(3H)-one, 3-methyl-5-(6-methyl-5-((2-(1-methyl-1H-pyrazol-4-yl)pyridin-4-yl)oxy)pyridin-2-yl)-2-

(pyrrolidin-1-yl)pyrimidin-4(3H)-one, 2-(cyclopropylamino)-3-methyl-5-(6-methyl-5-((2-(1-methyl-1H-pyrazol-4-yl)pyridin-4-yl)oxy)pyridin-2-yl)pyrimidin-4(3H)-one, 2-(isopropylamino)-5-(4-methyl-5-((2-(1-methyl-1H-pyrazol-4-yl)pyridin-4-yl)oxy)pyridin-2-yl)pyrimidin-4(3H)-one, N-(4-((6-(2-(isopropylamino)-6-oxo-1,6-dihydropyrimidin-5-yl)-2-methylpyridin-3-yl)oxy)pyridin-2-yl)acetamide, 5-(4-methyl-5-((2-(1-methyl-1H-pyrazol-4-yl)pyridin-4-yl)oxy)pyridin-2-yl)-2-(pyrrolidin-1-yl)pyrimidin-4(3H)-one, 5-(5-((2-(1-ethyl-1H-pyrazol-4-yl)pyridin-4-yl)oxy)-6-methylpyridin-2-yl)-2-(isopropylamino)pyrimidin-4(3H)-one, (R)-2-((1-methoxypropan-2-yl)amino)-5-(6-methyl-5-((2-(1-methyl-1H-pyrazol-4-yl)pyridin-4-yl)oxy)pyridin-2-yl)pyrimidin-4(3H)-one, (R)-2-(2-(methoxymethyl)pyrrolidin-1-yl)-5-(6-methyl-5-((2-(1-methyl-1H-pyrazol-4-yl)pyridin-4-yl)oxy)pyridin-2-yl)pyrimidin-4(3H)-one, (S)-2-(3-(dimethylamino)pyrrolidin-1-yl)-5-(6-methyl-5-((2-(1-methyl-1H-pyrazol-4-yl)pyridin-4-yl)oxy)pyridin-2-yl)pyrimidin-4(3H)-one, 2-(ethylamino)-3-methyl-5-(6-methyl-5-((2-(1-methyl-1H-pyrazol-4-yl)pyridin-4-yl)oxy)pyridin-2-yl)pyrimidin-4(3H)-one, 2-((2-methoxyethyl)amino)-3-methyl-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-((tetrahydro-2H-pyran-4-yl)amino)pyrimidin-4(3H)-one, 2-(tert-butylamino)-5-(6-methyl-5-((2-(1-methyl-1H-pyrazol-4-yl)pyridin-4-yl)oxy)pyridin-2-yl)pyrimidin-4(3H)-one, 5-(6-methyl-5-((2-(1-methyl-1H-pyrazol-4-yl)pyridin-4-yl)oxy)pyridin-2-yl)-2-(neopentylamino)pyrimidin-4(3H)-one, and 2-(3,3-difluoropyrrolidin-1-yl)-5-(6-methyl-5-((2-(1-methyl-1H-pyrazol-4-yl)pyridin-4-yl)oxy)pyridin-2-yl)pyrimidin-4(3H)-one.

14. A pharmaceutical composition, comprising a compound of claim 13 and a pharmaceutically acceptable carrier.

15. The compound 2-(ethylamino)-5-(6-methyl-5-((2-(1-methyl-1H-pyrazol-4-yl)pyridin-4-yl)oxy)pyridin-2-yl)pyrimidin-4(3H)-one.

16. A pharmaceutical composition, comprising the compound of claim 15 and a pharmaceutically acceptable carrier.

17. The composition of claim 16 further comprising an additive selected from adjuvants, excipients, diluents, or stabilizers.

18. The compound 2-(isopropylamino)-5-(6-methyl-5-((2-(1-methyl-1H-pyrazol-4-yl)pyridin-4-yl)oxy)pyridin-2-yl)pyrimidin-4(3H)-one.

19. A pharmaceutical composition, comprising the compound of claim 18 and a pharmaceutically acceptable carrier.

20. The composition of claim 19 further comprising an additive selected from adjuvants, excipients, diluents, or stabilizers.

21. The compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one.

22. A pharmaceutical composition, comprising the compound of claim 21 and a pharmaceutically acceptable carrier.

23. The composition of claim 22 further comprising an additive selected from adjuvants, excipients, diluents, or stabilizers.

24. A pharmaceutical composition, comprising a compound of claim 1 and a pharmaceutically acceptable carrier.

25. The composition of claim 24 further comprising an additive selected from adjuvants, excipients, diluents, or stabilizers.

26. A method of treating gastrointestinal stromal tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, cancers that are metastatic to bone, papillary thyroid carcinoma, non-small cell lung cancer, colonic cancers, rheumatoid arthritis, osteoarthritis, autoimmune nephritis, lupus, Crohn's disease, asthma, chronic obstructive pulmonary disease, osteoporosis, mastocytosis, or mast cell leukemia, the method comprising administering to a human patient in need thereof an effective amount of a compound of claim 1, or a pharmaceutically acceptable salt, enantiomer, stereoisomer, or tautomer thereof.

27. A method of treating glioblastomas, breast cancers, pancreatic cancers, or cancers that are metastatic to bone, the method comprising administering to a human patient in need thereof an effective amount of a compound of claim 1, or a pharmaceutically acceptable salt, enantiomer, stereoisomer, or tautomer thereof.

28. The method of claim 26, wherein the compound is administered orally, parenterally, by inhalation, or subcutaneously.

29. The method of claim 27, wherein the compound is administered orally, parenterally, by inhalation, or subcutaneously.

* * * * *